US006916619B2

(12) United States Patent
Jones et al.

(10) Patent No.: US 6,916,619 B2
(45) Date of Patent: Jul. 12, 2005

(54) COMPOSITIONS AND METHODS FOR GENETIC ANALYSIS OF POLYCYSTIC KIDNEY DISEASE

(75) Inventors: Jeffrey George Jones, Wilbraham, MA (US); Aidan Noel Hennigan, Millbury, MA (US); John A. Curran, Worcester, MA (US); Susan Kimberly Allen, Worcester, MA (US); Normand J. Robichaud, Leominster, MA (US); Jing Wang, Worcester, MA (US); Kerry Ellen Flynn, Grafton, MA (US); Jorge A. Garcés, Dudley, MA (US); Christopher M. Palatucci, Shrewsbury, MA (US)

(73) Assignee: Athena Diagnostics, Inc., Worcester, MA (US)

(*) Notice: Subject to any disclaimer, the term of this patent is extended or adjusted under 35 U.S.C. 154(b) by 377 days.

(21) Appl. No.: 10/083,246

(22) Filed: Feb. 26, 2002

(65) Prior Publication Data

US 2003/0152936 A1 Aug. 14, 2003

Related U.S. Application Data

(60) Provisional application No. 60/328,739, filed on Oct. 12, 2001.

(51) Int. Cl.[7] .................................................. C12Q 1/68
(52) U.S. Cl. .......................... 435/6; 435/91.1; 435/91.2
(58) Field of Search ..................................... 435/6, 91.2

(56) References Cited

U.S. PATENT DOCUMENTS

| 5,891,628 | A | * | 4/1999 | Reeders et al. ................ | 435/6 |
| 6,031,088 | A | | 2/2000 | Somlo et al. ............... | 536/23.5 |
| 6,071,717 | A | | 6/2000 | Klinger et al. ............. | 435/69.1 |
| 6,228,591 | B1 | | 5/2001 | Somlo et al. .................. | 435/6 |
| 6,485,960 | B1 | * | 11/2002 | Harris et al. ............. | 435/252.3 |
| 2003/0008288 | A1 | | 1/2003 | Germino et al. ................ | 435/6 |

FOREIGN PATENT DOCUMENTS

WO  WO 02/06529 A2  1/2002  ............ C12Q/1/68

OTHER PUBLICATIONS

Phakdeekitcharoen, B. et al., (2001), "Mutation Analysis of the Entire Replicated Portion of PKD1 Using Genomic DNA Samples", *J. Am. Soc. Nephrol*, 12:955–963.
Perrichot, R.A. et al., (1999), "DGGE screening of PKD1 gene reveals novel mutations in a large cohort of 146 unrelated patients", *Hum. Genet.*, 105:231–239.
Thomas, R. et al., (1999), "Identification of Mutations in the Repeated Part of the Autosomal Dominant Polycystic Kidney Disease Type 1 Gene, PKD1, by Long–Range PCR", *Am. J. Hum. Genet.*, 65:39–49.

Watnick, T. et al., (1999), "Mutation Detection of PKD1 Identifies a Novel Mutation Common to Three Families with Aneurysms and/or Very–Early–Onset Disease", *Am. J. Hum. Genet.*, 65:1561–1571.
Watnick, T.J. et al., (1998), "Somatic Mutation in Individual Liver Cysts Supports a Two–Hit Model of Cystogenesis in Autosomal Dominant Polycystic Kidney Disease", *Molecular Cell*, 2:247–251.
Roelfsema, J.H. et al., (1997), "Mutation Detection in the Repeated Part of the PKD1 Gene", *Am. J. Hum. Genet.*, 61:1044–1052.
Watnick, T.J. et al., (1997), "An unusual pattern of mutation in the duplicated portion of PKD1 is revealed by use of a novel strategy for mutation detection", *Human Molecular Genetics*, 6(9):1473–1481.
Neophytou, P. et al., (1996), "Detection of a novel nonsense mutation and an intragenic polymorphism in the PKD1 gene of a Cypriot family with autosomal dominant polycystic kidney disease", *Hum. Genet.*, 98:437–442.
Peral, B. et al., (1996), "Screening the 3' Region of the Polycystic Kidney Disease 1 (PKD1) Gene Reveals Six Novel Mutations", *Am. J. Hum. Genet.*, 58:86–96.
Turco, A.E. et al., (1995), "A novel nonsense mutation in the PKD1 gene (C3817T) is associated with autosomal dominant polycystic kidney disease (ADPKD) in a large three–generation Italian family", *Human Molecular Genetics*, 4(8):1331–1335.
Ward, C.J. et al., (1995), "*Homo sapiens* polycystic kidney disease–associated protein (PKD1) gene, complete eds", Database EMBL Online, Database Accession No. L39891:1–20.
International Search Report of International Application No. PCT/US01/22035.
Rossetti, et al., *Mutation Analysis of the Entire PKD1 Gene: Genetic and Diagnostic Implications*, 2000, Am. J. Hum. Genet., 68:46–63.
Underhill, et al., *Detection of Numerous Y Chromosome Biallelic Polymorphisms by Denaturing High–Performance Liquid Chromatography*, 1997, Genome Research, 7:996–1005.
Liu, et al., *Denaturing High Performance Liquid Chromatograph (DHPLC) Used in the Detection of Germline and Somatic Mutations*, 1998, Nucleic Acids Research, vol. 26, No. 6, 1396–1400.

* cited by examiner

*Primary Examiner*—Kenneth R. Horlick
(74) *Attorney, Agent, or Firm*—Kathleen M. Williams; Palmer & Dodge LLP

(57) ABSTRACT

The subject invention relates to methods for detection of mutations in a PKD gene using DHPLC. The invention includes the following aspects: identification of PKD unique sites; design of PKD-specific primers; amplification of PKD-specific products; and analysis of PCR amplified products by DHPLC. The invention further relates to compositions such as identified unique sites and PKD-specific primers, and kits for performing the methods of the invention.

23 Claims, 54 Drawing Sheets

Figure 1.

| Codon Number | | |
|---|---|---|
| | | Exon 1 |
| 1 | 212 | atgccgcccgcggcgccgccgcgcctgcgcctggcgctggcgggcct |
| | | M P P A A P A R L A L A L G |
| 16 | 257 | ggcctgtggctgggcgctggcggagggcccggggcgcggctg |
| | | G L W L G A L A G G P G R G |
| 31 | 302 | tggccctgcgagccccctgcctcgcagcccagcgccgtcga |
| | | C P C E P P C L G P A P G |
| 46 | 347 | cctgccgcgtcaactgctcgggccgcggctgcgacgctcagt |
| | | A C R V N C S G R G L R T L |
| | | Exon 2 |
| 61 | 392 | ccgcgctgcgcat cccgcggacgccacagcgct |
| | | P A L R I P A D A T |
| 76 | 437 | |
| | | Exon 3 |
| 91 | 482 | tgatataagcaacaacaagatttctacc |
| | | D I S N N K I S T |
| | | Exon 4 |
| 106 | 527 | ctagaagaagaatattttgctaattt ttctaatttaagtgaatt |
| | | E E G I F A N L F N L S E |
| 121 | 572 | |
| 136 | 617 | |
| 151 | 662 | |
| | | Exon 5-A |
| 166 | 707 | gtgaggactat |
| | | G E E Y |
| 181 | 752 | gtcgcctgcctccctgacaacagctcaggcaccgtggcagcagtc |
| | | V A C L P D N S S G T V A A V |
| 196 | 797 | tccttttcagctgccgcacgaaggcctgcttcagccagaggcctgc |
| | | S F S A A H E G L L Q P E A |

```
       7862  ...
2551         . A V V V Q D L G A A V V /
                    Exon
       7907  ...
2566         . N P ...

7952  ...
2581         ...

7997  ...
2596                                    Exon 21
       8042  ...
2611                            . Y E K /

8087  ...
2626         . D V A A E P E P R Q H R /

8132  ...
2641         . I K H F T E T V S K /

8177  ...
2656         . T V D D I Q Q L A A L A /
                   Exon
       8222  ...
2671         . M F ...

8267  ...
2686         ...

8312  ...
2701                        Exon 23-A
       8357  ...         agacctcatccacctggccagctggac
2716         ...         H L I H L A S /

9077 ...
2956                                    Exon 25

```
3016              D Y F S E E D M V W R T E G I
       9302
3031              P L E E T S P R Q A V C L S
       9347
3046              R H L T A F G A S L F V P
       9392
3061              I V R F V F P
       9437
3076
       9482
3091
       9527
3106                                              Exon 27
       9572
3121                                                T
       9617
3136              V H V G I M L Y G V D S R S
       9662
3151              I R H L D G D R A F H R N S
       9707
3166              D I F R I A T P H S L G S V V
                                              Exon 28
       9752
3181              I R V W H D N K
       9797
3196
       9842
3211                                              Exon 29
       9887
3226                                              S D A
       9932
3241              V L L R R L L V A E L Q
```

```
              Exon 35
         10697  ...
    3496        ... S T P G E K T E T 10742  tcgctgcagagctgg...gctgg...tcccagccagcccct
    3511        V L Q R L E L G I P S P G
                                              Exon 36
         10787  ...
    3526        W E Q A A K L R T 10832
    3541

10877
    3556

10922
    3571

10967
    3586
                        Exon 37
         11012  ...
    3601        V L E A L Y F 11057  tcgtgaccaagcgctgcaccggttgatgatgcagccctgata
    3616        V A K R L H P D E D T L 11102  catgcccgggctgtaagctggaccaactgtgcccccgcgta
    3631        S P A V P V S A R V P R 11147  cggccaccccacggctttgcactcttcctggccaacaagcaac
    3646        P P H G F A L F L A K E R Exon 38
         11192  cgcaaggtcaaaagactacatggcatgctcaagcc...
    3661        R K V K R L H G M L K 11237
    3676

11282
    3691
                                            Exon 39
         11327  ...
    3706

11372  tggctctggccatcgatggccacatgcactgccgcacgtccag
```

FIG 1 Cont.

```
3721              L W P W M A H V L L P Y V 11417
3736              N Q S P L P P R L R
                               Exon 40
       11462
3751              R Q L 11507
3766

11552
3781                             Exon 41
       11597
3796              A W S W G S 11642
3811              V Y D G V Q E L G L 11687
3826              E S R D R L R L Q L H
                               Exon 42
       11732
3841              L D N 11777
3856

11822
3871

11867
3886                            Exon 43
       11912
3901              V L L I A V H F 11957
3916              E A R W H R E G R W V 12002
3931              L G A W A R W L I V A L T 12047
3946              T A L V R L A Q L G A A D
```

Exon 1—Homolog 1

```
Query:  3844  ccgcggacgccacagcgctgtgagtagcgggcccagcggcacccgggagaggccgcggga  3903
              ||||||||||||||||||||||||||||||||||||||||||||||||||||||||||||
Sbjct: 16586  ccgcggacgccacagcgctgtgagtagcgggcccagcggcacccgggagaggccgcggga 16645

Query:  3904  cgggcgggcgtgggcgggttccctggcccgggacgggaagcaggacgcgggccaggacgc  3963
              ||||||||||||||| ||||||||||||||||||||||||||||||||||||||||||||
Sbjct: 16646  cgggcgggcgtgggcgcgttccctggcccgggacgggaagcaggacgcgggccaggacgc 16705

Query:  3964  tcccagggg cgaggctccggcgcggcacggcgggccctgctaaataaggaacgcctggag 4023
              ||||||||   ||||||||||||||||||||| ||||  |||||||||||||||||||||
Sbjct: 16706  tcccaggg-cgaggctccggcgcggcacagcgg-ccctgctaaataaggaacgcctggag 16763

Query:  4024  ccgcggttggcacggccccggggagccgaaaaacccgggtctggagacagacgtcccac  4083
              |||||||||||||||||||||||||||||||||||||||||||||||||||||||||||
Sbjct: 16764  ccgcggttggcacggccccggggagccgaaaaacccgggtctggagacagacgtcccac 16823

PstI
Query:  4084  ccgggggctctgcagacgccagcggggcggggcgcggaggccgcgctcagctgggagga  4143
              ||||||||||||  ||||||||||||||||||||||||||||||||||||||||||||
Sbjct: 16824  ccgggggctctgcggacgccagcggggcggggcgcggaggccgcgctcagctgggagga 16883

Query:  4144  caaacagtcgctaattggagaggaattgggatgcggcctggggctgcggggtacccggag  4203
              |||||||||||||||||||||||||||||| |||||||||||||||||||||||||||||
Sbjct: 16884  caaacagtcgctaattggagaggaattgggattcggcctggggctgcggggtacccggag 16943

Query:  4204  aggtggggatggctgtaggggg cggcagggaagagttccaggaggtgtctggaaaaggat  4263
              || |||||||||||||||||||  |||||||||||||||||||||||||||| | |||||
Sbjct: 16944  agatggggatggctgtaggggg ctgcagggaagagttccaggaggtgtctggacaaggat 17003
```

Exon 1—Homolog 1

```
Query:  3844  ccgcggacgccacagcgctgtgagtagcgggcccagcggcacccgggagaggccgcggga  3903
              ||||||||||||||||||||||||||||||||||||||||||||||||||||||||||||
Sbjct: 16586  ccgcggacgccacagcgctgtgagtagcgggcccagcggcacccgggagaggccgcggga 16645

Query:  3904  cgggcgggcgtgggcgggttccctggcccgggacgggaagcaggacgcgggccaggacgc  3963
              ||||||||||||||| ||||||||||||||||||||||||||||||||||||||||||||
Sbjct: 16646  cgggcgggcgtgggcgcgttccctggcccgggacgggaagcaggacgcgggccaggacgc 16705

Query:  3964  tcccagggg cgaggctccggcgcggcacggcgggccctgctaaataaggaacgcctggag 4023
              ||||||||   ||||||||||||||||||||| ||||  |||||||||||||||||||||
Sbjct: 16706  tcccaggg-cgaggctccggcgcggcacagcgg-ccctgctaaataaggaacgcctggag 16763
```

FIG 2 Cont.

Stretch of Exon 6—Homolog 1

```
Query: 21589 tcgttcccaccggtctccagcggtgcacccgctctgccctcggacacggagatcttccc 21648
              ||||||||||||||||||||||||||||||||||||||||||||||||||||||||||| |
Sbjct: 23917 tcgttcccaccggtctccagcggtgcacccgctctgccctcggacacggagatcttctc 23976

Query: 21649 tggcaacgggcactgctaccgcctggtggtggagaaggcggcctggctgcaggcgcagga 21708
              ||||| |||||||||||||||||||||||||||||||||||||||||||||||||||||
Sbjct: 23977 tggcaatgggcactgctaccgcctggtggtggagaaggcggcctggctgcaggcgcagga 24036
                         StuI
Query: 21709 gcagtgtcaggcctgggccggggccgccctggcaatggtggacagtcccgccgtgcagcg 21768
              ||||||| ||||||||||||||| ||||||||||||||||||||||||||||||||||||
Sbjct: 24037 gcagtgtcgggcctgggccggggccaccctggcaatggtggacagtcccgccgtgcagcg 24096
```

Stretch of Exon 6—Homolog 2

```
Query: 21589 tcgttcccaccggtctccagcggtgcacccgctctgccctcggacacggagatcttccc 21649
              ||||||||||||||||||||||||||||||||||||||||||||||||||||||||||| |
Sbjct: 63611 tcgttcccaccggtctccagcggtgcacccgctctgccctcggacacggagatcttctc 63670

Query: 21649 tggcaacgggcactgctaccgcctggtggtggagaaggcggcctggctgcaggcgcagga 21708
              |||||||||||||||||||||||||||||||||||||||||||||||||||||||||||
Sbjct: 63671 tggcaacgggcactgctaccgcctggtggtggagaaggcggcctggctgcaggcgcagga 63730

Query: 21709 gcagtgtcaggcctgggccggggccgccctggcaatggtggacagtcccgccgtgcagcg 21768
              ||||||| |||||||||||||||| ||||||||||||||||||||||||||||||||||
Sbjct: 63731 gcagtgtcgggcctgggccggggccaccctggcaatggtggacagtcccgccgtgcagcg 63790
```

FIG 2 Cont.

Stretch of Exon 10-Homolog 1

```
Query: 23622 aaatcagggccccaacaccctccctcctcacagggaccccggagaacggcagcgagcct 23681
              ||| ||||||||||||||||||||||| ||||||||||||||||||||||||||||||
Sbjct: 25938 gaatgagggccccaacaccctccctcctcgcagggaccccggagaacggcagcgagcct 25997

Query: 23682 gagagcaggtccccggacaacaggacccagctggccccgcgtgcatgccaggggacgc 23741
              ||||||||||||||||||||||||||||||||||||||||||||||||||||||||||
Sbjct: 25998 gagagcaggtccccggacaacaggacccagctggccccgcgtgcatgccaggggacgc 26057

Query: 23742 tggtgccctggagccaacatctgcttgccgctggacgcctcctgccaccccaggcctgc 23801
              |||||||||||||||||||||||||||||||||||||| |||||||||||  |||||||
Sbjct: 26058 tggtgccctggagccaacatctgcttgccgctggacacctcctgccaccc-aggcctgc 26116

XmaI
Query: 23802 gccaatggctgcacgtcaggg-ccagggctacccggggcccctatgcgctatggagaga 23860
              |||||||||||||||||||||  |||||||| ||||||||||||||||||||||||||
Sbjct: 26117 gccaatggctgcacgtcaggggccagggctactcgggccccctatgcgctatggagaga 26176

Query: 23861 gttcctcttctccgttcccgcggggccccccgcgcagtactcggtgtgtggccctgacct 23920
              ||||||||||||||||||||||||||||||||||||||||||||||||||||||||||
Sbjct: 26177 gttcctcttctccgttcccgcggggccccccgcgcagtactcggtgtgtggccctgacct 26236

Query: 23921 gggtctgttccctgcatctcctcaggccaccttcctgtctgctgcccagggtctggtct 23980
              ||||||||||||||||||||||||||||||||||||||||||||||||||||||||||
Sbjct: 26237 gggtctgttccctgcatctcctcaggccaccttcctgtctgctgcccagggtctggtct 26296
```

Stretch of Exon 10-Homolog 2

```
Query: 23622 aaatcagggccccaacaccctccctcctcacagggaccccggagaacggcagcgagcct 23681
              ||| ||||||||||||||||||||||| ||||||||||||||||||||||||||||||
Sbjct: 65628 gaatgagggccccaacaccctccctcctcgcagggaccccggagaacggcagcgagcct 65687

Query: 23682 gagagcaggtccccggacaacaggacccagctggccccgcgtgcatgccaggggacgc 23741
              ||||||||||||||||||||||||||||||||||||||||||||||||||||||||||
Sbjct: 65688 gagagcaggtccccggacaacaggacccagctggccccgcgtgcatgccaggggacgc 65747

Query: 23742 tggtgccctggagccaacatctgcttgccgctggacgcctcctgccaccccaggcctgc 23801
              |||||||||||||||||||||||||||||||||||||| |||||||||||  |||||||
Sbjct: 65748 tggtgccctggagccaacatctgcttgccgctggacgcctcctgccaccc-aggcctgc 65806

Query: 23802 gccaatggctgcacgtcaggg-ccagggctacccggggcccctatgcgctatggagaga 23860
              |||||||||||||||||||||  |||||||| |||||||||||||||||||||||||||
Sbjct: 65807 gccaatggctgcacgtcaggggccagggctactcgggccccctatgcgctatggagaga 65866

Query: 23861 gttcctcttctccgttcccgcggggccccccgcgcagtactcggtgtgtggccctgacct 23920
              ||||||||||||||||||||||||||||||||||||||||||||||||||||||||||
Sbjct: 65867 gttcctcttctccgttcccgcggggccccccgcgcagtactcggtgtgtggccctgacct 65926

Query: 23921 gggtctgttccctgcatctcctcaggccaccttcctgtctgctgcccagggtctggtct 23980
              ||||||||||||||||||||||||||||||||||||||||||||||||||||||||||
Sbjct: 65927 gggtctgttccctgcatctcctcaggccaccttcctgtctgctgcccagggtctggtct 65986
```

FIG 2 Cont.

Exon 11-Homolog 1

```
Query: 24267 agccctgcgtgtccaccctcatccgtcgtgcggggtccacgggccatgaccgtgaggac 24326
              ||||||||||||||||||||||||||||||| ||||||||||||||||||||||||||||
Sbjct: 26604 agccctgcgtgtccaccctcatccgtcgtgcagggtccacgggccatgaccgtgaggac 26663

Query: 24327 gtgatgcagccctgcctccctctccacaggtcacccctccacggccaggatgtcctcatgc 24386
              |||||||||||||||||||||||||||||||||||||||||| ||||||||||||||||
Sbjct: 26664 gtgatgcagccctgcctccctctccacaggtcacccctccacagccaggatgtcctcatgc 26723

Query: 24387 tccctggtgacctcgttggcttgcagcacgacgctggccctggcgccctcctgcactgct 24446
              ||||||||||||||||||||||||||||||||||||||||||||||||||||||||||||
Sbjct: 26724 tccctggtgacctcgttggcttgcagcacgacgctggccctggcgccctcctgcactgct 26783

XmaI
Query: 24447 cgccggctcccggccaccctggtccccggggcccgtacctctccgccaacgcctcgtcat 24506
              ||||||||||||||||||||||||||| |||||||||||||||||||||||||||||||
Sbjct: 26784 cgccggctcccggccaccctggtccccaggcccgtacctctccgccaacgcctcgtcat 26843

Query: 24507 ggctgccccacttgccagcccagctggagggcacttgggcctgccctgcctgtgccctgc 24566
              ||||||||||||||||||||||||||||||||||||||||||||||||||||||||||||
Sbjct: 26844 ggctgccccacttgccagcccagctggagggcacttgggcctgccctgcctgtgccctgc 26903

Query: 24567 ggctgcttgcagccacggaacagctcaccgtgctgctgggcttgaggcccaaccctggac 24626
              ||||||||||||||||||||||||||||||||||||||||||| |||||||||||||| |
Sbjct: 26904 ggctgcttgcagccacggaacagctcaccgtgctgctgggcctgaggcccaaccctgggc 26963

Query: 24627 tgcggctgcctgggcgctatgaggtccgggcagaggtgggcaatggcgtgtccaggcaca 24686
              ||||||||||||||||||||||||||||||||||||||||||||||||||||||||||||
Sbjct: 26964 tgcggctgcctgggcgctatgaggtccgggcagaggtgggcaatggcgtgtccaggcaca 27023

Query: 24687 acctctcctgcagctttgacgtggtctccccagtggctgggctgcgggtcatctaccctg 24746
              |||| |||||||||||||||||||||||||||||||||||||||||||||||||||||||
Sbjct: 27024 acctgtcctgcagctttgacgtggtctccccagtggctgggctgcgggtcatctaccctg 27083

Query: 24747 cccccgcgacggccgcctctacgtgcccaccaacggctcagccttggtgctccaggtgg 24806
              |||||||||||||||||||||||||||||||||||||||||||| |||||||||||||
Sbjct: 27084 cccccgcgacggccgcctctacgtgcccaccaacggctcagcctggtgctccaggtgg 27143

Query: 24807 actctggtgccaacgccacggccacggctcgctggcctgggggcagtgtcagcgcccgct 24866
              |||||||||| |||||||||||||||||||||||||||||||||||||||||||||||||
Sbjct: 27144 actctggtgccagcgccacggccacggctcgctggcctgggggcagtgtcagcgcccgct 27203

Query: 24867 ttgagaatgtctgccctgccctggtggccaccttcgtgcccggctgcccctgggagacca 24926
              |||||||| ||||||||||||||||||||||||||||||||| ||||||||||||||||
Sbjct: 27204 ttgagaatgcctgccctgccctggtggccaccttcgtgcccagctgcccctgggagacca 27263

Query: 24927 acgataccctgttctcagtggtagcactgccgtggctcagtgagggggagcacgtggtgg 24986
              | |||||||||||||||||||||||||||||||||||||| |||||||||||||| |||
Sbjct: 27264 atgataccctgttctcagtggtagcactgccgtggctcggtgaggggagcacgtgatgg 27323

Query: 24987 acgtggtggtggaaaacagcgccagccgggccaacctcagcctgcgggtgacggcggagg 25046
              |||| |||||||||||||||||||||||||||||||||||||||||||||||||||||||
Sbjct: 27324 acgttgtggtggaaaacagcgccagccgggccaacctcagcctgcgggtgacggcggagg 27383

Query: 25047 agcccatctgtggcctccgcgccacgcccagccccgaggcccgtgtactgcagggagtcc 25106
              ||||||||||||||||||||||||||||||||||||||||||||||||||||||||||||
Sbjct: 27384 agcccatctgtggcctccgcgccacgcccagccccgaggcccgtgtactgcagggagtcc 27443
```

FIG 2 Cont.

```
Query:  25107  tagtggtgagtatggccgaggctccaccaccagccccaggcaggtgcctgcagacaggg  25166
               |      ||||||||||||||||||||||||||||||||||||||||||||||||||||
Sbjct:  27444  ca---gtgagtatggccgaggctccaccaccagccccaggcaggtgcctgcagacaggg  27500

Query:  25167  tgctcacacagggcgtgaggcctggcttcccagtgagggcagcagcccagttactgggga  25226
               ||||||||||||| ||| ||||||||||||||||||||||||||||||||||||||||||
Sbjct:  27501  tgctcacacagggcttgaggcctggcttcccagtgagggcagcagcccagttactgggga  27560
```

Exon 11—Homolog 2

```
Query:  24267  agccctgcgtgtccaccctcatccgtcgtgcgggggtccacgggccatgaccgtgaggac  24326
               |||||||||||||||||||||||||||||||| |||||||||||||||||||||||||||
Sbjct:  66294  agccctgcgtgtccaccctcatccgtcgtgcaggggtccacgggccatgaccgtgaggac  66353

Query:  24327  gtgatgcagccctgcctccctctccacaggtcacctccacggccaggatgtcctcatgc   24386
               |||||||||||||||||||||||||||||||||||||||||||| |||||||||||||||
Sbjct:  66354  gtgatgcagccctgcctccctctccacaggtcacctccacggccaggatgtcctcatgc   66413

Query:  24387  tccctggtgacctcgttggcttgcagcacgacgctggccctggcgcctccgcactgct    24446
               |||||||||||||||||||||||||||||||||||||||||||||||| ||||||||
Sbjct:  66414  tccctggtgacctcgttggcttgcagcacgacgctggccctggcgcctccgcactgct    66473

Query:  24447  cgccggctcccggccaccctggtccccgggccccgtacctctccgccaacgcctcgtcat  24506
               ||||||||||||||||||||||||| |||||||||||||||||||||||||||||||||
Sbjct:  66474  cgccggctcccggccaccctggtccccaggccccgtacctctccgccaacgcctcgtcat  66533

Query:  24507  ggctgccccacttgccagccagctggagggcacttgggcctgcctgcctgtgccctgc    24566
               ||||||||||||||||||||||||||||||||||||||||||||||||||||||||||
Sbjct:  66534  ggctgccccacttgccagccagctggagggcacttgggcctgcctgcctgtgccctgc    66593

Query:  24567  ggctgcttgcagccacggaacagctcaccgtgctgctgggcttgaggcccaaccctggac  24626
               |||||||||||||||||||||||||||||||||||||||||| |||||||||||||| |
Sbjct:  66594  ggctgcttgcagccacggaacagctcaccgtgctgctgggcctgaggcccaaccctgggc  66653

Query:  24627  tgcggctgcctgggcgctatgaggtccgggcagaggtgggcaatggcgtgtccaggcaca  24686
               ||||||||||||||||||||||||||||||||||||||||||||||||||||||||||||
Sbjct:  66654  tgcggctgcctgggcgctatgaggtccgggcagaggtgggcaatggcgtgtccaggcaca  66713

Query:  24687  acctctcctgcagctttgacgtggtctccccagtggctgggctgcgggtcatctaccctg  24746
               ||||  |||||||||||||||||||||||||||||||||||||||||||||||||||||
Sbjct:  66714  acctgtcctgcagctttgacgtggtctccccagtggctgggctgcgggtcatctaccctg  66773

Query:  24747  cccccgcgacggccgcctctacgtgcccaccaacggctcagccttggtgctccaggtgg   24806
               |||||||||||||||||||||||||||||||||||||||||||| |||||||||||||
Sbjct:  66774  cccccgcgacggccgcctctacgtgcccaccaacggctcagcctggtgctccaggtgg   66833

Query:  24807  actctggtgccaacgccacggccacggctcgctggcctggggggcagtgtcagcgcccgct  24866
               ||||||||||||  |||||||||||||||||||||||||||||||||||||||||||||
Sbjct:  66834  actctggtgccagcgccacggccacggctcgctggcctggggggcagtgtcagcgcccgct  66893

Query:  24867  ttgagaatgtctgccctgccctggtggccaccttcgtgcccggctgcccctgggagacca  24926
               |||||||| |||||||||||||||||||||||||||||||||||||||||||||||||||
Sbjct:  66894  ttgagaatgcctgccctgccctggtggccaccttcgtgcccggctgcccctgggagacca  66953
```

FIG 2 Cont.

```
Query: 24927 acgataccctgttctcagtggtagcactgccgtggctcagtgaggggagcacgtggtgg 24986
              | ||||||||||||||||||||||||||||||||||||  |||||||||||||||| |||
Sbjct: 66954 atgataccctgttctcagtggtagcactgccgtggctcggtgaggggagcacgtgatgg 67013

Query: 24987 acgtggtggtggaaaacagcgccagccgggccaacctcagcctgcgggtgacggcggagg 25046
              |||| |||||||||||||||||||||||||||||||||||||||| |||||||||||||
Sbjct: 67014 acgttgtggtggaaaacagcgccagccgggccaacctcagcctgcgggtgacggcggagg 67073

Query: 25047 agcccatctgtggcctccgcgccacgcccagccccgaggcccgtgtactgcagggagtcc 25106
              |||||||||||||||||||||||||||||||||||||||||||||||||||||||||||
Sbjct: 67074 agcccatctgtggcctccgcgccacgcccagccccgaggcccgtgtactgcaggagtcc 67133

Query: 25107 tagtggtgagtatggccgaggctccaccaccagcccccaggcaggtgcctgcagacaggg 25166
              ||||||||||||||||||||||||||||||||||||||||||||||||||||||||||
Sbjct: 67134 cagtggtgagtatggccgaggctccaccaccagcccccaggcaggtgcctgcagacaggg 67193

Query: 25167 tgctcacacagggcgtgaggcctggcttcccagtgagggcagcagcccagttactgggga 25226
              ||||||||||||||||||||||||||||||||||||||||||||||||||||||||||||
Sbjct: 67194 tgctcacacagggcgtgaggcctggcttcccagtgagggcagcagcccagttactgggga 67253
```

FIG 2 Cont.

Exon 15-Homolog 1

```
Query:  27279  tgggaccettaaggctgggccgcaggtgcagccgttcaccccgggctcctcaggcggggg  27338
               ||||||||||||||||||||||||||||||||||||||||||||||||||||||||||||
Sbjct:  29661  tgggaccettaaggctgggccgcaggtgcagccgttcaccccgggctcctcaggcggggg  29720

Query:  27339  gcttctgccgagcgggtggggagcaggtgggggtgccgcggctgccccactcgggcctgt  27398
               ||||||||  |||||||||||||||||||||||||||||||||||||||  ||||||||
Sbjct:  29721  gcttctgctgagcgggtggggagcaggtgggggtgccgcggctgccccacttgggcctgt  29780

Query:  27399  ccccacaggtgagtacctcctgaccgtgctggcatctaatgccttcgagaaccggacgca  27458
               |||||||||||||| |||||||||||||||||||||||||||||||||||||||||||||
Sbjct:  29781  ccccacaggtgagtacgtcctgaccgtgctggcatctaatgccttcgagaaccggacgca  29840

Query:  27459  gcaggtgcctgtgagcgtgcgcgcctccctgccctccgtg  27498
               |||||||||||||||||||| ||||||||||||||| |||
Sbjct:  29841  gcaggtgcctgtgagcgtgtgcgcctccctgccctctgtg  29880
```

Exon 15-Homolog 2

```
Query:  27279  tgggaccettaaggctgggccgcaggtgcagccgttcaccccgggctcctcaggcggggg  27338
               ||||||||||||||||||||||||||||||||||||||||||||||||||||||||||||
Sbjct:  69326  tgggaccettaaggctgggccgcaggtgcagccgttcaccccgggctcctcaggcggggg  69385

Query:  27339  gcttctgccgagcgggtggggagcaggtgggggtgccgcggctgccccactcgggcctgt  27398
               ||||||||||||||||||||||||||||||||||||||||||||||||  ||||||||
Sbjct:  69386  gcttctgccgagcgggtggggagcaggtgggggtgccgcggctgccccacttgggcctgt  69445

Query:  27399  ccccacaggtgagtacctcctgaccgtgctggcatctaatgccttcgagaaccggacgca  27458
               |||||||||||||| |||||||||||||||||||||||||||||||||||||||||||||
Sbjct:  69446  ccccacaggtgagtacgtcctgaccgtgctggcatctaatgccttcgagaaccggacgca  69505

Query:  27459  gcaggtgcctgtgagcgtgcgcgcctccctgccctccgtggctgtgggtgtgagtgacgg  27518
               ||||||||||||||||||||||||||||||||||||| ||||||||||||||||||||||
Sbjct:  69506  gcaggtgcctgtgagcgtgcgcgcctccctgccctccgaggctgtgggtgtgagtgacgg  69565

Query:  27519  cgtcctggtggccggccggcccgtcaccttctaccgcacccgctgccctcgcctggggg  27578
               |||||||||||||||||||||||||||||||||||||||| | |||||||||||||||||
Sbjct:  69566  cgtcctggtggccggccggcccgtcaccttctaccgcatctgctgccctcgcctggggg  69625

Query:  27579  tgttctttacacgtgggacttcggggacggctcccctgtcctgacccagagccagccggc  27638
               ||||||||||||||||||||||||||||||||||||||||||||||||||||||||||||
Sbjct:  69626  tgttctttacacgtgggacttcggggacggctcccctgtcctgacccagagccagccggc  69685

Query:  27639  tgccaaccacacctatgcctcgaggggcacctaccacgtgcgcctggaggtcaacaacac  27698
               |||||||||||||||| ||||||||||| |||||||||||||||||||||||||||||||
Sbjct:  69686  tgccaaccacacctatccctcgagggcatctaccacgtgcgcctggaggtcaacaacac  69745

Query:  27699  ggtgagcggtgcggcggcccaggcggatgtgcgcgtctttgaggagctccgcggactcag  27758
               ||||||||||||||||||||||||||||||||||||||||||||||||||||||| |||
Sbjct:  69746  ggtgagcggtgcggcggcccaggcggatgtgcgcgtctttgaggagctccgcgggctcag  69805

Query:  27759  cgtggacatgagcctggccgtggagcagggcgcccccgtggtggtcagcgccgcggtgca  27818
```

FIG 2 Cont.

```
                 ||||||||||||||||||||||||||||||||||||||||||||||  ||||||||||
Sbjct: 69806 cgtggacatgagcctggccgtggagcagggcgccccgtggtggtcagtgccgcggtgca 69865

Query: 27819 gacgggcgacaacatcacgtggaccttcgacatgggggacggcaccgtgctgtcgggccc 27878
             ||||||||||||||||||||||||||||||||||||||||||||||||||||||||||||
Sbjct: 69866 gacgggcgacaacatcacgtggaccttcgacatgggggacggcaccgtgctgtcgggccc 69925

Query: 27879 ggaggcaacagtggagcatgtgtacctgcgggcacagaactgcacagtgaccgtgggtgc 27938
             ||||| ||||||||||||||||||||||||||||||||||||| | ||||||||||||||
Sbjct: 69926 agaggccacagtggagcatgtgtacctgcgggcacagaactgcacagtgaccgtgggtgc 69985

Query: 27939 ggccagcccgccggccacctggcccggagcctgcacgtgctggtcttcgtcctggaggt 27998
             ||||||||||||||||||||||||||||||||||||||||||||||||||||||||||
Sbjct: 69986 ggccagcccgccggccacctggcccggagcctgcacgtgctggtcttcgtcctggaggt 70045

Query: 27999 gctgcgcgttgaacccgccgcctgcatccccacgcagcctgacgcgcggctcacggccta 28058
             |||||||| || |||||||||||||||||||| ||||||||||||||||||||||||||
Sbjct: 70046 gctgcgcgtcgagcccgccgcctgcatccccactcagcctgacgcgcggctcacggccta 70105

Query: 28059 cgtcaccgggaacccggcccactacctcttcgactggaccttcggggatggctcctccaa 28118
             |||||||||||||||||||||| |||||||||||||||||| |||||||||||||||||
Sbjct: 70106 cgtcaccgggaacccggcccgctacctcttcgactggaccttttggggatggctcctccaa 70165

MluI
Query: 28119 cacgaccgtgcgggggtgcccgacggtgacacacaacttcacgcggagcggcacgttccc 28178
             |||||| |||||||||||||||||||||||||||||||||||| || ||||||||||||
Sbjct: 70166 cacgaccatgcgggggtgcccgacggtgacacacaacttcacgcgtagcggcacgttccc 70225

Query: 28179 cctggcgctggtgctgtccagccgcgtgaacagggcgcattacttcaccagcatctgcgt 28238
             ||||||||||||||||||||||||||||||||||||||| ||||||||||||||||| |
Sbjct: 70226 cctggcgctggtgctgtccagccgcgtgaacagggcgcgttacttcaccagcatctgcgt 70285

Query: 28239 ggagccagaggtgggcaacgtcaccctgcagccagagaggcagtttgtgcagctcgggga 28298
             ||||||||||||||||||||||||||||||||||||||||||||||||||||||||||||
Sbjct: 70286 ggagccagaggtgggcaacgtcaccctgcagccagagaggcagtttgtgcagctcgggga 70345

Query: 28299 cgaggcctggctggtggcatgtgcctggcccccgttcccctaccgctacacctggactt 28358
             ||||||| ||||||||||||||||||||||||||||||||||||||||||||||||||
Sbjct: 70346 cgaggccggctggtggcatgtgcctggcccccgttcccctaccgctacacctggactt 70405

Query: 28359 tggcaccgaggaagccgcccccacccgtgccaggggccctgaggtgacgttcatctaccg 28418
             |||||||| |||||| |||| |||| ||| | ||||||||||||||||||||||||||
Sbjct: 70406 tggcaccgaagaagccgtccccgcccgtgtcgggggccctgaggtgacgttcatctaccg 70465

Query: 28419 agacccaggctcctatcttgtgacagtcaccgcgtccaacaacatctctgctgccaatga 28478
             |||||||||||||||||||||||||||||||||||||||||||||||| |||||||||
Sbjct: 70466 agacccaggctcctatcttgtgacagtcaccgcgtccaacaacatctccgctgccaatga 70525

Query: 28479 ctcagccctggtggaggtgcaggagcccgtgctggtcaccagcatcaaggtcaatggctc 28538
             |||||||||||||||||||||||||||| |||||||||||||||||||||||||||||
Sbjct: 70526 ctcagccctggtggaggtgcaggagcccatgctggtcaccagcatcaaggtcaatggctc 70585

Query: 28539 ccttgggctggagctgcagcagccgtacctgttctctgctgtgggccgtgggcgcccgc 28598
             ||||||||||||||||| ||||||||||||||||||||||||||||||||||||||||
Sbjct: 70586 ccttgggctggagctgcagtagccgtacctgttctctgctgtgggccgtgggcgcccgc 70645

Query: 28599 cagctacctgtgggatctgggggacggtgggtggctcgagggtccggaggtcaccacgc 28658
             |||||||||||||||||||||||||||||||| |||||||||||||||||||||||||
```

FIG 2 Cont.

```
Sbjct:  70646 cagctacctgtgggatctgggggacggtgggcggctcgagggtccggaggtcacccacgc 70705

Query:  28659 ttacaacagcacaggtgacttcaccgttagg-tggccggctggaatgaggtgagccgcag 28717
              ||||||||||||||||||||||||||||||| ||||||||| ||||||||||||||||||
Sbjct:  70706 ttacaacagcacaggtgacttcaccgttagggtggccggctgaatgaggtgagccgcag 70765

Query:  28718 cgaggcctggctcaatgtgacggtgaagcggcgcgtgcgggggctcgtcgtcaatgcaag 28777
              |||||||||||||||||||||||||||||||||||||||||||| ||||||||| ||
Sbjct:  70766 cgaggcctggctcaatgtgacggtgaagcggcgcgtgcgggggctcatcgtcaatgcag 70825

Query:  28778 cccacggtggtgcccctgaatgggagcgtgagcttcagcacgtcgctggaggccggcag 28837
              |  ||||||||||||||||||||||| ||||||||| ||||| |||||||||||||||
Sbjct:  70826 ctgcacggtggtgcccctgaatgggagcatgagcttcagcacctcgctggaggccggcag 70885

Query:  28838 tgatgtgcgctattcctgggtgctctgtgaccgctgcacgcccatcctgggggtcctac 28897
              ||||||||||||||||||||||||||||||||||||||||||||| |||||||||||| |
Sbjct:  70886 tgatgtgcgctattcctgggtgctctgtgaccgctgcacgcccatctctgggggtcctgc 70945

Query:  28898 catctctt-acaccttccgctccgtgggcaccttcaatatcatcgtcacggctgagaacg 28956
              ||||||||  |||||||||||||||||||||||||||||||||||||||| |||||||||
Sbjct:  70946 catctctttacaccttccgctccgtgggcaccttcaatatcatcgtcacagctgagaacg 71005

Query:  28957 aggtgggctccgcccaggacagcatcttcgtctatgtcctgcagctcatagagggggctgc 29016
              ||||||||||||||||||||||||||||||||||||||||||||||||||||||||||||
Sbjct:  71006 aggtgggctccgcccaggacagcatcttcgtctatgtcctgcagctcatagagggggctgc 71065

Query:  29017 aggtggtgggcggtggccgctacttcccccaccaaccacacggtacagctgcaggccgtgg 29076
              ||||||||||||||||||||||||||||||||||||||||||||||||||||||||||||
Sbjct:  71066 aggtggtgggcggtggccgctacttcccccaccaaccacacggtacagctgcaggccgtgg 71125

Query:  29077 ttagggatggcaccaacgtctcctacagctggactgcctggagggacaggggcccggccc 29136
              | |||||||||||||||| |||   |||||||||||||||||||||||||||||||||||
Sbjct:  71126 tcagggatggcaccaacatct---acagctggactgcctggagggacaggggcccggccc 71182

Query:  29137 tggccggcagcggcaaaggcttctcgctcacggt-ctcgaggccggcacctaccatgtgc 29195
              |||||||||||||||||||||||||||||||||| ||||||||||||||||||||||||
Sbjct:  71183 tggccggcagcggcaaaggcttctcgctcactgcgctcgaggccggcacctaccatgtgc 71242

Query:  29196 agctgcgggccaccaacatgctgggcagcgcctgggccgactgcaccatggacttcgtgg 29255
              ||||||||||||||||||||||||||||||||||||||  ||||||| ||||||||||||
Sbjct:  71243 agctgcgggccaccaacatgctgggcagcgcctgggctgactgcaccgtggacttcgtgg 71302

Query:  29256 agcctgtggggtggctgatggtggccgcctccccgaacccagctgccgtcaacaaaagcg 29315
              |||||||||||||||||||||||||||||||||||||||||||||||||||| ||| || |
Sbjct:  71303 agcctgtggggtggctgatggtggccgcctccccgaacccagctgccgtcaacacaagtg 71362

Query:  29316 tcaccctcagtgccgagctggctggtggcagtggtgtcgtatacacttggtccttggagg 29375
              ||||||||||||||||||||||||||||||||||||||||||||||||||||||||||||
Sbjct:  71363 tcaccctcagtgccgagctggctggtggcagtggtgtcgtatacacttggtccttggagg 71422

Query:  29376 aggggctgagctgggagacctccgagccatttaccacccatagcttccccacacccggcc 29435
              |||||||||||||||||||| |||||||||||||||||||| ||||||||||||||||||
Sbjct:  71423 aggggctgagctgggagaccccgagccatttaccacccacagcttccccacacccggcc 71482

Query:  29436 tgcacttggtcaccatgacggcagggaacccgctgggctcagccaacgccaccgtggaag 29495
              ||||||||||||||||||||||||||||||||||||||||||||||||||||||||||||
Sbjct:  71483 tgcacttggtcaccatgacggcagggaacccgctgggctcagccaacgccaccgtggaag 71542
```

FIG 2 Cont.

```
Query: 29496 tggatgtgcaggtgcctgtgagtggcctcagcatcagggccagcgagccggaggcagct 29555
              ||||||||||||||||||||||||||||||||||||||||||||||| ||||||||||
Sbjct: 71543 tggatgtgcaggtgcctgtgagtggcctcagcatcagggccagcgagccgggaggcagct 71602

Query: 29556 tcgtggcggccgggtcctctgtgcccttttgggggcagctggccacgggcaccaatgtga 29615
              ||||||||||||||||||||||||||||||||||||||||||||||||||||||||||||
Sbjct: 71603 tcgtggcggccgggtcctctgtgcccttttgggggcagctggccacgggcaccaatgtga 71662

Query: 29616 gctggtgctgggctgtgcccggcggcagcagcaagcgtggccctcatgtcaccatggtct 29675
              ||||||||||||||||||||||||||||||||||||||||||||||||||||||||||||
Sbjct: 71663 gctggtgctgggctgtgcccggcggcagcagcaagcgtggccctcatgtcaccatggtct 71722

Query: 29676 tcccggatgctggcaccttctccatccggctcaatgcctccaacgcagtcagctgggtct 29735
              |||||||||||||||||| |||||||||||||||||||||||||||||||||||||||||
Sbjct: 71723 tcccggatgctggcaccttcaacatccggctcaatgcctccaacgcagtcagctgggtct 71782

Query: 29736 cagccacgtacaacctcacggcggaggagcccatcgtgggcctggtgctgtgggccagca 29795
              ||||||||||||||||||||| ||||||||||||||||||||||||||||||||||||||
Sbjct: 71783 cagccacgtacaacctcacggtggaggagcccatcgtgggcctggtgctgtgggccagca 71842

Query: 29796 gcaaggtggtggcgcccgggcagctggtccattttcagatcctgctggctgccggctcag 29855
              ||||||||||||||||||||||||| ||||||||||||||||||||||||||||||||||
Sbjct: 71843 gcaaggtggtggcgcccgggcagcttgtccattttcagatcctgctggctgccggctcag 71902

PstI                 XmaI
Query: 29856 ctgtcaccttccgcctgcaggtcggcggggccaaccccgaggtgctccccgggccccgtt 29915
              ||||||||||||| |||||||||||||||||| |||||| |||||||| |||||||||
Sbjct: 71903 ctgtcaccttccgccggcaggtcggcggggccagccccgaagtgctccctgggccccgtt 71962

Query: 29916 tctcccacagcttcccccgcgtcggagaccacgtggtgagcgtgcggggcaaaaaccacg 29975
              ||||||||||||||||||||| |||||||||||||||||||||||| | |||||||||
Sbjct: 71963 tctcccacagcttcccccgcatcggagaccacgtggtgagcgtgcagagcaaaaaccacg 72022

Query: 29976 tgagctgggcccaggcgcaggtgcgcatcgtggtgctggaggccgtgagtgggctgcagg 30035
              |||||||||||||||||||||||||||||||||||||||||||||||||| |||||||||
Sbjct: 72023 tgagctgggcccaggcgcaggtgcgcatcgtggtgctggaggccgtgagcgggctgcagg 72082

Query: 30036 tgcccaactgctgcgagcctggcatcgccacgggcactgagaggaacttcacagcccgcg 30095
              ||||||||||| |||||||||||||||||| ||||||||||||||||||||||||||||
Sbjct: 72083 tgcccaactgctgtgagcctggcatcgccatgggcactgagaggaacttcacagcccgcg 72142

Query: 30096 tgcagcgcggctctcgggtcgcctacgcctggtacttctcgctgcagaaggtccagggcg 30155
              |||||||||||||||||||||||||||||||||||  ||||||||||||||||| |||
Sbjct: 72143 tgcagcgcggctctcgggtcgcctacgcctggtatttctcgctgcagaaggtccggggcg 72202

Query: 30156 actcgctggtcatcctgtcgggccgcgacgtcacctacacgcccgtggccgcggggctgt 30215
              |||  || ||||||||||||||||||||||||||||||||||||| ||||||||||||||
Sbjct: 72203 actctctgttcatcctgtcgggccgcgacgtcacctacacgcc-gtggccgcggggctgt 72261

BssHII
Query: 30216 tggagatccaggtgcgcgccttcaacgccctgggcagtgagaaccgcacgctggtgctgg 30275
              ||||||||||||| ||||||||||||||||||||||||||||||||||||||||||||||
Sbjct: 72262 tggagatccaggtgcgtgccttcaacgccctgggcagtgagaaccgcacgctggtgctgg 72321

PstI
Query: 30276 aggttcaggacgccgtccagtatgtggccctgcagagcggcccctgcttcaccaaccgct 30335
              |||||||||||||||||||||||||||||||||| |||||||||||||||||||||||||
Sbjct: 72322 aggttcaggacgccgtccagtatgtggccctgcggagcggcccctgcttcaccaaccgct 72381
```

FIG 2 Cont.

```
Query: 30336 cggcgcagtttgaggccgccaccagccccagccccggcgtgtggcctaccactgggact 30395
              |||||||||||||||||||||||||||||||||||||| |||||||||||||||||||
Sbjct: 72382 tggcgcagtttgaggccgccaccagccccagccccggcgcgtggcctaccactgggact 72441

Query: 30396 ttggggatgggtcgccagggcaggacacagatgagcccagggccgagcactcctacctga 30455
              |||||||||||| ||||||||||||||||||| ||||||||||||||||||||||||||
Sbjct: 72442 ttggggatgggtccccagggcaggacacagataagcccagggccgagcactcctacctga 72501

Query: 30456 ggcctggggactaccgcgtgcaggtgaacgcctccaacctggtgagcttcttcgtggcgc 30515
              |||||||||||||||||||||||||||||||||||||||||||||||| |||||||||
Sbjct: 72502 ggcctggggactaccgcgtgcaggtgaacgcctccaacctggtgagctttttcgtggcgc 72561

Query: 30516 aggccacggtgaccgtccaggtgctggcctgccgggagccggaggtggacgtggtcctgc 30575
              |||||||||||||||||||||||||||||||||||||||||||||||||||||||||||
Sbjct: 72562 aggccacggtgaccgtccaggtgctggcctgccgggagccggaggtggacgtggtcctgc 72621

Query: 30576 ccctgcaggtgctgatgcggcgatcacagcgcaactacttggaggcccacgttgacctgc 30635
              |||||||||||||||||||| |||||||||||||||| |||| ||| ||||||||||||
Sbjct: 72622 ccctgcaggtgctgatgcgacgatcacagcgcaactgctggatgcctacgttgacctgc 72681

Query: 30636 gcgactgcgtcacctaccagactgagtaccgctgggaggtgtatcgcaccgccagctgcc 30695
              ||||||| ||||||||||||||||||||||||||||||||| |||||||||||||||||
Sbjct: 72682 gcgactgtgtcacctaccagactgagtaccgctgggaggtgtaccgcaccgccagctgcc 72741

Query: 30696 agcggccggggcgcccagcgcgtgtggccctgcccggcgtggacgtgagccggcctcggc 30755
              |||||||||| |||| ||||||||||||||||||||||||||||||||||||||||| |
Sbjct: 72742 agcggccggggtgcccggcgcgtgtggccctgcccggcgtggacgtgagccggcctcagc 72801

Query: 30756 tggtgctgccgcggctggcgctgcctgtggggcactactgctttgtgtttgtcgtgtcat 30815
              |||||||||||||||||||||||||||||||||||||||||||||||||||||||||||
Sbjct: 72802 tggtgctgccgcggctggcgctgcctgtggggcactactgctttgtgtttgtcgtgtcat 72861

Query: 30816 ttggggacacgccactgacacagagcatccaggccaatgtgacggtggccccgagcgcc 30875
              |||||||||||||||| ||| |||||||||||||||||||||||||||||||||||||
Sbjct: 72862 ttggggacacgccactggcacggagcatccaggccaatgtgacggtggccccgagcgcc 72921

Query: 30876 tggtgcccatcattgagggtggctcataccgcgtgtggtcagacacacgggacctggtgc 30935
              |||||||||||| ||||||||||||| ||||||||||||||||||||| |||||||||
Sbjct: 72922 tggtgcccatcactgagggtggctcctaccgcgtgtggtcagacacacaggacctggtgc 72981

Query: 30936 tggatgggagcgagtcctacgaccccaacctggaggacggcgaccagacgccgctcagtt 30995
              |||||||||||||||||||||||||||||||||||||||| ||||||||||||||||||
Sbjct: 72982 tggatgggagcgagtcctacgaccccaacctggaggacggcgaccagacgccgctcagtt 73041

Query: 30996 tccactgggcctgtgtggcttcgacacaggtcagtgcgtggcagggccgtcctccatgcc 31055
              |||  ||||||||||||||||||||||||||||||||||||||||||||||||| ||||
Sbjct: 73042 tccagtgggcctgtgtggcttcgacacaggtcagtgcgtggcagggccgtcctccctgcc 73101

Query: 31056 cctcacccgtccacacccatgagcccagagaacacccagcttgccaccagggctggcccg 31115
              ||||||||||||||||||||||||||||||||||||||||||||||||||||||||||
Sbjct: 73102 cctcacccgtccacacccatgagcccagagaacacccagcttgccaccagggctggcccg 73161
```

FIG 2 Cont.

Exon 16—Homolog 2

```
Query: 31176 gggccgggctctgctttaaaactggatggggctctcaggccacgtcgcccttgttctcg 31235
              |||||||||||||||||||||||||||||| |||| ||||||||||||||||||||||
Sbjct: 73222 gggccgggctctgctttaaaactggatgggGttctcgggccacgtcgcccttgttctcg 73281

Query: 31236 gcctgcagagggaggctggcgggtgtgcgctgaactttgggccccgcgggagcagcacgg 31295
              ||||||||||||||||||||||||||||||||||||||||||||||||||||||||||||
Sbjct: 73282 gcctgcagagggaggctggcgggtgtgcgctgaactttgggccccgcgggagcagcacgg 73341

Query: 31296 tcaccattccacgggagcggctggcggctggcgtggagtacaccttcagcctgaccgtgt 31355
              ||||||||||||||| ||||||| |||||||||||||||||||||||| |||||
Sbjct: 73342 tcaccattccacgggaacggctggcagctggcgtggagtacaccttcagcctcaccgtgt 73401
                                                 PvuII Query: 31356 ggaaggccggccgcaaggaggaggccaccaaccagacggtgggtgccgcccgcccctcgg 31415
              ||||||||||||||||||||||||||||||||||||||||||||||||||||||||||||
Sbjct: 73402 ggaaggccggccgcaaggaggaggccaccaaccagacggtgggtgccgcccgcccctcgg 73461
```

FIG 2 Cont.

Exon 20-Homolog 1

```
Query: 33189 agccaggccgtgggagggcgcccccgagactgccacctgctcaccaccc-ctctgctcg 33247
              |||||||||||||||||||||||||||||||||||||||||||||||| ||||||||
Sbjct: 31282 agccaggccgtgggagggcgcccccgagactgccacctgctcaccacccgctctgctcg 31341

Query: 33248 taggtctttggccatcaccctcccagagcccaacggcagcgcaacggggctcacagtctg 33307
              |||||| |||||||||||||||||||||||||||||||||| ||||||| ||||||||||
Sbjct: 31342 taggtctctggccatcaccctcccagagcccaacggcagcgcaatggggctcacagtctg 31401

Query: 33308 gctgcacgggctcaccgctagtgtgctcccagggctgctgcggcaggccgatccccagca 33367
              ||||||||||||||||||||||||||||| |||||||||||||||||||||||||||||
Sbjct: 31402 gctgcacgggctcaccgctagtgtgctcccggggctgctgcggcaggccgatccccagct 31461
                                          XmaI Query: 33368 cgtcatcgagtactcgttggccctggtcacgtgctgaacgaggtgagtgcagcctggga 33427
              |||||||||||||| |||||||||||||||| |||||||||||||||||||||||||
Sbjct: 31462 cgtcatcgagtactcgctggccctggtcactgtgctgaacgaggtgagtgcagcctggga 31521

AatII
Query: 33428 ggggacgtcacatctgctgcatgcgtgcttgggaccaagacctgtaccctgcctggagc 33487
              ||||||  ||||||||||||||||||||| ||||||||||||| ||| ||||||||||
Sbjct: 31522 ggggacctcacatctgctgcatgcgtgctggggaccaagacctgttccctgcctggagc 31581
```

Exon 20-Homolog 2

```
Query: 33216 gactgccacctgctcacca-cccctctgctcgtaggtctttggccatcaccctcccaga 33274
              |||||||||||||||||| |||||||||||||||| |||||||||||||||||||||
Sbjct: 75262 gactgccacctgctcaccacccctctgctcgtaggtctctggccatcaccctcccaga 75321

Query: 33275 gcccaacggcagcgcaacggggctcacagtctggctgcacgggctcaccgctagtgtgct 33334
              |||||||||||||||| ||||||||||||||||| ||||| ||||||| |||||||||
Sbjct: 75322 gcccaacggcagcgcaatggggctcacagtctggctgcaccggctcaccgctagtgtgct 75381

Query: 33335 cccagggctgctgcggcaggccgatccccagcacgtcatcgagtactcgttggccctggt 33394
              ||| ||||||||||||||||||||||||||||||||||||||||||||| |||||||||
Sbjct: 75382 cccggggctgctgcggcaggccgatccccagcacgtcatcgagtactcgctggccctggt 75441

Query: 33395 cacggtgctgaacgaggtgagtgcagcctgggaggggacgtcacatctgctgcatgcgtg 33454
              ||| |||||||||||||||||||||||||||||||||||  |||||||||||||||||
Sbjct: 75442 cactgtgctgaacgaggtgagtgcagcctgggaggggacctcacatctgctgcatgcgtg 75501
```

FIG 2 Cont.

Exon 22—Homolog 1

```
Query: 36719 atgtgaagaggtgccttgtgtggtcggtgggctgcatcacgtggtccccaggtggaggcc 36778
              ||||||||||||||||||||||||||||||||||||||||||||| ||||||||
Sbjct: 32576 atgtgaagaggtgccttgtgtggtcggtgggctgcatcacgtggtccccaagtggaggcc 32635

Query: 36779 ctgggtcatgcagagccacagaaaatgcttagtgaggaggctgtgggggtccagtcaagt 36838
              ||  ||||||||||||||||||||||||||||||||||||| |||||||||||||||||
Sbjct: 32636 ctcggtcatgcagagccacagaaaatgcttagtgaggagactgtgggggtccagtcaagt 32695

Query: 36839 gggctctccagctgcagggctgggggtgggagccaggtgaggacccgtgtagagaggagg 36898
              ||||| ||||||||||||||||| || |||||||||||||||||||||||||||||||
Sbjct: 32696 gggctctccagctgcagggctggaggtgggagccaggtgaggacccgtgtagagaggagg 32755

Query: 36899 gcgtgtgcaaggagtggggccaggagcggggctggacactgctggctccacacagggggcc 36958
              ||||||||||||||||||||||||||||||||||||||||||||||||||||||||||
Sbjct: 32756 gcgtgtgcaaggagtggggccaggagcggggctggacactgctggctccacacagggggcc 32815

Query: 36959 cagcagggagctcgtatgccgctcgtgcctgaagcagacgctgcacaagctggaggccat 37018
              ||||||||||||||||||||||||||||||||||||||||||||||||||||||||||
Sbjct: 32816 cagcagggagctcgtatgccgctcgtgcctgaagcagacgctgcacaagctggaggccat 32875

Query: 37019 gatgctcatcctgcaggcagagaccaccgcgggcaccgtgacgcccaccgccatcggaga 37078
              |||| ||||||||||||||||||||||||||||||||||||||||||||||||||||||
Sbjct: 32876 gatgcgcatcctgcaggcagagaccaccgcgggcaccgtgacgcccaccgccatcggaga 32935
                   FspI
                                                      NlaIII
Query: 37079 cagcatcctcaacatcacaggtgccgcggcccgtgccccatgccacccgcccgcccc 37135
              |||||||||||||||||||||||||||||||||||||||| |||||||||||||||
Sbjct: 32936 cagcatcctcaacatcacaggtgccgcggcccgtgccccacgccacccgcccgcccc 32992
```

FIG 2 Cont.

Exon 22—Homolog 2

```
Query: 36719 atgtgaagaggtgccttgtgtggtcggtgggctgcatcacgtggtccccaggtggaggcc 36778
              |||||||||||||||||||||||| ||||||||||||||| ||||||||||||||||||
Sbjct: 75778 atgtgaagaggtgccttgtgtggtcagtgggctgcatcacgtgttccccaggtggaggcc 75837

Query: 36779 ctgggtcatgcagagccacagaaaatgcttagtgaggaggctgtgggggtccagtcaagt 36838
              ||||||||||||||||||||||| |||||||||||||||||||||||||||||||||||
Sbjct: 75838 ctgggtcatgcagagccacaaaaaatgcttagtgaggaggctgtgggggtccagtcaagt 75897

Query: 36839 gggctctccagctgcagggctgggggtgggagccaggtgaggacccgtgtagagaggagg 36898
              ||||||||||||||||||||||||||||||||||||||||||||||||||||||||||||
Sbjct: 75898 gggctctccagctgcagggctgggggtgggagccaggtgaggacccgtgtagagaggagg 75957

Query: 36899 gcgtgtgcaaggagtggggccaggagcgggctggacactgctggctccacacaggggcc 36958
              ||||||||||||||||||||||||||||||||||||||||||||||||||||||||||
Sbjct: 75958 gcgtgtgcaaggagtggggccaggagcgggctggacactgctggctccacacaggggcc 76017

Query: 36959 cagcagggagctcgtatgccgctcgtgcctgaagcagacgctgcacaagctggaggccat 37018
              ||||||||||||||||||||||||||||||||||||||||||||||||||||||||||||
Sbjct: 76018 cagcagggagctcgtatgccgctcgtgcctgaagcagacgctgcacaagctggaggccat 76077

Query: 37019 gatgctcatcctgcaggcagagaccaccgcgggcaccgtgacgcccaccgccatcggaga 37078
              |||||  |||||||||||||||||||||||||||||||||||||||||||||||||||||
Sbjct: 76078 gatgcgcatcctgcaggcagagaccaccgcgggcaccgtgacgcccaccgccatcggaga 76137

Query: 37079 cagcatcctcaacatcacaggtgccgcggcccgtgcccatgccacccgccgcccc 37135
              ||||||||||||||||||||||||||||||||||||||| |||||||||||||||
Sbjct: 76138 cagcatcctcaacatcacaggtgccgcggcccgtgcccacgccacccgccgcccc 76194
```

FIG 2 Cont.

Exon 23-Homolog 1

```
Query: 37663 cctccctgtctctgcactgacctcacgcatgtctgcaggagacctcatccacctggccag 37722
              ||||||||||||||||||||||||||| ||||||||||||||||||||||||||||||||
Sbjct: 33404 cctccctgtctctgcactgacctcacgcctgtctgcaggagacctcatccacctggccag 33463

Query: 37723 ctcggacgtgcgggcaccacagccctcagagctgggagccgagtcaccatctcggatggt 37782
              ||| |||||||||||||||||||| ||||||||||||||||||||||||||||| |||||||
Sbjct: 33464 ctcagacgtgcgggcaccacagcgctcagagctgggagccgagtcaccatcgcggatggt 33523

Query: 37783 ggcgtcccaggcctacaacctgacctctgccctcatgcgcatcctcatgcgctcccgcgt 37842
              |||||||||||||||||||||||||||||||||||||| || |||| ||| ||||||||||
Sbjct: 33524 ggcgtcccaggcctacaacctgacctctgccctcacgcccatcgtcacgcgctcccgcgt 33583

Query: 37843 gctcaacgaggagcccctgacgctggcgggcgaggagatcgtggcccagggcaagcgctc 37902
              |||||||||||||||||||||||||||||||| |||||||||||||||||||||||||||
Sbjct: 33584 gctcaacgaggagcccctgacgctggcgggtgaggagatcgtggcccagggcaagcgctc 33643

Query: 37903 ggacccgcggagcctgctgtgctatggcggcgcccagggcctggctgccacttctccat 37962
              ||||||||||||||||||||||||||||| |||||||||||||||||||||||||||||||||
Sbjct: 33644 ggacccgcggagcctgctgtgctatggcggcgcccagggcctggctgccacttctccat 33703

Mscl
Query: 37963 ccccgaggctttcagcggggccctggccaacctcagtgacgtggtgcagctcatctttct 38022
              |||| |||||||||| |||||| ||||||||||||||||||||||||||||||||||||||
Sbjct: 33704 cccctaggctttcagcagggcccgggccaacctcagtgacgtggtgcagctcatctttct 33763

Query: 38023 ggtggactccaatccctttcctttggctatatcagcaactacaccgtctccaccaaggt 38082
              |||||||||||||||||||||||||||||||||||||||||||||||||||||||||||||
Sbjct: 33764 ggtggactccaatccctttcctttggctatatcagcaactacaccgtctccaccaaggt 33823

Query: 38083 ggcctcgatggcattccagacacaggccggcgcccagatccccatcgagcggctggcctc 38142
              |||||||||| ||||||||||||||||||||||||||||||||||||||||||||||||||
Sbjct: 33824 ggcctcgatggcgttccagacacaggccggcgcccagatccccatcgagcggctggcctc 33883

Query: 38143 agagcgcgccatcaccgtgaaggtgcccaacaactcggactggctgcccgggccaccg 38202
              ||||||||| ||||||||||||||||||||||||||||||||||||||||||||||||||
Sbjct: 33884 agagcgcgcc-tcaccgtgaaggtgcccaacaactcggactggctgcccgggccaccg 33942

Query: 38203 cagctccgccaactccgccaactccgttgtggtccagcccaggcctccgtcggtgctgt 38262
              |||||||||||||        ||||||||||||||||||||||||||||||||||||||
Sbjct: 33943 cagctccgccaact---------ccgttgtggtccagcccaggcctccgtcggtgctgt 33993

Query: 38263 ggtcaccctggacagcagcaaccctgcggccggctgcatctgcagctcaactatacgct 38322
              |||||||||||||||||||||||||||| |||||||||||||||||||||||||||||||
Sbjct: 33994 ggtcaccctggacagcagcaaccctgcggccgtgctgcatctgcagctcaactatacgct 34053

Query: 38323 gctggacggtgcgtgcagcgggtggggcacacgcggcccctggccttgttcttggggg 38382
              ||||||||||| |||||| ||||||||||||||||||||||||||||||||||||||||
Sbjct: 34054 gctggacggtgcatgcagcggttggggcacacgcggcccctggccttgttcttggggg 34113
                                Sphl
```

FIG 2 Cont.

Exon 23—Homolog 2

```
Query: 37663 cctccctgtctctgcactgacctcacgcatgtctgcaggagacctcatccacctggccag 37722
              |||||||||||||||||||||||||||| |||||||||||||||||||||||||||||||
Sbjct: 76762 cctccctgtctctgcactgacctcacgcctgtctgcaggagacctcatccacctggccag 76821

Query: 37723 ctcggacgtgcgggcaccacagccctcagagctgggagccgagtcaccatctcggatggt 37782
              ||| |||||||||||||||| |||| ||||||||||||||||||||||| ||||||||||
Sbjct: 76822 ctcagacgtgcgggcaccgcagcgctcagagctgggagccgagtcaccattgcggatggt 76881

Query: 37783 ggcgtcccaggcctacaacctgacctctgccctcatgcgcatcctcatgcgctcccgcgt 37842
              ||||||||||||||||||||||||||||||||||||||||||||| |||||||||||||
Sbjct: 76882 ggcgtcccaggcctacaacctgacctctgccctcatgcgcatcctcacgcgctcccgcgt 76941

Query: 37843 gctcaacgaggagcccctgacgctggcgggcgaggagatcgtggcccaggcaagcgctc 37902
              ||||||||||||||||| |||||||||||||||||||||| |||||||||||||||||
Sbjct: 76942 gctcaacgaggagcccgtgacgctggcgggcgaggagatcatggcccaggcaagcgctc 77001

Query: 37903 ggacccgcggagcctgctgtgctatggcggcgccccagggcctggctgccacttctccat 37962
              |||||||||||||||||||||||||||||||||||||||||||||||||||||| |||||
Sbjct: 77002 ggacccgcggagcctgctgtgctatggcggcgccccagggcctggctgccacctctccat 77061

Query: 37963 ccccgaggctttcagcggggccctggccaacctcagtgacgtggtgcagctcatctttct 38022
              |||| |||||||||||| ||||| |||||||||||||||||||||||||||| |||||||
Sbjct: 77062 ccctaggctttcagcagggcccggccaacctcagtgacgtggtgcagctcgtctttct 77121

Query: 38023 ggtggactccaatccctttcccttttggctatatcagcaactacaccgtctccaccaaggt 38082
              |||||||||||||||||||| ||||||||||||||||||||||||||||||||||||||
Sbjct: 77122 ggtggactccaatccctttctctttggctatatcagcaactacaccgtctccaccaaggt 77181

Query: 38083 ggcctcgatggcattccagacacaggccggcgcccagatccccatcgagcggctggcctc 38142
              |||||||||||| ||||||||||||||| |||||||||||||||||||| ||||||||||
Sbjct: 77182 ggcctcgatggcgttccagacacaggccggcgcccagatccccatcgagcgctggcctc 77241

Query: 38143 agagcgcgccatcaccgtgaaggtgcccaacaactcggactgggctgcccggggccaccg 38202
              |||||||||||||||||||||||||||||||||||||||||||||||||||||||||||
Sbjct: 77242 agagcgcgccatcaccgtgaaggtgcccaacaactcggactgggctgcccggggccaccg 77301

Query: 38203 cagctccgccaactccgccaactccgttgtggtccagccccaggcctccgtcggtgctgt 38262
              ||||||        |||||||||||||||||||||||||||||||||||||||||||||
Sbjct: 77302 cagctc---------cgccaactccgttgtggtccagccccaggcctccgtcggtgctgt 77352

Query: 38263 ggtcaccctggacagcagcaaccctgaggccgggctgcatctgcagctcaactatacgct 38322
              |||||||||||||||||||||||||| ||||| ||||| ||||||||||||||||||||
Sbjct: 77353 ggtcaccctggacagcagcaaccctgtggccgtgctgcatctgcagctcaactatacgct 77412

Query: 38323 gctggacggtgcgtgcagcgggtggggcacacgcggccccctggccttgttcttgggggg 38382
              |||||||||| |||||||||||||||||||||||||||||||||||||||||||||||
Sbjct: 77413 gctggacggtgtgtgcagcgggtggggcacacgcggcccctggccttgttcttgggggg 77472
```

FIG 2 Cont.

Exon 29 and 30—Homolog 1

```
Query: 41535 ttttgcgcttccggcgcctgctggtggctgagctgcagcgtggcttctttgacaagcaca 41594
              |  ||||||||||||||||||||||||||||  ||||||||||||||||||||||||||||
Sbjct: 37269 tgttgcgcttccggcgcctgctggtggctg-gctgcagcgtggcttctttgacaagcaca 37327

Query: 41595 tctggctctccatatgggaccggccgcctcgtagccgtttcactcgcatccagagggcca 41654
              ||||||||||||||||||||||||||||||||| ||| ||||||||||||||||||||||
Sbjct: 37328 tctggctctccatatgggaccggccgcctcggagctgtttcactcgcatccagagggcca 37387

Query: 41655 cctgctgcgttctcctcatctgcctcttcctgggcgccaacgccgtgtggtacgggctg 41714
              |||||||||||||||||||||| ||||||||||||||||||||||||||||||||||||
Sbjct: 37388 cctgctgcgttctcctcatctgtctcttcctgggcgccaacgccgtgtggtacgggctg 37447

Query: 41715 ttggcgactctgcctacaggtgggtgccgtaggggtcggggcagcctcttcctgcccagc 41774
              ||||  |||||||||||||||||||||||||||||||||||  ||||||||||||||||
Sbjct: 37448 ttggagactctgcctacaggtgggtgccgtaggggtcgggacagcctcttcctgcccagc 37507

Query: 41775 ccttcctgcccctcagcctcacctgtgtggcctcctctcctccacacagcacggggcatg 41834
              |||||||||||||||||||||||||||||||||||||||||||||||||||||||||| ||
Sbjct: 37508 ccttcctgcccctcagcctcacctgtgtggcctcctctcctccacacagcacggggcgtg 37567

Query: 41835 tgtccaggctgagcccgctgagcgtcgacacagtcgctgttggcctggtgtccagcgtgg 41894
              ||||||||||  |||||||||||||||||||||||||||||||||||||||||||||||
Sbjct: 37568 tgtccaggctgaacccgctgagcgtcgacacagtcgctgttggcctggtgtccagcgtgg 37627

Query: 41895 ttgtctatcccgtctacctggccatcctttttctcttccggatgtcccggagcaaggtgg 41954
              |||||||||||||||||||||||||||| |||||||||||||||||||||||||||||
Sbjct: 37628 ttgtctatcccgtctacctggccatcctctttctcttccggatgtcccggagcaaggtgg 37687

AvrII or BlnI
Query: 41955 gctgggctggggacccggagtactgggaatggagcctgggcctcggcaccatgcctag 42014
              |||||||||||||||||||||||||||||||||||||||||||||||||||||||| ||
Sbjct: 37688 gctgggctggggacccggagtactgggaatggagcctgggcctcggcaccatgcccag 37747

Query: 42015 ggccgccactttccagtgctgcagccagagggaaaggcgtccaccaaaggctgctcggga 42074
              ||||||||||||||||||||||||||||||||||||||||||||||||||||||||||||
Sbjct: 37748 ggccgccactttccagtgctgcagccagagggaaaggcgtccaccaaaggctgctcggga 37807
```

FIG 2 Cont.

Exon 29 and 30—Homolog 2

```
Query: 41535 ttttgcgcttccggcgcctgctggtggctgagctgcagcgtggcttctttgacaagcaca 41594
              | ||||||||||||||||||||||||||||||||||||||||||||||||||||||||
Sbjct: 80620 tgttgcgcttccggcgcctgctggtggctgagctgcagcgtggcttctttgacaagcaca 80679

Query: 41595 tctggctctccatatgggaccggccgcctcgtagccgtttcactcgcatccagagggcca 41654
              |||||||||||||||||||||||| ||||||||  |||||||||||||||||||||||
Sbjct: 80680 tctggctctccatatgggaccggccacctcgtagctgtttcactcgcatccagagggcca 80739

Query: 41655 cctgctgcgttctcctcatctgcctcttcctgggcgccaacgccgtgtggtacggggctg 41714
              ||||||||||||||||||||||||||||||||||||||||||||||||||||||||||
Sbjct: 80740 cctgctgcgttctcctcatctgcctcttcctgggcgccaacgccgtgtggtacggggctg 80799

Query: 41715 ttggcgactctgcctacaggtgggtgccgtaggggtcggggcagcctcttcctgcccagc 41774
              |||| |||||||||||||||||||||||||||||||||||  |||||||||||||||||
Sbjct: 80800 ttggtgactctgcctacaggtgggtgccgtaggggtcgggacagcctcttcctgcccagc 80859

Query: 41775 ccttcctgccctcagcctcacctgtgtggcctcctctcctccacacagcacggggcatg 41834
              |||||||||||||||||||||||||||||||||||||||||||||||||||||||||
Sbjct: 80860 ccttcctgccctcagcctcacctgtgtggcctcctctcctccacacagcacggggcatg 80919

Query: 41835 tgtccaggctgagcccgctgagcgtcgacacagtcgctgttggcctggtgtccagcgtgg 41894
              |||||||||||||  |||||||||||||||||||||||||||||||||||||||||||
Sbjct: 80920 tgtccaggctgagcccgctgagcgtcgacacagtcgctgttggcctggtgtccagcgtgg 80979

Query: 41895 ttgtctatcccgtctacctggccatcctttttctcttccggatgtcccggagcaaggtgg 41954
              ||||||||||||||||||||||||||||||| |||||||||||||||||||||||||
Sbjct: 80980 ttgtctatcccgtctacctggccatcctttttctcttccggatgtcccggagcaaggtgg 81039

Query: 41955 gctgggctggggacccgggagtactgggaatggagcctgggcctcggcaccatgcctag 42014
              |||||||||||||||||||||||||||||||||||||||||||||||||||||||| ||
Sbjct: 81040 gctgggctggggacccgggagtactgggaatggagcctgggcctcggcaccatgcccag 81099

Query: 42015 ggccgccactttccagtgctgcagccagagggaaaggcgtccaccaaaggctgctcggga 42074
              ||||||||||||||||||||||||||||||||||||||||||||||||||||||||||
Sbjct: 81100 ggccgccactttccagtgctgcagccagagggaaaggcgtccaccaaaggctgctcggga 81159
```

FIC 10 B

| | Polymorph | Probable | Missense | Frame Shi | Indeterminate | |
|---|---|---|---|---|---|---|
| 1 | 13 | 8 | 1 | 0 | 0 | 22 |
| 2 | 13 | 8 | 1 | 0 | 0 | 22 |
| 3 | 14 | 6 | 0 | 0 | 0 | 20 |
| 4 | 14 | 6 | 0 | 0 | 0 | 20 |
| 5 | 1 | 1 | 1 | 0 | 0 | 3 |
| 6 | 1 | 2 | 0 | 0 | 0 | 3 |
| 7 | 4 | 0 | 0 | 1 | 0 | 5 |
| 8 | 0 | 0 | 2 | 0 | 0 | 2 |
| 9 | 13 | 4 | 0 | 0 | 1 | 18 |
| 10 | 4 | 0 | 1 | 1 | 0 | 6 |
| 11 | 16 | 5 | 0 | 0 | 0 | 21 |
| 12 | 0 | 1 | 0 | 0 | 0 | 1 |
| 13 | 13 | 9 | 2 | 1 | 0 | 25 |
| 14 | 1 | 0 | 1 | 1 | 0 | 3 |
| 15 | 1 | 1 | 1 | 0 | 0 | 3 |
| 16 | 2 | 1 | 0 | 0 | 0 | 3 |
| 17 | 13 | 12 | 2 | 1 | 0 | 28 |
| 18 | 16 | 6 | 0 | 0 | 0 | 22 |
| 19 | 4 | 3 | 0 | 0 | 0 | 7 |
| 20 | 0 | 0 | 0 | 0 | 0 | 0 |

FIG 11

| Gene | | Exon | Ampli-con | Temp | PC Ret Time | PC Height | NC Ret Time | NC Height |
|---|---|---|---|---|---|---|---|---|
| 1 | x | 1 | | | | | | |
| 1 | x | 2 | | 66 | 2.25-6.5 | 0.8-3.2 | 2-6.5 | 0.9-3.6 |
| 1 | x | 2 | | 67 | 0.7-5.8 | 0.8-3.2 | 0.7-5.8 | 1-4 |
| 1 | x | 3 | | 56 | 4.2-6.8 | 1-4 | 4-6.75 | 1.1-4.4 |
| 1 | x | 3 | | 57 | 3.5-6.5 | 0.7-2.8 | 4-6.5 | 1-4 |
| 1 | x | 4 | | 66 | 2-6.8 | 1-4 | 2-6.8 | 0.8-3.2 |
| 1 | x | 4 | | 67 | 1.5-6 | 0.5-2.0 | 1.5-6 | 1.1-4.4 |
| 1 | x | 5 | A | 66 | 2.6-4.6 | 1.3-5.4 | 2.7-4.7 | 1.3-5.2 |
| 1 | x | 5 | B | 67 | 2-6.5 | 0.4-7.0 | 3-6.5 | 0.5-4.6 |
| 1 | x | 5 | C | 67 | 3-6.5 | 1-4 | 3-6.5 | 1.2-4.8 |
| 1 | x | 5 | C | 68 | 1.7-5.8 | 0.7-2.8 | 2.5-5.8 | 1-4 |
| 1 | x | 6 | | 66 | 3.5-5.9 | 0.3-1.5 | 3.9-5.9 | 1.0-4.2 |
| 1 | x | 6 | | 67 | 2.5-5.4 | 0.5-2.0 | 3.4-5.4 | 1-4.2 |
| 1 | x | 6 | | 68 | 2.2-4.8 | 0.3-1.4 | 2.8-4.8 | 0.7-3.0 |
| 1 | x | 7 | | 66 | 2.7-6.25 | 0.5-2.0 | 3-6.25 | 0.6-2.4 |
| 1 | x | 7 | | 68 | 1.5-5 | 0.9-3.6 | 1.5-5 | 0.6-2.4 |
| 1 | x | 8 | | 68 | 1.5-5 | 1.3-5.2 | 1.7-5 | 1-4 |
| 1 | x | 9 | | 67 | 3.5-6.5 | 0.5-2.0 | 3.5-6.8 | 0.25-2.0 |
| 1 | x | 10 | | 65 | 2.5-6.5 | 0.9-3.6 | 3-6.5 | 1.9-7.6 |
| 1 | x | 10 | | 67 | 1.5-5 | 1.5-6 | 1.5-5 | 2-8 |
| 1 | x | 11 | A | 67 | 1.5-6.5 | 0.7-2.8 | 2-6.5 | 2-8 |
| 1 | x | 11 | A | 68 | 1.5-5.5 | 0.8-3.2 | 2-5.8 | 1.3-5.2 |
| 1 | x | 11 | B | 66 | 3-6.8 | 1-4 | 3-6.8 | 1-4 |
| 1 | x | 11 | B | 67 | 2-6 | 1.5-6 | 2-6 | 1.2-4.8 |
| 1 | x | 11 | C | 66 | 4.2-6.2 | 1.5-6 | 4.2-6.2 | 2.5-10.2 |
| 1 | x | 11 | C | 67 | 3.6-5.6 | 1.7-7 | 3.6-5.6 | 2.3-9.2 |
| 1 | x | 11 | C | 68 | 2.9-4.9 | 1.1-4.6 | 2.8-4.8 | 1.7-6.8 |
| 1 | x | 12 | | 63 | 4.4-6.6 | 0.6-2.4 | 4.7-6.7 | 1-4 |
| 1 | x | 12 | | 65 | 2.8-4.8 | 0.4-1.6 | 2.6-5.4 | 0.4-1.8 |
| 1 | x | 13 | | | | | | |
| 1 | x | 14 | | 66 | 1.5-5.5 | 0.6-2.4 | 0.7-5.5 | 0.6-2.4 |
| 1 | x | 15 | A | 67 | 2.5-6.5 | 0.8-3.2 | 2.5-6.5 | 1-4 |
| 1 | x | 15 | A | 68 | 1.5-5.75 | 1-4 | 1.5-5.75 | 1.2-4.8 |
| 1 | x | 15 | B | 67 | 2-5.75 | 0.5-2.0 | 2.75-5.75 | 1-4 |
| 1 | x | 15 | B | 68 | 1.5-5.25 | 0.6-2.4 | 2.5-5.5 | 0.9-3.6 |
| 1 | x | 15 | C | 68 | 2-6.5 | 0.4-1.6 | 2-6.5 | 0.8-3.2 |
| 1 | x | 15 | C | 69 | 1.5-6 | 0.5-2.0 | 1.5-6 | 0.75-3.0 |
| 1 | x | 15 | D | 67 | 3.75-7.25 | 1.5-6 | 3.75 | 7.25 |
| 1 | x | 15 | D | 68 | 3-6.5 | 1-4 | 3-6.5 | 1.2-4.8 |
| 1 | x | 15 | E | 65 | 3-6.5 | 1-4 | 3-6.5 | 1.5-6 |
| 1 | x | 15 | E | 66 | 2-6 | 0.8-3.2 | 2-6 | 1.3-5.2 |
| 1 | x | 15 | F | 65 | 4-7 | 1.4-5.6 | 3.75-7 | 1.2-4.8 |
| 1 | x | 15 | F | 66 | 3-6.5 | 1-4 | 3-6.5 | 1-4 |
| 1 | x | 15 | F | 67 | 1.5-5.75 | 1.3-5.2 | 1.5-5.75 | 1-4 |
| 1 | x | 15 | G | 66 | 3-6 | 0.8-3.2 | 3-6 | 1.1-4.4 |
| 1 | x | 15 | G | 68 | 1.5-4.5 | 1-4 | 1.5-4.5 | 1.5-6 |

FIG 11 Cont.

| 1 | x | 15 | H | 65 | 2-6.5 | 1.5-6 | 2-6.5 | 1.5-6 |
|---|---|---|---|---|---|---|---|---|
| 1 | x | 15 | H | 66 | 1.5-5.5 | 1-4 | 1.5-5.75 | 1-4 |
| 1 | x | 15 | I | 66 | 3-7 | 2-8 | 3-7 | 1.8-7.2 |
| 1 | x | 15 | I | 67 | 2.5-6.5 | 1.5-6 | 2.5-6.5 | 1.5-6 |
| 1 | x | 15 | J | 64 | 4-7.5 | 2.2-8.8 | 4-7.5 | 2-8 |
| 1 | x | 15 | J | 65 | 4-7 | 2-8 | 4-7 | 1.5-6 |
| 1 | x | 15 | J | 66 | 3-6.5 | 1.5-6 | 2-6.5 | 1.1-4.4 |
| 1 | x | 15 | K | 65 | 3.5-6.5 | 1-4 | 3.75-6.5 | 0.8-3.2 |
| 1 | x | 15 | K | 66 | 3-6.5 | 0.7-2.8 | 3.5-6.5 | 0.6-3.2 |
| 1 | x | 15 | K | 67 | 2-6 | 0.6-2.4 | 2-5.5 | 0.5-2.0 |
| 1 | x | 15 | L | | | | | |
| 1 | x | 15 | M | 66 | 4.5-7 | 1-4 | 4.5-7 | 1.5-6 |
| 1 | x | 15 | M | 67 | 4-6.75 | 1-4 | 4-6.75 | 1.3-5.2 |
| 1 | x | 15 | N | | | | | |
| 1 | x | 16 | | 67 | 1.5-5.5 | 2.25-9 | 2.0-5.5 | 3-13 |
| 1 | x | 17 | | 65 | 2.5-6 | 1.5-6 | 2.5-6 | 1.75-7 |
| 1 | x | 17 | | 66 | 1.5-5 | 1.25-5 | 1.5-5 | 1.75-7 |
| 1 | x | 18 | | 66 | 3-6.5 | 2-8 | 3-6.5 | 3.25-13 |
| 1 | x | 18 | | 67 | 4-6.4 | 3.8-16 | 4.25-6.25 | 6.2-24.8 |
| 1 | x | 18 | | 68 | 1.5-5 | 2.5-10 | 1.5-5 | 2.75-11 |
| 1 | x | 19 | | 67 | 3-6.5 | 1.5-6 | 3-6.5 | 3-12 |
| 1 | x | 19 | | 68 | 3.0-6.5 | 1.5-6 | 3-6.5 | 3-12 |
| 1 | x | 20 | | 65 | 3.5-6.5 | 2-8 | 3.5-6.5 | 2.25-9 |
| 1 | x | 20 | | 66 | 2.5-6 | 1.25-5 | 2.5-6 | 1.75-7 |
| 1 | x | 20 | | 67 | 1.5-5.5 | 1.25-5 | 1.5-5.5 | 1.75-7 |
| 1 | x | 21 | | 65 | 3-7 | 1.5-6 | 3-7 | 4-16 |
| 1 | x | 21 | | 67 | 1.5-5.5 | 2.25-9 | 1.5-5.5 | 4.5-18 |
| 1 | x | 22 | | 66 | 4-7.5 | 2-8 | 4-7 | 2-8 |
| 1 | x | 22 | | 67 | 3-7.25 | 1.5-6 | 3.5-6.5 | 1.5-6 |
| 1 | x | 23 | A | 65 | 3.5-6.5 | 0.75-3.0 | 3.5-6.5 | 1.5-6.0 |
| 1 | x | 23 | A | 66 | 2.5-6.0 | 0.5-2.0 | 2.5-6.0 | 1.25-5.0 |
| 1 | x | 23 | A | 68 | 1.5-4.5 | 2.5-10.0 | 1.5-4.5 | 2.5-10.0 |
| 1 | x | 23 | B | 63 | 3.5-7.25 | 1.5-6 | 3.5-7.25 | 1.5-6 |
| 1 | x | 23 | B | 66 | 1.5-6.5 | 0.9-3.5 | 1.5-6.5 | 1-4 |
| 1 | x | 23 | B | 67 | 1.25-5.5 | 1-4 | 1.25-5.5 | 1-4 |
| 1 | x | 23 | C | 61 | 3-6.25 | 1.5-6 | 3-6.25 | 3.25-13 |
| 1 | x | 23 | C | 66 | 1.5-5 | 2.25-9 | 2.5-5 | 4.25-17 |
| 1 | x | 23 | C | 67 | 1.5-5 | 2.75-11 | 2-5 | 5.5-22 |
| 1 | x | 24 | | 65 | 2.5-6.0 | 0.5-2.0 | 2.5-6.0 | 0.6-3.0 |
| 1 | x | 25 | | 65 | 2-6 | 0.7-4 | 2-6 | 0.7-4 |
| 1 | x | 25 | | 67 | 1.5-4.5 | 2-8 | 1.5-4.5 | 2-8 |
| 1 | x | 26 | | 64 | 2.5-6 | 0.9-3.6 | 2.5-6 | 0.9-3.6 |
| 1 | x | 26 | | 66 | 1.5-4.5 | 1.75-7 | 1.5-4.5 | 1.75-7 |
| 1 | x | 27 | | 65 | 3.5-6.7 | 1.5-6 | 3.5-6.7 | 1.5-6 |
| 1 | x | 27 | | 66 | 2.5-6 | 2-8 | 2-5.7 | 1.25-5 |
| 1 | x | 28 | | 66 | 1.5-5.75 | 1-4 | 1.5-5.75 | 1-4 |
| 1 | x | 29 | | 65 | 1.5-6.25 | 1.5-6 | 1.5-6.25 | 3-12 |
| 1 | x | 29 | | 66 | 1.5-5.25 | 1.5-6 | 1.5-5.25 | 2.5-8.5 |
| 1 | x | 30 | | | | | | |

FIG 11 Cont.

| 1 | x | 31 |   | 66 | 3-6.5 | 2.5-10 | 3-6.5 | 1-4 |
|---|---|---|---|---|---|---|---|---|
| 1 | x | 31 |   | 68 | 1.5-5.5 | 1.5-6 | 1.5-5.5 | 0.5-2 |
| 1 | x | 32 |   | 62 | 2-6.5 | 1.25-5.0 | 2-6.5 | 3.5-14 |
| 1 | x | 33 |   | 64 | 4.2-6.2 | 1.4-6 | 4.3-6.3 | 1.5-6 |
| 1 | x | 33 |   | 67 | 2.5-4.7 | 0.8-3.5 | 2.7-4.7 | 1.2-4.8 |
| 1 | x | 34 |   |   |   |   |   |   |
| 1 | x | 34 |   |   |   |   |   |   |
| 1 | x | 35 |   | 64 | 4.3-6.6 | 1.4-5.5 | 4.5-6.5 | 2.4-9.5 |
| 1 | x | 35 |   | 66 | 2.6-5.1 | 1.1-4.4 | 3.1-5.1 | 1.75-7 |
| 1 | x | 36 |   | 66 | 3.3-5.7 | 0.5-2.0 | 3.6-5.6 | 1-4 |
| 1 | x | 36 |   | 67 | 2.7-5.1 | 0.6-2.5 | 3.1-5.1 | 1.1-4.4 |
| 1 | x | 37 |   | 64 | 3-5.75 | 0.65-2.6 | 3.7-5.7 | 1.1-4.5 |
| 1 | x | 37 |   | 66 | 2-4.75 | 0.9-3.6 | 2.7-4.7 | 1-4 |
| 1 | x | 38 |   | 65 | 3.5-6.5 | 1.1-4.5 | 4.3-6.3 | 1.6-6.5 |
| 1 | x | 38 |   | 66 | 3-5.75 | 0.7-3.0 | 3.5-5.5 | 1-4 |
| 1 | x | 39 |   | 66 | 1.5-4.5 | 1.1-4.6 | 2-4.6 | 1.25-3.0 |
| 1 | x | 39 |   | 67 | 1.5-4 | 1.25-3.0 | 1.5-4 | 0.7-3.0 |
| 1 | x | 40 |   | 66 | 1.5-5.5 | 0.6-2.5 | 3.25-5.25 | 0.7-3.0 |
| 1 | x | 41 |   | 67 | 2.5-5.75 | 0.9-3.6 | 3.75-5.75 | 1.1-4.4 |
| 1 | x | 42 |   | 70 | 2.75-5.75 | 0.5-2.0 | 3-5.8 | 0.3-1.2 |
| 1 | x | 42 |   | 71 | 2.5-4.5 | 0.7-3.0 | 2.6-4.6 | 0.6-2.4 |
| 1 | x | 43 |   | 67 | 4-6.75 | 0.4-1.6 | 4-6.75 | 0.6-2.4 |
| 1 | x | 43 |   | 68 | 3.75-6.5 | 0.4-1.6 | 3.75-6.5 | 0.6-2.4 |
| 1 | x | 43 |   | 70 | 2.25-5.25 | 0.25-2 | 2.25-5.25 | 0.6-2.4 |
| 1 | x | 44 |   | 66 | 3.25-5.75 | 0.5-2.0 | 3.7-5.7 | 0.8-3.2 |
| 1 | x | 45 |   | 65 | 3.5-6.25 | 0.4-1.6 | 4.1-6.1 | 0.9-3.6 |
| 1 | x | 45 |   | 66 | 2.5-5.5 | 0.4-1.6 | 3.5-5.5 | 0.8-3.2 |
| 1 | x | 46 | A | 66 | 4.25-6.5 | 0.4-1.6 | 4.4-6.4 | 0.8-3.2 |
| 1 | x | 46 | A | 67 | 3.25-5.25 | 0.3-1.2 | 3.5-5.5 | 0.5-2.0 |
| 1 | x | 46 | B | 65 | 4-6.75 | 1-4 | 4-6.75 | 1.2-4.8 |
| 1 | x | 46 | B | 68 | 1.75-4.75 | 1.3-5.2 | 1.75-4.75 | 1.5-6 |
| 2 | x | 1 | A | 70 | 3-6 | 1.5-6 | 3-6 | 1-4 |
| 2 | x | 1 | A | 71 | 2-5.75 | 0.6-2.4 | 2-5.75 | 0.9-3.6 |
| 2 | x | 1 | A | 72 | 1.5-5.25 | 0.5-3.0 | 1.5-5.25 | 0.5-2 |
| 2 | x | 1 | B | 67 | 2.5-6.5 | 0.6-2.5 | 2.5-6.5 | 0.6-2.5 |
| 2 | x | 1 | B | 70 | 1.5-4.5 | 0.7-3 | 1.5-4.5 | 1-4 |
| 2 | x | 1 | B | 71 | 1-4 | 0.5-2 | 1-4 | 0.7-3 |
| 2 | x | 1 | C | 69 | 2.5-6.5 | 1.25-5 | 2.5-6.5 | 1-4 |
| 2 | x | 1 | C | 70 | 1.5-6.5 | 0.8-2.5 | 1.5-6.5 | 0.8-3.5 |
| 2 | x | 1 | C | 71 | 1.5-5.75 | 0.8-3.5 | 1.5-5.75 | 0.8-3.5 |
| 2 | x | 2 |   | 58 | 2.5-4.5 | 1.2-5.0 | 3.2-5.2 | 1.4-5.6 |
| 2 | x | 3 |   | 58 | 4.7-6.9 | 2.9-11.6 | 4.9-6.9 | 3.5-14 |
| 2 | x | 3 |   | 59 | 4.4-6.9 | 2.1-8.4 | 4.7-6.7 | 2.0-8.0 |
| 2 | x | 3 |   | 60 | 3.5-6.1 | 1.3-5.2 | 3.9-5.9 | 1.6-6.4 |
| 2 | x | 4 |   | 60 | 3.4-6.1 | 1.7-7.0 | 4.1-6.1 | 0.9-3.8 |
| 2 | x | 5 |   | 58 | 4.5-6.5 | 2.3-9.2 | 4.6-6.6 | 2.3-9.4 |
| 2 | x | 5 |   | 59 | 3.9-6.2 | 1.6-6.6 | 4.3-6.3 | 1.7-6.8 |
| 2 | x | 6 |   | 57 | 1.5-6.25 | 1.5-6 | 1.5-6.25 | 2-8 |
| 2 | x | 7 |   | 53 | 3.4-6.6 | 1.2-5.0 | 3.3-6.6 | 1.0-4.0 |

FIG 11 Cont.

| 2 | x | 7  |   | 56 | 2.5-4.5   | 2.5-10.2 | 2.6-5.2  | 1.1-4.4  |
|---|---|----|---|----|-----------|----------|----------|----------|
| 2 | x | 8  |   | 54 | 3.7-6.2   | 1.5-6    | 3.7-6.2  | 5.5-22   |
| 2 | x | 8  |   | 58 | 3-6       | 0.8-3.2  | 2.5-6    | 4-16     |
| 2 | x | 9  |   | 54 | 3-6.5     | 0.5-2.0  | 3.5-6.5  | 1-4      |
| 2 | x | 9  |   | 57 | 1.5-4.75  | 0.5-2    | 1.5-4.75 | 0.5-2.0  |
| 2 | x | 10 |   |    |           |          |          |          |
| 2 | x | 10 |   |    |           |          |          |          |
| 2 | x | 11 |   | 58 | 2.5-6.75  | 2.3-9.2  | 2.5-6.75 | 2-8      |
| 2 | x | 11 |   | 59 | 1.75-6.5  | 1.5-6    | 1.5-6.5  | 1-4      |
| 2 | x | 12 |   | 60 | 1.5-5.75  | 0.7-2.8  | 1.5-5.5  | 0.8-3.2  |
| 2 | x | 13 |   | 60 | 3-6.2     | 1.2-4.8  | 4.2-6.2  | 1.2-5    |
| 2 | x | 13 |   | 61 | 2.5-5.5   | 1.2-5    | 2.5-5.5  | 0.9-4.0  |
| 2 | x | 14 |   | 63 | 2.5-4.5   | 1.1-4.4  | 3.2-5.2  | 2.5-10.0 |
| 2 | x | 15 |   | 60 | 2-6.5     | 0.9-3.6  | 2-6.5    | 1-4      |
| 2 | x | 15 |   | 61 | 1.5-6     | 1.3-5.2  | 1.5-6    | 1.5-6    |

| Verified By | Exon | Ampli con | Long Range PCR | Mg | DMSO | Anneal Temp | Initial Denatur Temp | Initial Denature Time | # Cycles | Cycle Denatur Temp | Cycle Denatur Time | Anneal Temp | Anneal Time | Ext Temp | Ext Time | Final Ext Temp | Final Ext Time | LR Dilution | | Exon | Ampli seq | | |
|---|---|---|---|---|---|---|---|---|---|---|---|---|---|---|---|---|---|---|---|---|---|---|---|
| | 66 | 1 | A | | 1.1 | 5% | 72 | 95 | 10 min | 35 | 95 | 45 sec | 72 | 2min | 72 | 1 min | 72 | 10 min | NA | 66 | 1 | A | 16 | 16A |
| | 68 | | C | | 1.1 | 5% | 72 | 95 | 10 min | 35 | 95 | 45 sec | 72 | 2min | 72 | 1 min | 72 | 10 min | NA | 68 | | C | 16 | 16A |
| | 67 | | B | | 1.1 | 7.50% | 74 | 95 | 10 min | 35 | 95 | 45 sec | 74 | 2min | 74 | 1 min | 74 | 10 min | NA | 67 | | B | 17 | 17A |
| | 73 | 6 | | | 2 | 0 | 50 | 95 | 10 min | 35 | 92 | 40 sec | 50 | 40 sec | 72 | 40 sec | 72 | 10 min | NA | 73 | 6 | | 18 | 18A |
| | 75 | 8 | | | 2 | 0 | 50 | 95 | 10 min | 35 | 92 | 40 sec | 50 | 40 sec | 72 | 40 sec | 72 | 10 min | NA | 75 | 8 | | 18 | 18A |
| | 76 | 9 | | | 2 | 0 | 50 | 95 | 10 min | 35 | 92 | 40 sec | 50 | 40 sec | 72 | 40 sec | 72 | 10 min | NA | 76 | 9 | | 18 | 18A |
| | 79 | 12 | | | 2 | 0 | 50 | 95 | 10 min | 35 | 92 | 40 sec | 50 | 40 sec | 72 | 40 sec | 72 | 10 min | NA | 79 | 12 | | 18 | 18A |
| | 70 | 3 | | | 1.5 | 5% | 55 | 95 | 10 min | 35 | 92 | 40 sec | 55 | 40 sec | 72 | 60 sec | 72 | 10 min | NA | 70 | 3 | | 19 | 19A |
| | 71 | 4 | | | 1.5 | 5% | 55 | 95 | 10 min | 35 | 92 | 40 sec | 55 | 40 sec | 72 | 40 sec | 72 | 10 min | NA | 71 | 4 | | 19 | 19A |
| | 72 | 5 | | | 1.5 | 5% | 55 | 95 | 10 min | 35 | 92 | 40 sec | 55 | 40 sec | 72 | 40 sec | 72 | 10 min | NA | 72 | 5 | | 19 | 19A |
| | 74 | 7 | | | 1.5 | 5% | 55 | 95 | 10 min | 35 | 92 | 40 sec | 55 | 40 sec | 72 | 40 sec | 72 | 10 min | NA | 74 | 7 | | 19 | 19A |
| | 77 | 10 | | | 1.5 | 5% | 55 | 95 | 10 min | 35 | 92 | 40 sec | 55 | 40 sec | 72 | 40 sec | 72 | 10 min | NA | 77 | 10 | | 19 | 19A |
| | 78 | 11 | | | 1.5 | 5% | 55 | 95 | 10 min | 35 | 92 | 40 sec | 55 | 40 sec | 72 | 40 sec | 72 | 10 min | NA | 78 | 11 | | 19 | 19A |
| | 80 | 13 | | | 1.5 | 5% | 55 | 95 | 10 min | 35 | 92 | 40 sec | 55 | 40 sec | 72 | 40 sec | 72 | 10 min | NA | 80 | 13 | | 19 | 19A |
| | 82 | 15 | | | 1.5 | 5% | 55 | 95 | 10 min | 35 | 92 | 40 sec | 55 | 40 sec | 72 | 40 sec | 72 | 10 min | NA | 82 | 15 | | 19 | 19A |
| | 69 | 2 | | | 2 | 0 | 58 | 95 | 10 min | 35 | 92 | 40 sec | 58 | 40 sec | 72 | 40 sec | 72 | 10 min | NA | 69 | 2 | | 20 | 20A |
| | 81 | 14 | | | 2 | 0 | 62 | 95 | 10 min | 35 | 92 | 40 sec | 62 | 40 sec | 72 | 40 sec | 72 | 10 min | NA | 81 | 14 | | 21 | 21A |

… # COMPOSITIONS AND METHODS FOR GENETIC ANALYSIS OF POLYCYSTIC KIDNEY DISEASE

RELATED APPLICATIONS

This application is a non-provisional application which claims priority under 35 U.S.C §119 (e) to U.S. Provisional Application Ser. No. 60/328,739; filed Oct. 12, 2001, the entirety of which is incorporated herein by reference.

FIELD OF THE INVENTION

The invention relates to a genetic testing method for identifying alterations or the absence of such alterations in a gene associated with Autosomal Dominant Polycystic Kidney Disease.

BACKGROUND OF THE INVENTION

Autosomal dominant polycystic kidney disease (ADPKD) is an exceptionally common hereditary nephropathology with an incidence of about 1 in 800 live births. The disease is progressive, phenotypically characterized by bilaterally enlarged polycystic kidneys, and typically resulting in end-stage renal disease (ESRD) by the age of 65 years. The more common complications include hypertension, macrohaematuria, urinary-tract infection, cardiac-valve abnormalities, and hernia of the anterior abdominal wall. Cyst formation is also commonly observed in the liver, although the occurrence is not associated with functional impairment of the organ. Although not as frequently reported, additional extrarenal manifestations include pancreatic cysts, connective tissue abnormalities, and cerebral-artery aneurysms.

The typical age of onset is in middle life, but the range is from infancy to 80 years. The clinical presentation of ADPKD differs between and within families as partly explained by the genetically heterogeneous nature of the disorder. Mutations in two genes, PKD-1 and PKD-2, account for nearly all cases of ADPKD (e.g., for reviews, see Arnaout, 2001, Annu Rev. Med. 52:93–123; Koptides and Deltas, 2000, Hum. Genet. 107:115–126). PKD-1 and PKD-2 encode integral membrane proteins whose functions have not been fully elucidated. The major gene responsible for ADPKD, PKD-1, has been fully characterized and shown to encode an integral membrane protein, polycystin 1, which is thought to be involved in cell-cell and cell-matrix interaction. PKD-2 gene encodes polycystin-2 which is a predicted integral membrane protein with non-selective cation channel activity. Based on sequence homology with the alpha 1 subunit component of voltage-activated calcium channels, it has been postulated that polycystin-2 may play a role in ion channeling. The C-terminal cytoplasmic tails of polycystin-1 and polycystin-2 have been shown to interact using in vitro binding assays and in a directed two-hybrid interaction. The interaction occurs via a coiled-coil domain in PKD-1 and a region near R872 in PKD-2. Although the biological relevance of the interaction between the poly-cystins is not yet understood, it does suggest that PKD-1 and PKD-2 are likely to function along a common pathway.

Both ADPKD type 1 and type 2 share the entire range of renal and extrarenal manifestations, but type 2 appears to have a delayed onset relative to type 1. The common phenotypic complications observed for ADPKD including hypertension, hematuria, and urinary tract infection seem to be clinically milder in type 2 patients. The median age at death or onset of ESRD has been reported as 53 years in individuals with PKD-1 and 69 years in those with PKD-2. Women have been reported to have a significantly longer median survival of 71 years than men (67 years). No sex influence is apparent in PKD-1. Mutations in the PKD-1 gene are the cause of ADPKD in approximately 85% of the cases tested, while those in PKD-2 account for 15%. Although a small subset of families with ADPKD fail to demonstrate genetic linkage to either PKD-1 or PKD-2, raising the possibility of a third gene for ADPKD, the existence of a third disease-associated locus has been strongly challenged.

Despite the discovery of strong links between genetic alterations in PKD genes and the onset of ADPKD, the development of a genetic testing method for ADPKD predisposition for routine clinical use has been hindered by several technical obstacles.

One serious obstacle for developing a DNA-based testing method for ADPKD is that sequences related to the PKD transcript, for example, PKD-1, are duplicated at least three times on chromosome 16 proximal to the PKD-1 locus, forming PKD-1 homologues. Another obstacle is that the PKD-1 genomic interval also contains repeat elements that are present in other genomic regions. In addition, the sequences of PKD genes are extremely GC rich and a large number (15,816 bp) of nucleotides need to be analyzed for a thorough evaluation.

There is a need for the identification of segments of these sequences that are unique to the expressed PKD genes and not are present in the duplicated homologous sequences. There is also a need for developing a sensitive and specific genetic testing method for mutational analysis of PKD genes. The development of such genetic testing method would facilitate the diagnosis and management of ADPKD.

SUMMARY OF THE INVENTION

In one aspect, the present invention provides a method of mutation analysis of a target nucleic acid, the method comprising:

incubating a sample comprising the target nucleic acid in a reaction mixture, in the presence of at least one first nucleic acid and at least one second nucleic acid, where the first nucleic acid comprises a primer sequence which anneals to a unique site of a sequence of SEQ ID NO. 1 or 2, and the second nucleic acid has an opposite orientation from the first nucleic acid, and where the incubation produces amplified products;

generating duplexes in the amplified products; and detecting the presence or absence of a heteroduplex from the duplexes, where the presence of a heteroduplex indicates the presence of a potential mutation in the target nucleic acid, and where the absence of a heteroduplex indicates the absence of a mutation in the target nucleic acid.

In one embodiment, the method further comprises determining the sequence of a heteroduplex region; and comparing the sequence of the heteroduplex region to SEQ ID NO. 1 or 2; where a sequence difference in the heteroduplex region compared to SEQ ID NO. 1 or 2 resulting in a predicted functional change in the protein encoded by the target nucleic acid is indicative of a mutation in the target nucleic acid.

Preferably, the first or second nucleic acid comprises a sequence selected from the group consisting of SEQ ID NOs. 3–49.

In another embodiment, the method further comprising performing a nested amplification reaction using the amplified products generated by the first and second nucleic acids as templates and generating duplexes in amplified products from the nested amplification.

Preferably, the nested amplification reaction is performed using at least one primer selected from the group consisting of SEQ ID NOs. 3–49 and their complementary sequences.

In a preferred embodiment, the presence or absence of a heteroduplex from the duplexes is identified by DHPLC.

In also a preferred embodiment, the sequence of the heteroduplex region is determined by DNA sequencing.

Preferably, the second nucleic acid of the subject method comprises a primer sequence which anneals to a unique site within a sequence of SEQ ID NO. 1 or 2.

Also preferably, the sample comprising the target template is selected from the group consisting of: genomic DNA, cDNA, total RNA, mRNA, and a cell sample.

In one embodiment, the incubating step comprises an amplification reaction selected from the group consisting of: a polymerase chain reaction, a ligase chain reaction (LCR) and a nucleic acid-specific based amplification.

The subject method of the invention may further comprise confirming the amplified product is a PKD-specific product with one or more restriction enzymes.

Preferably, the restriction enzyme cleaves a PKD-specific product to generate a digestion pattern distinguishable from a PKD homologue product.

More preferably, the restriction enzyme is selected from the group consisting of: Pst I, Stu I, Xma I, Mlu I, Pvu II, BssHII, Fsp I, Msc I, and Bln I.

In another aspect, the invention provides a diagnosis method for identifying a patient affected with PKD, the method comprising:

(a) obtaining a sample from an individual;

(b) incubating the sample in a reaction mixture, in the presence of at least one first nucleic acid and at least one second nucleic acid, where the first nucleic acid comprises a primer sequence which anneals to a unique site within a sequence of SEQ ID NO. 1 or 2, and the second nucleic acid has an opposite orientation from the first nucleic acid, and where the incubation produces amplified products;

(c) generating duplexes in the amplified products;

(d) detecting the presence or absence of a heteroduplex from the duplexes, and (e) determining the sequence of the heteroduplex region where the presence of a mutation in the heteroduplex region as compared to SEQ ID No. 1 or 2 is indicative that the individual is affected with PKD.

Preferably, the detection of a heteroduplex is performed by DHPLC.

Also preferably, the sequence is determined by DNA sequencing.

In one embodiment, the second nucleic acid comprises a primer sequence which anneals to a unique site within a sequence of SEQ ID NO. 1 or 2.

In another embodiment, the first or second nucleic acid comprises a primer sequence selected from the group consisting of SEQ ID NOs. 3–49.

The diagnosis method of the invention may further comprise performing a nested amplification reaction using the amplified products generated by the first and second nucleic acids as templates and generating duplexes from the nested amplification.

In one embodiment, the nested amplification reaction is performed using at least one primer selected from the group consisting of SEQ ID NOs. 3–49 and their complementary sequences.

Preferably, the sample in the diagnosis method is selected from the group consisting of: a genomic DNA, cDNA, total RNA, mRNA, and a cell.

Also preferably, the amplification reaction is selected from the group consisting of: a polymerase chain reaction, a ligase chain reaction (LCR) and a nucleic acid-specific based amplification.

The diagnosis method may further comprise verifying the specifically amplified product with one or more restriction enzymes.

Preferably, the restriction enzyme cleaves a PKD-specific product to generate a digestion pattern distinguishable from a PKD homologue product.

More preferably, the restriction enzyme is selected from the group consisting of: Pst I, Stu I, Xma I, Mlu I, Pvu II, BssHII, Fsp I, Msc I, and Bln I.

In a further aspect, the invention provides one or more nucleic acid primer, where each primer is an isolated nucleic acid selected from the group of SEQ ID NOs 3–49, or the complement thereof.

The invention also provides a pair of nucleic acids, where at least one nucleic acid of the pair is selected from the group of SEQ ID NOs 3–49.

Preferably, the pair of nucleic acids have an opposite orientation and amplify a fragment of a template nucleic acid comprising a sequence of SEQ ID NO. 1 or 2.

In another aspect, the invention provides a composition comprising at least one isolated first nucleic acid and at least one isolated second nucleic acid, where the first nucleic acid is selected from the group of SEQ ID NOs. 3–49 and their complementary sequences, and the second nucleic acid has an opposite orientation from the first nucleic acid, and wherein the first and second nucleic acids amplify a fragment of a template nucleic acid comprising a sequence of SEQ ID NO. 1 or 2.

In one embodiment, the composition of the invention further comprises at least one component selected from the group consisting of: a DNA polymerase, a template nucleic acid, a restriction enzyme, one or more control oligonucleotide primers, ddNTPs, a PCR reaction buffer and their combination thereof.

Preferably, the template nucleic acid in the composition is a genomic DNA or cDNA.

In a further aspect, the invention provides a kit for identifying a PKD patient, the kit comprising at least one isolated first nucleic acid and at least one isolated second nucleic acid, where the first nucleic acid is selected from the group of SEQ ID NOs. 1–49 and their complementary sequences, and the second nucleic acid has an opposite orientation from the first nucleic acid, and where the first and second nucleic acids amplify a fragment of a template nucleic acid comprising a sequence of SEQ ID NO. 1 or 2, and packaging materials therefore.

In one embodiment, the kit of the invention further comprises at least one component selected from the group consisting of: a DNA polymerase, a template nucleic acid, a restriction enzyme, a control oligonucleotide primer, ddNTPs, a PCR reaction buffer and the combination thereof.

Preferably, the template nucleic acid in the kit is a genomic DNA or cDNA molecule.

BRIEF DESCRIPTION OF THE DRAWINGS

The objects and features of the invention can be better understood with reference to the following detailed description and accompanying drawings.

FIG. 1 is a figure showing the PKD1 cDNA sequence (GenBank Accesion No. L33243) used in one embodiment of the invention. Exon and PCR product junctions are depicted above the nucleotide sequence. Amino acids are positioned under the center of each codon.

FIG. 2 is a figure showing the comparison of exon sequences of a PKD gene and two homologue sequences according to one embodiment. Restriction enzyme sites which only cleave in either PKD or homologue sequence are indicated.

FIG. 11 is a table summarizing DHPLC (WAVE) conditions used in some embodiments of the invention.

FIG. 12 is a table summarizing PCR conditions used in some embodiments of the invention.

DETAILED DESCRIPTION OF THE INVENTION

Figure 3:
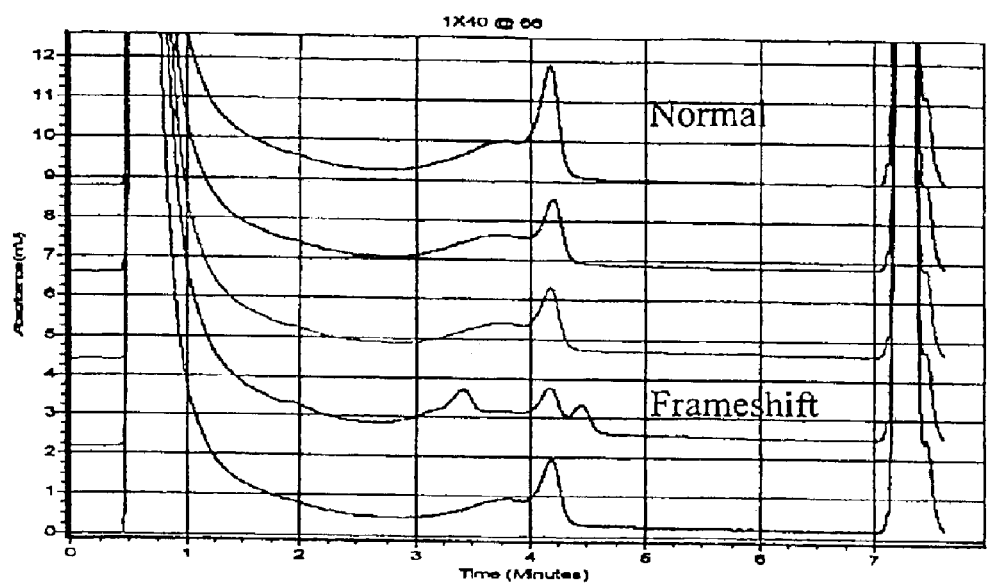
FIG. 3 is a graph showing PKD1 exon 40 DHPLC patterns of 4 normal samples and a 19 bp insertion (duplication) at nucleotide 11606, codon 3799 according to one embodiment.

The subject invention is based on the identification of unique sites within a PKD gene, the design of PKD-specific primers and the DHPLC analysis of PCR products amplified by using these PKD-specific primers.

I. Definitions

As used herein, "ADPKD" refers to autosomal dominant polycystic kidney disease. ADPKD is an exceptionally common hereditary nephropathology and is characterized by the development of renal cysts and, ultimately, renal failure, and may alternatively or in addition involve cysts in other organs including liver and spleen, as well as gastrointestinal, cardiovascular, and musculoskeletal abnormalities.

The term "PKD gene" refers to a genomic DNA sequence which maps to chromosomal position 16p13.3 (i.e., PKD-1) or chromosomal position 4q21-23 (i.e., PKD-2) and gives rise to a messenger RNA molecule encoding a PKD protein. The PKD-1 and PKD-2 genes comprise the sequences of SEQ ID NO. 1 and SEQ ID NO.2, respectively, which include introns and putative regulatory sequences. Like many other genes, PKD-1 and PKD-2 gene sequences, when compared among individuals, show sequence variations. Those genes having polymorphisms which are silent (i.e., with respect to gene expression or function of a gene product) are "normal" genes as defined herein.

A "normal" PKD gene (e.g., PKD-1 or PKD-2) is defined herein as a PKD gene such as described by SEQ ID NO. 1 or 2, respectively, and includes any gene having silent polymorphisms.

A "mutant" PKD gene is defined herein as a PKD gene (e.g., PKD-1 or PKD-2) whose sequence is modified by mutation comprising one or more substitutions (transitions or transversions), deletions (including loss of locus), insertions (including duplications), translocations, and/or other modifications relative to the normal PKD gene. The mutation causes detectable changes in the expression or function of the PKD gene product, and is causative for ADPKD. The mutations may involve from one to as many as several thousand nucleotides, and result in one or more of a variety of changes in PKD gene expression (e.g. decreased or increased rates of expression) or expression of a defective RNA transcript or protein product. Mutant PKD genes encompass those genes whose presence in one or more copies in the genome of a human individual is associated with ADPKD.

The term "basepair mismatch" refers to any nucleic acid sequence which is not complementary to the sequence of SEQ ID. NO. 1 or 2. Therefore, basepair mismatch, according to the present invention may be caused by gene alteration or polymorphism of a normal PKD gene; or by any modifications present in a mutant PKD gene. "Basepair mismatch" may be a single nucleotide basepair mismatch or it may include a nucleic acid sequence of 2 or more nucleotides (i.e., 3, or 4, or 5, or 10, or 20, or 100, or 500 more, or up to 1000 nucleotides). The presence or absence of a mismatch, as defined herein, is indicative of the presence or absence of a potential mutation in the target nucleic acid.

The term "authentic" is used herein to denote the genomic sequence of SEQ ID. NO. 1 or 2, as well as sequences derived therefrom, and serves to distinguish these authentic sequences from "PKD homologues" (see below).

A "PKD-1 homologue" is a sequence which is closely related to PKD-1, but which does not encode an expressed PKD-1 gene product. Several examples of such homologues that map to chromosomal location 16p13.1 or 4q21-23 have been identified and sequenced. A PKD-1 homologue may share more than 95% sequence identity to an authentic PKD gene.

As used herein, a "specifically amplified product" is a product amplified from a fragment within an authentic PKD gene (e.g., SEQ ID NO. 1 or 2), but not from a PKD homologue. A "non-specifically amplified product" is a product amplified from a PKD homologue or other sequences due to the annealing of nucleic acid primers to a template sequence which is not completely complementary during the amplification reaction.

As used herein, a "unique site" refers to a stretch of sequence of 10–50 base pairs in length within a PKD gene which comprises at least one nucleotide different form a stretch of sequence in a PKD homologue or other sequences. One exemplary unique site comprises a sequence of 5' AGG TCC AGG GCG ACT CGC TGG 3', or 5' CAG GGC CAC ACG CGC TGG GCG 3', or their complement thereof.

As used herein, a "PKD-specific primer" refers to a nucleic acid sequence which anneals to a sequence within a PKD gene (including introns and exons) under specific stringent conditions. A PKD-specific primer, according to the invention, anneals to a unique site present in the authentic expressed PKD-1 gene or PKD-2 gene, and not to PKD homologues or other sequences under specific stringent conditions. A PKD-specific primer shares more then 95% (e.g., more than 96%, 96%, 97%, 98%, 99%, or up to 100%) sequence identity with a unique site within a PKD gene. A "PKD-specific primer" may be 10 to 60 nucleotides in length, for example, 18–52 nucleotides in length.

As used herein, the term "specific stringent condition" refers to an amplification condition which specifically allows the annealing of a PKD-specific primer to a sequence within a PKD gene. Under a "specific stringent condition", a PKD-specific primer does not anneal to a PKD homologue or other sequences. For example, one specific stringent condition useful to the invention comprises a Taq Precision buffer (TaqPlus Precision buffer, Stratagene, La Jolla, Cat #600210), a dNTP concentration of more than 50 nM, for example, 100 nM, 200 nM, or 300 nM. The annealing temperature in a specific stringent condition may be higher than or less than or equal to 5° C. below the lowest primer annealing temperature (Tm), for example, 1° C., 2° C., 4° C., 5° C., or 10° C. higher than Tm or 4° C., 3° C., 2° C., or 1° C. below Tm.

"Amplification" of DNA as used herein refers to a reaction that serves to increase the concentration of a particular DNA sequence within a mixture of DNA sequences. Amplification may be carried out using polymerase chain reaction (PCR), ligase chain reaction (LCR), nucleic acid-specific based amplification (NSBA), or any other method known in the art.

"RT-PCR" as used herein refers to coupled reverse transcription and polymerase chain reaction. This method of amplification uses an initial step in which a specific oligonucleotide, oligo dT, or a mixture of random primers is used to prime reverse transcription of RNA into single-stranded cDNA; this cDNA is then amplified using standard amplification techniques e.g. PCR.

A "template nucleic acid" or a "target nucleic acid" (e.g., a genomic DNA or a cDNA), is a normal (e.g., wild type) or a mutant nucleic acid that is or includes a particular sequence (e.g. a PKD-1 or PKD-2 gene sequence). It will be understood that additional nucleotides may be added to the 5' and/or 3' terminus of the disclosed sequence, as part of routine recombinant DNA manipulations. Furthermore, conservative DNA substitutions i.e. changes in the sequence of the protein-coding region that do not change the encoded amino acid sequence, also may be accommodated.

As used herein, "nucleic acid primer" refers to a DNA or RNA molecule capable of annealing to a nucleic acid template and providing a 3' end to produce an extension product which is complementary to the nucleic acid template. The nucleic acid template is catalyzed to produce a primer extension product which is complementary to the target nucleic acid template. The conditions for initiation and extension include the presence of four different deoxyribonucleoside triphosphates and a polymerization-inducing agent such as DNA polymerase or reverse transcriptase, in a suitable buffer ("buffer" includes substituents which are cofactors, or which affect pH, ionic strength, etc.) and at a suitable temperature. The primer according to the invention may be single or double stranded. The primer is single-stranded for maximum efficiency in amplification, and the primer and its complement form a double-stranded nucleic acid. But it may be double stranded. "Primers" useful in the present invention are less than or equal to 100 nucleotides in length, e.g., less than or equal to 90, or 80, or 70, or 60, or 50, or 40, or 30, or 20, or 15, or equal to 10 nucleotides in length.

As used herein, the term "opposite orientation", when referring to primers, means that one primer comprises a nucleotide sequence complementary to the sense strand of a target nucleic acid template, and another primer comprises a nucleotide sequence complementary to the antisense strand of the same target nucleic acid template. Primers with an opposite orientation may generate a PCR amplified product from matched nucleic acid template to which they complement. Two primers with opposite orientation may be referred to as a reverse primer and a forward primer.

As used herein, the term "same orientation", means that primers comprise nucleotide sequences complementary to the same strand of a target nucleic acid template. Primers with same orientation will not generate a PCR amplified product from matched nucleic acid template to which they complement.

Alternatively, primers of the present invention may be labeled with a detectable label such as a radioactive moiety, or a fluorescent label, or alternatively, the amplification reaction may incorporate labeled nucleotides into the reaction product. Thus, the amplification reaction product may be "detected" by "detecting" the fluorescent or radioactive label.

As used herein, a "nucleic acid" generally refers to any polyribonucleotide or polydeoxyribonucleotide, which may be unmodified RNA or DNA or modified RNA or DNA. "Nucleic acids" include, without limitation, single- and double-stranded nucleic acids. As used herein, the term "nucleic acid(s)" also includes DNAs or RNAs as described above, that contain one or more modified bases. Thus, DNAs or RNAs with backbones modified for stability or for other reasons are "nucleic acids". The term "nucleic acids" as it is used herein embraces such chemically, enzymatically or metabolically modified forms of nucleic acids, as well as the chemical forms of DNA and RNA characteristic of viruses and cells, including for example, simple and complex cells.

As used herein, "isolated" or "purified" when used in reference to a nucleic acid means that a naturally occurring sequence has been removed from its normal cellular (e.g., chromosomal) environment or is synthesized in a non-natural environment (e.g., artificially synthesized). Thus, an "isolated" or "purified" sequence may be in a cell-free solution or placed in a different cellular environment. The term "purified" does not imply that the sequence is the only nucleotide present, but that it is essentially free (about 90–95%, up to 99–100% pure) of non-nucleotide or nucleic acid material naturally associated with it, and thus is distinguished from isolated chromosomes.

As used herein, "genomic DNA" refers to chromosomal DNA, as opposed to complementary DNA copied from an RNA transcript. "Genomic DNA", as used herein, may be all of the DNA present in a single cell, or may be a portion of the DNA in a single cell.

As used herein, "complementary" refers to the ability of a single strand of a nucleic acid (or portion thereof) to hybridize to an anti-parallel nucleic acid strand (or portion thereof) by contiguous base-pairing between the nucleotides (that is not interrupted by any unpaired nucleotides) of the anti-parallel nucleic acid single strands, thereby forming a double-stranded nucleic acid between the complementary strands. A first nucleic acid is said to be "completely complementary" to a second nucleic acid strand if each and every nucleotide of the first nucleic acid forms base-pairing with nucleotides within the complementary region of the second nucleic acid. A first nucleic acid is not completely complementary to the second nucleic acid if one nucleotide in the first nucleic acid does not base pair with the corresponding nucleotide in the second nucleic acid.

As used herein, a "sample" refers to a biological material which is isolated from its natural environment and containing target nucleic acid, and may consist of purified or isolated nucleic acid, or may comprise a biological sample such as a tissue sample, a biological fluid sample, or a cell sample comprising target nucleic acid.

As used herein, a "double stranded DNA" is referred to as a "duplex". When the base sequence of one strand is entirely complementary to base sequence of the other strand, the duplex is called a "homoduplex". When a duplex contains at least one base pair which is not complementary, the duplex is called a "heteroduplex". In the subject invention, the formation of a heteroduplex, when amplified products from a sample taken from an individual are denatured and re-annealed, indicates the presence of a potential mutant PKD gene in that individual.

As used herein, "DHPLC" refers to a separation process called "denaturing high performance liquid chromatography" which has been used to detect sequence variants by separating a heteroduplex (resulting from the presence of a mutation) and a homoduplex having the same bp length. This separation is based on the fact that a heteroduplex has a lower melting temperature (Tm) than a homoduplex. DHPLC can separate heteroduplexes that differ by as little as one base pair under certain conditions. DHPLC can also be used to separate duplexes having different bp in length.

The "heteroduplex site separation temperature" or "midpoint temperature" or "Tm" is defined herein to mean, the temperature at which one or more base pairs denature, i.e., separate, at the site of base pair mismatch in a heteroduplex DNA fragment.

II. General Description of PKD Genes

The PKD-1 gene (e.g., genbank accession number L39891, SEQ ID NO. 1) spans about 54 kb of genomic DNA on chromosome 16 (16p13.3) and contains a 12,906 bp coding sequence divided into 46 exons from which a 14 kb mRNA is transcribed (Mochizuki et al., 1996, Science, 272:1339–1342; Hughes et al., 1995, Nature Genet. 10:151–160). The protein product of PKD-1, Polycystin-1, is a 4303 amino acid protein with a predicted mass of 460 kDa. Until recently, analysis of the PKD-1 gene had not been amenable to genetic analysis largely because of the presence of at least three highly homologous copies of the gene that map proximal to PKD-1 along chromosome 16 (16p13.1). Approximately 75% of the PKD-1 gene is duplicated and shares about 97% identity with its homologous copies. The reiterated region encompasses a 50 kb (5') portion of the gene containing the first 33 exons. Only the most 3', 5.7 kb of the gene, containing exons 34–46, is unique to PKD-1. Another notable feature of the PKD-1 gene is a polypyrimidine tract in intron 21 that is 2.5 kb long, the longest described in the human genome. The PKD-2 gene (e.g., genbank accession number AF004859-004873, SEQ ID NO. 2) spans 68 kb of genomic DNA and is located on chromosome 4 (4q21-23) (Mochizuki et al., 1996, supra). PKD-2 contains 15 exons and encodes a 5.4 kb transcript from which a 968-amino acid protein product of approximately 110 kDa is generated. Mutation analysis of PKD-2 is to a great extent easier than that of PKD-1 because PKD-2 is a single copy gene. See Table 1 for a summary of PKD genes and their protein products.

TABLE 1

PKD gene description

| Gene Description | PKD-1 | PKD-2 |
| --- | --- | --- |
| Chromosome | 16p13.3 | 4q21–23 |
| Genomic length | 54 kb | 68 kb |
| Exons | 46 | 15 |
| Base pairs | 12909 | 2904 |
| Codons | 4303 | 968 |
| Protein | Polycystin-1 | Polycystin-2 |

Based on evidence supporting the occurrence of somatic mutations on the normal allele, a two-hit model similar to the pathogenesis of the many familial cancer predisposition syndromes has been proposed to explain the clinically focal manifestations of the disease (Qian et al., 1996, Cell, 87:979–987; Watnick et al., 1998Mol. Cell. 2:247–251). Briefly, the model suggests that ADPKD is recessive at the cellular level and that a second somatic mutation or "hit" in a heterozygous PKD defective background would result in the homozygous loss of PKD function in the affected renal tubular epithelial cell. The loss of PKD function is postulated to disrupt the signaling mechanisms required for proper cell differentiation and in turn leads to the abnormal proliferation of the afflicted cell into cystic structures.

Direct sequencing of the PKD-1 gene has revealed the presence of polymorphism in normal individuals and a multitude of different sequence alterations in ADPKD affected individuals. Table 2 shows a sypnosis of the PKD-1 sequence alterations described in the literature to date.

TABLE 2

Published pkd-1 sequence alterations
including mutations and polymorphisms*

| Codon Number | Nucleotide Number | Fragment number | Nucleotide Change | Amino Acid Change | Consequence |
| --- | --- | --- | --- | --- | --- |
|  |  | Intron 1-Exon 5 | 3kb del |  |  |
| 5 | 224 | 1 | 13del |  | frameshift |
| 88 | 474 | 2 | GCG-GTG | Ala-Val |  |
| 92 | 487 | 2 | GCG-GCA | Ala-Ala | polymorphism |
| 225 | 885 | 5A + 5B | TCG-TAG | Ser-X | termination |
| 227 | 890 | 5A + 5B | CAG-TAG | Gln-X | termination |
| 230 | 900 | 5A + 5B | TGC-TTC | Cys-Phe |  |
| 324 | 1182 | 5B + 5C | CGC-CTC | Arg-Leu |  |
| 341 | 1234 | 5C | GCC-GCT | Ala-Ala | polymorphism |
| 373 | 1330 | 5C | CTT-CTC | Leu-Leu | polymorphism |

TABLE 2-continued

Published pkd-1 sequence alterations
including mutations and polymorphisms*

| Codon Number | Nucleotide Number | Fragment number | Nucleotide Change | Amino Acid Change | Consequence |
|---|---|---|---|---|---|
| 403 | 1420 | 6 | CAC-CAT | His-His | polymorphism |
|  |  | 7 | CAG-CAA | splice acceptor | skip exon 7 |
| 570 | 1921 | 8 | CAC-CAT | His-His | polymorphism |
|  |  | 9 | CAG-CAT | splice acceptor | skip exon 9 |
| 695 | 2296 | 10 | C del = ccc-cc^g | Pro-Pro | frameshift |
| 695 | 2296 | 10 | C ins = ccc-cc^c | Pro-Pro | frameshift |
| 705 | 2324 | 11A | CAG-TAG | Gln-X | termination |
| 738 | 2425 | 11A | CCC-CCG | Pro-Pro | polymorphism |
| 749 | 2457 | 11A | TCA-TGA | Ser-X | termination |
| 845 | 2745 | 11B | TTG-TCG | Leu-Ser |  |
| 898 | 2905 | 11B + 11C | GCA-GCC | Ala-Ala | polymorphism |
| 900 | 2911 | 11B + 11C | CCG-CCA | Pro-Pro | polymorphism |
| 910 | 2941 | 11B + 11C | GAC-GAT | Asp-Asp | polymorphism |
| 967 | 3110 | 12 | TGG-CGG | Trp-Arg |  |
| 991 | 3183 | 12 | GTC-GGC | Val-Val | polymorphism |
|  |  | 13 | AGC-TGC | splice acceptor | skip exon 13 |
| 1003 | 3220 | 13 | 4bp del = agc-ag^g | Ser-Arg | frameshift |
| 1021 | 3274 | 13 | GGT-GGC | Gly-Gly | polymorphism |
| 1037 | 3322 | 13 | CTA-CTG | Leu-Leu | polymorphism |
| 1041 | 3336 | 13 | del g = ggc-g^cg | Gly-Ala | frameshift |
|  |  | 14 | AGG-AAG | splice acceptor | skip exon 14 |
| 1092 | 3486 | 14 | CAT-CAC | His-His | polymorphism |
| 1124 | 3583 | 15A | GCC-GCT | Ala-Ala | polymorphism |
| 1125 | 3586 | 15A | TCC-TCT | Ser-Ser | polymorphism |
| 1166 | 3707 | 15A + 15B | GGC-AGC | Gly-Ser | probable path. |
| 1198 | 3804 | 15B | 7bp del = agc-a^gg | Ser-Arg | frameshift |
| 1288 | 4075 | 15C + 15D | CAC-CAT | His-His | polymorphism |
| 1289 | 4077 | 15C + 15D | t del = gtg-g^gc | Val-Gly | frameshift |
| 1309 | 4137 | 15D | ct del = cct-c^ga | Pro-Arg | frameshift |
| 1346 | 4249 | 15D | ac del = aca-ac^a | Thr-Thr | frameshift |
| 1360 | 4291 | 15D + 15E | g del = gtg-gt^c | Val-Val | frameshift |
| 1399 | 4406 | 15E | TGG-CGG | Trp-Arg |  |
| 1525 | 4784 | 15G | g del = gtt-^tta | Val-Leu | frameshift |
| 1537 | 4820 | 15G | GAG-TAG | Glu-X | termination |
| 1545 | 4846 | 15G | AAG-AAA | Lys-Lys | polymorphism |
| 1555 | 4876 | 15G + 15H | GCA-GCC | Ala-Ala | polymorphism |
| 1558 | 4885 | 15G + 15H | ACG-ACA | Thr-Thr | polymorphism |
| 1563 | 4898 | 15G + 15H | t ins = aat-a^ta | Asn-Ile | frameshift |
| 1633 | 5109 | 15I | t ins = gag-gatg | Glu-Asp | frameshift |
| 1653 | 5168 | 15I | CAG-TAG | Gln-X | termination |
| 1672 | 5225 | 15I + 15J | a del = agg-^ggg | Arg-Gly | frameshift |
| 1672 | 5225 | 15I + 15J | ag del = agg-^ggg | Arg-Gly | frameshift |
| 1724 | 5383 | 15J | ACC-ACT | Thr-Thr | polymorphism |
| 1786 | 5566 | 15J = 15K | CCG-CTG | Pro-Leu |  |
| 1787 | 5570 | 15J + 15K | CTG-TTG | Leu-Leu | polymorphism |
| 1826 | 5689 | 15K | TGG-TGA | Trp-X | termination |
| 1829 | 5696 | 15K | CTG-TTG | Leu-Leu | polymorphism |
| 1858 | 5783 | 15K | g del = gat-^atg | Asp-Met | frameshift |
| 1874 | 5833 | 15K | TGG-TGA | Trp-X | termination |
| 1887 | 5870 | 15K | 14del = ccatc-cc^gct | Ile-Val | frameshift |
| 1921 | 5974 | 15L | CTG-CTA | Leu-Leu | polymorphism |
| 1922 | 5975 | 15L | CAG-TAG | Gln-X | termination |
| 1938 | 6024 | 15L | 1 bp ins = cac-ca^** | His-** | frameshift |
| 1949 | 6058 | 15L | AGC-AGT | Ser-Ser | polymorphism |
| 1956 | 6078 | 15L | GTG-GAG | Val-Glu | probable path. |
| 1960 | 6089 | 15L | CAG-TAG | Gln-X | termination |
| 1992 | 6187 | 15L | 4bp del = ttc-tt^ | ** | frameshift |
| 1995 | 6195 | 15L | CGC-CAC | Arg-His | polymorphism |
| 2039 | 6326 | 15M + 15L | CAG-TAG | Gln-X | termination |
| 2075 | 6434 | 15M | 28bp del |  | frameshift |
| 2144 | 6642 | 15M | 27bp del |  | frameshift |
| 2163 | 6698 | 15M | CGA-TGA | Arg-X | termination |
| 2192 | 6785 | 15M + 15N | 7bp del = acc-^gct | Thr-Ala | frameshift |
| 2220 | 6868 | 15N | 15bp del = cgg-^gtg | Arg-Val | in frame deletion |
| 2222 | 6876 | 15N | GCG-GTG | Ala-Val |  |
| 2229 | 6898 | 15N | TGC-TGA | Cys-X | termination |
| 2242 | 6937 | 15N | ac del = aca-ac^a | Thr-Thr | frameshift |
| 2243 | 6938 | 15N | CAG-TAG | Gln-X | termination |
| 2250 | 6960 | 15N | ACG-ATG | Thr-Met |  |
|  |  | 15 | GGT-GGG | splice donor |  |
|  |  | 16 | CAG-GAG | splice acceptor | skip exon 16 |
| 2309 | 7138 | 16 | GGC-GGT | Gly-Gly | polymorphism |

TABLE 2-continued

Published pkd-1 sequence alterations
including mutations and polymorphisms*

| Codon Number | Nucleotide Number | Fragment number | Nucleotide Change | Amino Acid Change | Consequence |
| --- | --- | --- | --- | --- | --- |
| 2113 | 7147 | 16 | GCG-GCA | Ala-Ala | polymorphism |
| 2323 | 7179 | 16 | 14bp del = gtc-gt^ | Val-X | termination |
| 2329 | 7196 | 16 | CGG-TGG | Arg-Trp | |
| 2332 | 7205 | 16 | 7del = gct-^tgg | Ala-Trp | frameshift |
| 2334 | 7211 | 16 | 7ins = gtg- gtg | Val-Val | frameshift |
| 2336 | 7219 | 16 | TAC-TAA | Tyr-X | termination |
| | | 17 | CAG-GAG | splice acceptor | skip exon 17 |
| 2370 | 7321 | 17 | TGT-TGA | Cys-X | termination |
| 2371 | 7324 | 17 | gt del = gtg-gt^c | Val-Val | frameshift |
| 2378 | 7345 | 17 | GTG-GTT | Val-Val | polymorphism |
| 2379 | 7347 | 17 | TAC-TGC | Tyr-Cys | |
| 2389 | 7376 | 17 | TTG-CTG | Leu-Leu | polymorphism |
| 2392 | 7386 | 17 | CGC-CCC | Arg-Pro | |
| 2396 | 7397 | 17 | 11bp ins = att-^ttg | Ile-Leu | frameshift |
| 2402 | 7415 | 17 | CGA-TGA | Arg-X | termination |
| 2408 | 7433 | 18 | CGT-TGT | Arg-Cys | probable path. |
| 2423 | 7479 | 18 | TCC-TTC | Ser-Phe | |
| 2430 | 7499 | 18 | CGA-TGA | Arg-X | termination |
| 2442 | 7535 | 18 | 3bp ins = gag-g^gcg | Glu-Gly | probable path. |
| 2471 | 7623 | 18 | CCG-CTG | Pro-Leu | |
| 2481 | 7652 | 18 | CTG-TTG | Leu-Leu | polymorphism |
| 2495 | 7696 | 18 | TGC-TGT | Cys-Cys | polymorphism |
| 2519 | 7767 | 19 | CAG-CTG | Gln-Leu | |
| 2548 | 7853 | 19 | GAG-CAG | Glu-Gln | polymorphism |
| 2558 | 7883 | 19 | CAG-TAG | Gln-X | termination |
| 2570 | 7919 | 20 | TTG-CTG | Leu-Leu | polymorphism |
| 2579 | 7945 | 20 | ggc del = ggc-^agc | Gly-Ser | Gly del in frame |
| 2582 | 7956 | 20 | ACG-ATG | Thr-Met | polymorphism |
| 2597 | 8002 | 20 | CCA-CCG | Pro-Pro | polymorphism |
| 2604 | 8021 | 20 | GAT-AAT | Asp-Asn | polymorphism |
| 2607 | 8030 | 20 | 5bp del = cac-^cat | His-His | frameshift |
| 2612 | 8046 | 20 | gtt del = tcgtt-tc^g | Ser-Ser | Leu del in frame |
| 2638 | 8124 | 21 | CAC-CGC | His-Arg | polymorphism |
| 2639 | 8126 | 21 | CGA-TGA | Arg-X | termination |
| 2639 | 8126 | 21 | 20 ins = cga-c^**** | Arg-** | frameshift |
| 2649 | 8157 | 21 | ACT-ATT | Thr-Ile | |
| 2650 | 8159 | 21 | del ct = ctg-^ggt | Leu-Gly | frameshift |
| 2658 | 8183 | 21 | 8bp del | Val-X | termination |
| 2674 | 8231 | 22 | CCC-TCC | Pro-Ser | polymorphism |
| 2696 | 8298 | 22 | CTC-CGC | Leu-Arg | |
| 2708 | 8334 | 22 | ACG-ATG | Thr-Met | |
| 2734 | 8411 | 23A | CCA-ACA | Pro-Thr | polymorphism |
| 2735 | 8415 | 23A | CAG-CTG | Gln-Leu | polymorphism |
| 2745 | 8446 | 23A | TCT-TCG | Ser-Ser | polymorphism |
| 2760 | 8490 | 23A | ATG-ACG | Met-Thr | |
| 2761 | 8493 | 23A | CGC-CCC | Arg-Pro | |
| 2763 | 8498 | 23A | CTC-GTC | Leu-Val | |
| 2764 | 8502 | 23A | ATG-ACG | Met-Thr | |
| 2765 | 8504 | 23A | CGC-TGC | Arg-Cys | polymorphism |
| 2766 | 8507 | 23A | 12bp ins/dup | | in frame mutation |
| 2782 | 8556 | 23A | GTG-ATG | Val-Met | polymorphism |
| 2791 | 8583 | 23A + 23B | CGG-CAG | Arg-Gln | |
| 2813 | 8650 | 23A + 23B | AGC-AGT | Ser-Ser | polymorphism |
| 2814 | 8651 | 23A + 23B | GGG-AGG | Gly-Arg | polymorphism |
| 2815 | 8657 | 23A + 23B | c del = gcc-g^cc | Ala-Ala | frameshift |
| 2826 | 8688 | 23B + 23C | ATC-ACC | Ile-Thr | |
| 2888 | 8873 | 23C | CGC-GGC | Arg-Gly | polymorphism |
| 2893 | 8890 | 23C | TCC-TCG | Ser-Ser | polymorphism |
| 2900 | 8909 | 23C | CAG-TAG | Gln-X | termination |
| 2905 | 8924 | 23C | GTC-ATC | Val-Ile | polymorphism |
| 2921 | 8973 | 23C | CAT-CCT | His-Pro | |
| 2966 | 9109 | 24 | GAG-GAC | Glu-Asp | polymorphism |
| 2971 | 9124 | 24 | GCT-GCC | Ala-Ala | polymorphism |
| 2972 | 9125 | 24 | GAC-AAC | Asp-Asn | polymorphism |
| 2978 | 9142 | 24 | ttc del | del of Phe | in frame deletion |
| 2985 | 9164 | 25 | AGA-GGA | Arg-Gly | |
| 2988 | 9175 | 25 | GCG-GCA | Ala-Ala | polymorphism |
| 2993 | 9189 | 25 | CTG-CCG | Leu-Pro | probable path. |
| 3001 | 9213 | 25 | TGG-TAG | Trp-X | termination |

TABLE 2-continued

Published pkd-1 sequence alterations
including mutations and polymorphisms*

| Codon Number | Nucleotide Number | Fragment number | Nucleotide Change | Amino Acid Change | Consequence |
|---|---|---|---|---|---|
| 3008 | 9233 | 25 | GTG-CTG | Val-Leu | |
| 3012 | 9245 | 25 | 18bp del | | in frame deletion |
| 3016 | 9258 | 25 | CAG-CGG | Gln-Arg | probable path. |
| 3020 | 9269 | 25 | GAG-TAG | Glu-X | termination |
| 3030 | 9299 | 25 | c del = ctg-^tgc | Leu-Cys | frameshift |
| 2985 | 9326 | 25 | CGC-TCG | Arg-Cys | |
| 3052 | 9367 | 25 | GGC-GGT | Gly-Gly | polymorphism |
| 3064 | 9401 | 25 | TTT-CTT | Phe-Leu | |
| 3065 | 9406 | 25 | GTTT-CCTT | Phe-Leu | polymorphism |
| 3065 | 9406 | 25 | GTG-GTC | Val-Val | polymorphism |
| 3066 | 9407 | 25 | TTT-CTT | Phe-Leu | polymorphism |
| 3090 | 9481 | 26 | GTC-GTT | Val-Val | polymorphism |
| 3110 | 9541 | 26 | CCT-CCC | Pro-Pro | polymorphism |
| 3139 | 9627 | 27 | GGC-TGC | Gly-Cys | |
| 3180 | 9751 | 27 | TGG-TGA | Trp-X | termination |
| 3193 | 9789 | 28 | CCT-CTT | Pro-Leu | |
| 3206 | 9827 | 28 | CAG-TAG | Gln-X | termination |
| 3219 | 9867 | 28 | t del = ctt-c^tt | Leu-Leu | frameshift |
| 3223 | 9880 | 28 | ACG-ACA | Thr-Thr | polymorphism |
| 3285 | 10064 | 29 | GTT-ATT | Val-Ile | |
| 3311 | 10143 | 30 | CAT-CGT | His-Arg | |
| 3341 | 10234 | 30 | CTT-CTC | Leu-Leu | polymorphism |
| 3348 | 10255 | 30 | CGG-CGT | Arg-Arg | polymorphism |
| 3350 | 10262 | 31–34 | 2kb del | | frameshift after 3350 |
| 3375 | 10334 | 31 | GTG-ATG | Val-Met | |
| | | IVS31 + 25del19 | | | frameshift after 3389 |
| 3394 | 10391 | 32 | CAG-TAG | Gln-X | termination |
| | | 34–3'UTR | 5.5kb del | | |
| 3474 | 10631 | 34 | CAG-TAG | Gln-X | termination |
| 3509 | 10737 | 35 | ACG-ATG | Thr-Met | polymorphism |
| 3510 | 10739 | 35 | CTG-GTG | Leu-Val | probable path. |
| 3511 | 10743 | 35 | GCG-GTG | Ala-Val | |
| 3513 | 10748 | 35 | CAG-TAG | Gln-X | termination |
| 3561 | 10893 | 36 | AGC-AAC | Ser-Asn | probable poly. |
| 3579 | 10947 | 36 | t ins = ttc-tt^t | Phe-Phe | frameshift |
| 3589 | 10976 | 36 | CTG-TTG | Leu-Leu | polymorphism |
| | IVS37-10C-A | intron 37 | | | unknown poly |
| 3631 | 11104 | 37 | GAG-GAC | Glu-Asp | |
| 3677 | 11241 | 38 | ATG-ACG | Met-Thr | |
| 3692 | 11284 | 38 | t ins = ggc-gg^t | Gly-Gly | frameshift |
| 3692 | 11285 | 38 | c ins = tca-^ctc | Ser-Leu | frameshift |
| 3711 | 11342 | 38 | CGG-GGG | Arg-Gly | frameshift |
| 3747 | 11449 | 39 | 15bp del = cgg-^cgg | Arg-Arg | in frame deletion |
| 3749 | 11457 | 39 | 15bp del = gcg-^cag | Arg-Gln | in frame deletion |
| 3752 | 11466 | 39 | CGG-CAG | Arg-Gln | |
| | | IVS39 + 1G-C | Ggt-Gct | splice donor | |
| | | I39E40–25 to I39E40 + 47 | 72bp del | | |
| 3370 | 11521 | 40 | TCG-TCA | Ser-Ser | polymorphism |
| 3780 | 11549 | 40 | 10bp ins = tac-t^ac | Tyr-Tyr | frameshift |
| 3781 | 11554 | 40 | GAC-GAT | Asp-Asp | polymorphism |
| 3791 | 11584 | 40 | TCG-TCC | Ser-Ser | polymorphism |
| 3794 | 11592 | 40 | TGG-TAG | Trp-X | termination |
| | IVS41-11C-T | intron 41 | | | unknown poly |
| 3818 | 11665 | 41 | TAC-TAA | Tyr-X | termination |
| 3820 | 11669 | 41 | CAG-TAG | Gln-X | termination |
| 3837 | 11720 | 41 | CAG-TAG | Gln-X | termination |
| 3971 | 12124 | 43 | CGC-CGT | Arg-Arg | polymorphism |
| 3984 | 12163 | 43 | TCC-TCG | Ser-Ser | polymorphism |
| 3985 | 12165 | 43 | GCA-GGA | Ala-Glu | |
| 3985 | 12168 | 43 | GCC-GGG | Ala-Gly | probable poly. |
| 3991 | 12184 | 43 | GCC-GCG | Ala-Ala | polymorphism |
| | 12187 | 43 | 9bp ins | | in frame |
| | | IVS43 + 14del20 | | | complex splicing |
| | | IVS43 + 17del18 | | | complex |

TABLE 2-continued

Published pkd-1 sequence alterations
including mutations and polymorphisms*

| Codon Number | Nucleotide Number | Fragment number | Nucleotide Change | Amino Acid Change | Consequence |
|---|---|---|---|---|---|
| | | 44 | CAG-CAC | splice acceptor | splicing skip exon 44 |
| 4010 | 12239 | 44 | CAG-TAG | Gln-X | termination |
| 4011 | 12244 | 44 | TGG-TGA | Trp-X | termination |
| 4014 | 12252 | 44 | tt del = ttt-t^gg | Phe-Trp | frameshift |
| 4017 | 12262 | 44 | at del = aca-ac^t | Thr-Thr | frameshift |
| 4020 | 12269 | 44 | CGA-TGA | Arg-X | termination |
| 4024 | 12281 | 44 | GAG-TAG | Glu-X | termination |
| 4027 | 12290 | 44 | g ins = ggg-gg^g | Gly-Gly | frameshift |
| 4031 | 12303 | 44 | GGC-GAC | Gly-Asp | |
| 4032 | 12307 | 44 | CTG-CTC | Leu-Leu | polymorphism |
| 4039 | 12328 | 44 | TAC-TAA | Tyr-X | termination |
| 4041 | 12332 | 44 | CAG-TAG | Gln-X | termination |
| 4044 | 12341 | 44 | ATC-GTC | Ile-Val | probable poly. |
| | | 44 | GGT-GCT | splice donor | del of 4001–4045 |
| | | 45 | CAG-CAA | splice acceptor | skip exon 45 |
| 4058 | 12384 | 45 | GCC-GTC | Ala-Val | probable poly. |
| 4059 | 12386 | 45 | CAG-TAG | Gln-X | termination |
| 4069 | 12416 | 45 | 20bp ins = ggg-g^**** | Gly-** | frameshift |
| 4075 | 12438 | 45 | 20bp ins = gcc-gc^g | Ala-Ala | frameshift |
| 4086 | 12469 | 45 | TGT-TGA | Cys-X | termination |
| 4091 | 12483 | 45 | GCA-GCG | Ala-Ala | polymorphism |
| 4101 | 12511 | 45 | g ins = -ggg-gg^g | Gly-Gly | frameshift |
| 4124 | 12581 | 45 | CAG-TAG | Gln-X | termination |
| 4126 | 12589 | 45 | TAC-TAG | Tyr-X | termination |
| 4131 | 12601 | 45 | gtt del = gagtt-ga^gtt | Leu-Phe | frameshift |
| 4135 | 12614 | 45 | AGG-GGG | Arg-Gly | |
| 4136 | 12617 | 45 | CTG-TTG | Leu-Leu | polymorphism |
| 4136 | 12617 | 45 | c del = ctg-^tgc | Leu-Cys | frameshift |
| 4139 | 12628 | 45 | TGG-TGA | Trp-X | termination |
| 4145 | 12644 | 45 | GTC-ATC | Val-Ile | probable poly. |
| | IVS45+17insG | intron 45 | | | unknown poly |
| 4153 | 12668 | 46 | CGC-TGC | Arg-Cys | |
| 4168 | 12714 | 46 | duplication of 23bp | | frameshift |
| 4176 | 12739 | 46 | a del = cca-cc^c | Pro-Pro | frameshift |
| 4189 | 12777 | 46 | TCC-TTC | Ser-Phe | polymorphism |
| 4198 | 12801 | 46 | del 28 | | frameshift |
| 4209 | 12838 | 46 | CCT-CCC | Pro-Pro | polymorphism |
| 4224 | 12882 | 46 | CAG-CCG | Gln-Pro | probable path. |
| 4227 | 12890 | 46 | CGA-TGA | Arg-X | termination |
| 4236 | 12919 | 46 | TAC-TAa/g | Tyr-X | termination |
| 4254 | 12973 | 46 | CCC-CCT | Pro-Pro | polymorphism |
| 4275 | 13034 | 46 | CGG-TGG | Arg-Trp | probable path. |

*Updated March 2001.
**is an unidentified base or amino acid.

III. Identification of Unique Sites Within PKD Genes

Due to the fact that 70% of the PKD-1 gene is replicated as non-functional homologues with more than 95% sequence identity to PKD-1, the identification of PKD-1 unique sites are critical or the development of a genetic testing method. With the successful decoding of human genome sequences, the unique sites within the PKD genes may be identified by comparing genomic DNA sequences comprising a PKD gene with genomic DNA sequences comprising a PKD homologue. Useful databases and computer programs are known in the art (e.g., databases available through NCBI at www.ncbi.nlm.nih.gov; and computer programs available at http://www.ncbi.nlm.nih.gov/BLAST and DNAStar, www.dnastar.com). A unique site refers to a stretch of sequence within a PKD gene which shares less than or equal to 80% (e.g., less than or equal to 70%, or 60%, or 50% or 40% or 30% or 20% or 10%) sequence identity to a PKD homologue or other sequences.

Several unique sites (e.g., single copy site) have been described in Rossetti et al., 2000, Am. J. Hum. Genet. 68:46–63, the entirety of which hereby incorporated by reference. A novel unique site (5' AGG TCC AGG GCG ACT CGC TGG 3', or 5' CAG GGC CAC ACG CGC TGG GCG 3', or their complement thereof) is identified for PKD-1 by Applicants of the present application. Other unique sites may be found in, for example, in U.S. Pat. Nos. 6,228,591 and 6,031,088, each of which is incorporated herein by its entirety.

The identified unique sites can be used for designing PKD-specific primers for the amplification of authentic PKD genes. The length of a unique site may vary from several nucleotides to thousands of nucleotides. Most of unique site identified comprises less than or equal to 100 nucleotides, e.g., less than or equal to 50 nucleotides, or less than or equal to 30 nucleotides. Amplification using PKD-specific primers would increase the specificity of the amplification reaction and reduce the amount by-products amplified from PKD homologues. The specifically amplified product of authentic PKD genes may be subsequently used for sequencing to identify allele variant, e.g., a mutant PKD gene, in an individual or for cloning and/or expression for other analysis.

IV. PKD-Specific Primers Useful for the Invention

Samples to be analyzed for the presence or absence of mutations often contain amounts of material too small to detect. The first step in mutation detection assays is, therefore, sample amplification. A preferred amplification reaction of the invention is PCR. PCR amplification comprises steps such as primer design, choice of DNA polymerase enzyme, the number of amplification cycles and concentration of reagents. Each of these steps, as well as other steps involved in the PCR process affects the purity of the amplified product. Although the PCR process and the factors which affect fidelity of replication and product purity are well known in the PCR art, these factors have not been addressed, heretofore, in relation to mutation detection of PKD genes using the separating method of the invention, e.g., DHPLC.

Any primer which anneals, under specific stringent conditions, to a sequence within an authentic PKD gene, but not to a PKD homologue or other sequences is a useful PKD-specific primer according to the invention. Sequences of the identified unique sites serve as the basis for designing PKD-specific primers useful according to the invention. The primers, according to the subject invention, may be incorporated into a convenient kit for identifying a PKD patient.

A. Criteria for Selecting Primers

A PKD species-specific primers preferably comprise a sequence complementary to a sequence located within a unique site of a PKD gene. The PKD-specific primer may be complementary to a unique site of a normal or a mutant PKD gene, so long as the primer preferably anneals to an authentic PKD gene other than a PKD homologue.

PKD species-specific primers may be selected manually by analyzing sequences of the unique sites identified for a PKD gene. When the sequence of a DNA fragment to be amplified by PCR is known, commercially available software can be used to design primers which will produce either the whole fragment, or any sequence within the fragment. The melting map of a fragment can be constructed using software such as MacMelt® (BioRad Laboratories, Hercules, Calif.), MELT (Lerman et al. Meth. Enzymol. 155:482 (1987)), or WinMelt™ (BioRad Laboratories).

It is known in the art that primers that are about 18–25 bases long and with 50% G-C content will work well at annealing temperature at about 52–58° C. These properties are preferred when designing primers for the subject invention. Longer primers, or primers with higher G-C contents, have annealing optimums at higher temperatures; similarly, shorter primers, or primers with lower G-C contents, have optimal annealing properties at lower temperatures. A convenient, simplified formula for obtaining a rough estimate of the melting temperature of a primer 17–25 bases long is as follows:

Melting temperature (Tm in ° C.)=4×(# of G+# of C)+2×(# of A+# of T)

The overall design process design consists of both long range (i.e., for the first round PCR) and short range primer (i.e., for the nested PCR) design. In long range primer design, the objective is to design primers that produce good quality PCR products. "Good quality" PCR products are defined herein to mean PCR products produced in high yield and having low amounts of impurities such as primer dimers and PCR induced mutations. Good quality PCR can also be affected by other reaction parameters, such as the enzyme used, the number of PCR cycles, the concentration and type of buffer used, temperature thermal cycling procedures and the quality of the genomic template. Methods for producing good quality PCR products are discussed by Eckert et al. (*PCR: A Practical Approach,* McPherson, Quirke, and Taylor eds., IRL Press, Oxford, Vol. 1, pp. 225–244, 1991). This reference and the references therein are incorporated herein in their entireties.

Short range primer design should fulfill two requirements. First, it should fulfill all the requirements of long range primer design and give good quality PCR products. In addition, it must produce fragments that allow the DHPLC method to detect a mutation or polymorphism regardless of the location of the mutation or polymorphism within the amplified fragment. For example, large DNA fragments, having up to several thousand base pairs, can be amplified by PCR. If the only goal of the amplification is to replicate the desired fragment, then there is a large latitude in the design of primers which can be used for this purpose. However, if the purpose of a PCR amplification is to produce a DNA fragment for mutation detection analysis by DHPLC, then primers must be designed such that the fragment produced in the PCR process is capable of being detected, and will produce a signal, when analyzed by DHPLC. In a preferred embodiment of the invention, the length of an amplified product is 150–600 bps. In a more preferred embodiment, the fragment length for DHPLC mutation detection analysis is 150–400 bp.

There are two goals of designing short range primers. One goal for primer design is if the analysis is used as a "mutation analysis" test. Another goal is in analysis for research or diagnostic purposes, e.g., for identifying a PKD patient. "Mutation analysis" is defined herein as the study or analysis of DNA fragments to determine if the fragments contain variations (i.e., mutations or polymorphisms) in a population and correlate that variation to disease. It is to be understood that, within the context of this invention, the term "mutation" does not include a polymorphism (e.g., normal) which is silent for the disease. When DHPLC is used as a mutation analysis technique, then an important aspect of the present invention is a method for designing primers to produce a fragment in which a putative mutation can be detected, regardless of where the mutation site is located within the fragment. If the mutation is known, on the other hand, then the primer design can be further refined so that the analysis is optimized, i.e., the resolution of the homoduplex and the heteroduplex peaks in DHPLC is maximized. By improving the resolution for the analysis of known mutations, accuracy of analysis can be performed. Improved resolution is required for diagnostic mutation applications. Furthermore, with improved resolution, automatic identification of the positive presence of mutation can be more easily implemented with appropriate software and an algorithm that overlays and comparatively measures the peaks of the normal and mutant DNA samples.

Another method of primer design for mutation analysis applications is to design the primers so that the region of interest is at a lower melting domain within the fragment. In this case the primers are preferred to be designed so that the fragment being measured will overlap the regions of interest as the analysis is performed traveling down the exon. In these cases, the temperature difference between the higher melting domain and the lower melting domain is preferred to be greater than 5° C. and most preferred to be greater than 10° C.

Once the mutation of interest is identified, primers can be redesigned for diagnostic or clinical applications. In these cases, the mutation is preferably located within 25% or 25 bases of the end whichever is closer to the end. The other end of the fragment contains a higher melting domain of preferably 5° C., more preferably 10° C. higher, and most preferably 15° C. higher than the lower domain where the mutation is located. If the primer selection does not result in a high melting domain on the opposite end of the fragment, then a G-C clamp can be applied to increase the melting temperature at the desired end (e.g., an A-T rich end) (Myers et al., 1985, Nucleic Acids Res. 13:3111). G-C clamping is a technique in which additional G or C bases are included on the 5' end of one or both of the primers. The polymerase enzyme will extend over these additional bases incorporating them into the amplified fragment thereby raising the melting temperature of the end(s) of the fragment relative to that in the vicinity of the mutation. For example, in cases where the mutation is in the center of the amplified fragment and the length is less than 100 bp and the melting profile is flat, or in cases where the mutation in a high melting region of the fragment and a higher melting region is in effect a G-C rich region, a G-C clamp may be necessary. In these cases, proper primer selection will result in a fragment in which the mutation can be detected. The size of the G-C clamp can be up to 40 bp and as little as 4 or 5 bp. The most preferred G-C clamp for mutation detection by DHPLC is 10 to 20 bp.

If it is not possible to design primers which will produce, upon PCR amplification, domains having a constant melting range or domains within a fragment which are sufficiently close in Tm, then it may be necessary to lower the Tm of a domain of interest for successful mutation detection by DHPLC. This can be done, for example, by substituting dGTP with the analog 7-deaza-2'-dGTP which is known to effectively lower the melting temperature of G-C base pairs (Dierick et al.,1993, Nucl. Acids Res. 21:4427). If it is necessary to raise the Tm of the domain, then 2, 6-aminopurine can be used in place of dGTP in the PCR amplification.

In a most preferred embodiment, the primers are selected so that the mutation is located in a "lower melting" domain of the fragment. However, a mutation can also be detected by DHPLC in a high melting domain of the fragment either if the high melting domain does not have a melting temperature that is too different from other domains in the fragment or if a higher column temperature is used that is optimized for the higher melting domain of the fragment.

The long range primer design described above can be further refined by local primer design in which several other factors should be considered. For example, primers with non-template tails, such as universal sequencing primers or T7 promoters, may need to be avoided. The preferred primer has a Tm of about 56° C. The difference in Tm between the forward and reverse primers is preferably about 1° C. The difference in Tm between primer and template is preferably 25° C. The 3'-pentomer of each primer is preferably be more stable than $\Delta G°=-6$ kcal/mol (i.e., more negative). Any possible primer dimers are preferably be less stable than the 3'-pentomer by at least 5 kcal/mol (i.e., 5 kcal more positive). Any primer self annealing loops are preferably to have a Tm of less than 12° C. Primers are preferably be of high purity without failure sequences. To avoid degradation, storage in Tris-HCl (pH 8.0) buffer is preferable to pure water.

In some embodiments, it is more convenient to directly separate a long fragment, e.g., an exon, of up to 5 kb (e.g., up to 4 kb, or up to 3kb, or up to 2 kb, or up to 1 kb) for mutations. Such long fragments generally contain multiple melting temperature domains. Double-stranded DNA fragments melt in a series of discontinuous steps as different regions with differing thermal stabilities which denature in response to increasing temperature. These different regions of thermal stability are referred to as "domains", and each domain is approximately 50–300 bp in length. Each domain has its own respective Tm and will exhibit thermodynamic behavior which is related to its respective Tm. The presence of a base mismatch within a domain will destabilize it, resulting in a decrease in the Tm of that domain in the heteroduplex relative to its fully hydrogen-bonded counterpart found in the homoduplex. Generally the presence of a base mismatch will lower the Tm by approximately 1–2° C.

In accordance with the preferred embodiments, optimal results have been obtained using primers which are 18–51 in length and DNA sequence to the primers with SEQ ID NOs. 3–49 (Table 3 and Table 4). However, one skilled in the art will recognize that the length of the primers used may vary. For example, it is envisioned that shorter primers containing at least 15, and preferably at least 17, consecutive bases of the nucleotide sequences of these primers SEQ ID NOs. 3–49 may be suitable. The exact upper limit of the length of the primers is not critical. However, typically the primers will be less than or equal to approximately 60 bases, preferably less than or equal to 50 bases. Further still, the bases included in the primers may be modified as is conventional in the art, including but not limited to, incorporating detectable labels such as biotin, or fluorescent labels.

TABLE 3

Examples of useful pkd-1 specific primers*

| SEQ ID NO. | Primer Name | Primer Sequence |
|---|---|---|
| 50 | 1X1F | 5' CGT CGC TCA GCA GCA GGT CG 3' |
| 51 | 1X1R | 5' CGT CCT GCT TCC CGT CCC G 3' |
| 52 | 1X2F | 5' GCG GCC CGC CGC CCC CGC CGT TGG GGA TGC TGG CAA TGT GTG 3' |
| 53 | 1X2R | 5' GGG ATT CGG CAA AGC TGA TG 3' |
| 54 | 1X3F | 5' TTC CAT CAG CTT TGC CGA AT 3' |
| 55 | 1X3R | 5' ATC TGG TCT CAA GCC TGG AAG 3' |

TABLE 3-continued

Examples of useful pkd-1 specific primers*

| SEQ ID NO. | Primer Name | Primer Sequence |
|---|---|---|
| 56 | 1X4F | 5' GCC CCG CGC CCG TCC CGC CGC CCC CGC CGA GAC CCT TCC CAC CAG ACC T 3' |
| 57 | 1X4R | 5' CGC CCC CGC CCG TGA GCC CTG CCC AGT GTC T 3' |
| 58 | 1X5AF | 5' GCG GCC CGC GCC CCG CGG AGC CAG GAG GAG CAG AAC CC 3' |
| 59 | 1X5AR | 5' CAG AGG GAC AGG CAG GCA AAG G 3' |
| 60 | 1X5BF | 5' GCC CCC GCC GCC CAG CCC TCC AGT GCC T 3' |
| 61 | 1X5BR | 5' ATC GCT ATG TGC TGC CTG GG 3' |
| 62 | 1X5CF | 5' CCG AGG TGG ATG CCG CTG 3' |
| 63 | 1X5CR | 5' GAA GGG GAG TGG GCA GCA GAC 3' |
| 64 | 1X6F | 5' CAC TGA CCG TTG ACA CCC TCG 3' |
| 65 | 1X6R | 5' TGC CCC AGT GCT TCA GAG ATC 3' |
| 66 | 1X7F | 5' GGA GTG CCC TGA GCC CCC T 3' |
| 67 | 1X7R | 5' CCC CTA ACC ACA GCC AGC G 3' |
| 68 | 1X8F | 5' TCT GTT CGT CCT GGT GTC CTG 3' |
| 69 | 1X8R | 5' GCA GGA GGG CAG GTT GTA GAA 3' |
| 70 | 1X9F | 5' GCG GCC CGC GCC CCG CGG GTA GGG GGA GTC TGG GCT T 3' |
| 71 | 1X9R | 5' GAG GCC ACC CCG AGT CC 3' |
| 72 | 1X10F | 5' GTT GGG CAT CTC TGA CGG TG 3' |
| 73 | 1X10R | 5' CGC CGC CCC CGC CCG GGA AGG TGG CCT GAG GAG AT 3' |
| 74 | 1X11AF | 5' GCG GCC CGC GCC CCG CGC GGG GGG TCC ACG GGC CAT G 3' |
| 75 | 1X11AR | 5' AAG CCC AGC AGC ACG GTG AG 3' |
| 76 | 1X11BF | 5' CCG CCG CCC CCG CCG CTG CCC TGC CTG TGC CCT G 3' |
| 77 | 1X11BR | 5' GCC CCG CGC CCG TCC CGC CGC CCC CGC CCG TTC CAC CAC CAC GTC CAC CAC 3' |
| 78 | 1X11CF | 5' GTG GTG GAC GTG GTG GTG GAA 3' |
| 79 | 1X11CR | 5' GGC TGC TGC CCT CAC TGG GAA 3' |
| 80 | 1X12F | 5' TAA GGG CAG AGT CCT CCA CAG 3' |
| 81 | 1X12R | 5' CCA CCC CCG CCC ACC TAC TGA G 3' |
| 82 | 1X13F | 5' GCG GCC CGC GCC CCG CCG TGG AGG AGG GAC GCC AAT C 3' |
| 83 | 1X13R | 5' GAG GCT GGG GCT GGG ACA A 3' |
| 84 | 1X14F | 5' CCC GGT TCA CTC ACT GCG 3' |
| 85 | 1X14R | 5' CCC CCG CCC GCC GTG CTC AGA GCC TGA AAG 3' |
| 86 | 1X15AF | 5' GGC GGG GGG CTT CTG CCG AGC GGG TGG GGA GCA GGT GG 3' |
| 87 | 1X15AR | 5' CGC CGC CCC CGC CCG GCT CTG GGT CAG GAC AGG GGA 3' |

TABLE 3-continued

Examples of useful pkd-1 specific primers*

| SEQ ID NO. | Primer Name | Primer Sequence |
|---|---|---|
| 88 | 1X15BF | 5' CGC CTG GGG GTG TTC TTT 3' |
| 89 | 1X15BR | 5' ACG TGA TGT TGT CGC CCG 3' |
| 90 | 1X15CF | 5' GCC CCC GCC GGG GCG CCC CCG TGG TGG TCA GC 3' |
| 91 | 1X15CR | 5' CAG GCT GCG TGG GGA TGC 3' |
| 92 | 1X15DF | 5' CTG GAG GTG CTG CGC GTT 3' |
| 93 | 1X15DR | 5' CGC CCC CGC CCG CTG GCT CCA CGC AGA TGC 3' |
| 94 | 1X15EF | 5' CGT GAA CAG GGC GCA TTA 3' |
| 95 | 1X15ER | 5' CCC CCG CCC GGC AGC AGA GAT GTT GTT GGA C 3' |
| 96 | 1X15FF | 5' CCG CCG CCC CCG CCG CCA GGC TCC TAT CTT GTG ACA 3' |
| 97 | 1X15FR | 5' TGA AGT CAC CTG TGC TGT TGT 3' |
| 98 | 1X15GF | 5' CTA CCT GTG GGA TCT GGG G 3' |
| 99 | 1X15GR | 5' TGC TGA AGC TCA CGC TCC 3' |
| 100 | 1X15HF | 5' GGG CTC GTC GTC AAT GCA AG 3' |
| 101 | 1X15HR | 5' CGC CGC CCC CGC CCG CCG CCC ACC ACC TGC AGC CCC TCT A 3' |
| 102 | 1X15IF | 5' GCG GCC CGC CGC CCC CGC CGC CGC CCA GGA CAG CAT CTT C 3' |
| 103 | 1X15IR | 5' CGC TGC CCA GCA TGT TGG 3' |
| 104 | 1X15JF | 5' GGC CGG CAG CGG CAA AGG CTT CTC 3' |
| 105 | 1X15JR | 5' GCC CAG CAC CAG CTC ACA T 3' |
| 106 | 1X15KF | 5' CGA GCC ATT TAC CAC CCA TAG 3' |
| 107 | 1X15KR | 5' GGC AGC AGC AGG ATC TGA AA 3' |
| 108 | 1X15LF | 5' CTG TGG GCC AGC AGC AAG GTG 3' |
| 109 | 1X15LR | 5' CCT GAA CCT CCA GCA CCA GCG 3' |
| 110 | 1X15MF | 5' AGG TCC AGG GCG ACT CGC TGG 3' |
| 111 | 1X15MR | 5' CAG GGC CAC ACG CGC TGG GCG 3' |
| 112 | 1X15NF | 5' TTG GAG GCC CAC GTT GAC CTG 3' |
| 113 | 1X15NR | 5' CCC CCG CCC GCA TGG GTG TGG ACG GGT GAG G 3' |
| 114 | 1X16F | 5' TAA AAC TGG ATG GGG CTC TC 3' |
| 115 | 1X16R | 5' GGC CTC CAC CAG CAC TAA 3' |
| 116 | 1X17F | 5' GGG TCC CCC AGT CCT TCC AG 3' |
| 117 | 1X17R | 5' TCC CCA GCC CGC CCA CA 3' |
| 118 | 1X18F | 5' GCC CCC TCA CCA CCC CTT CT 3' |
| 119 | 1X18R | 5' TCC CGC TGC TCC CCC CAC GCA 3' |
| 120 | 1X19F | 5' GAT GCC GTG GGG ACC GTC 3' |
| 121 | 1X19R | 5' GTG AGC AGG TGG CAG TCT CG 3' |

TABLE 3-continued

Examples of useful pkd-1 specific primers*

| SEQ ID NO. | Primer Name | Primer Sequence |
|---|---|---|
| 122 | 1X20F | 5' CCA CCC CCT CTG CTC GTA GGT 3' |
| 123 | 1X20R | 5' GGT CCC AAG CAC GCA TGC A 3' |
| 124 | 1X21F | 5' TGC CGG CCT CCT GCG CTG CTG A 3' |
| 125 | 1X21R | 5' GCG GGC AGG GTG AGC AGG TGG GGC CAT CC 3' |
| 126 | 1X22F | 5' GAG GCT GTG GGG GTC CAG TCA AGT GG 3' |
| 127 | 1X22R | 5' AGG GAG GCA GAG GAA AGG GCC GAA C 3' |
| 128 | 1X23AF | 5' CGT CCC GCC TGC ACT GAC CTC ACG CAT GT 3' |
| 129 | 1X23AR | 5' CGG CCC GCC GCC CCC GCC CGG CCA AAG GGA AAG GGA TTG GA 3' |
| 130 | 1X23BF | 5' CCG CGG AGC CTG CTG TGC TAT 3' |
| 131 | 1X23BR | 5' CCG CCG CCC CCG CCC GCT TGG TGG AGA CGG TGT AGT TGC 3' |
| 132 | 1X23CF | 5' TCC AAT CCC TTT CCC TTT GGC 3' |
| 133 | 1X23CR | 5' CAG CAG CCC ATG AAA CAG AAA G 3' |
| 134 | 1X24F | 5' TAT GCT TTC AGG CCC GTG GCA 3' |
| 135 | 1X24R | 5' AGA GCC CAT ACC CGG TCC AGT CC 3' |
| 136 | 1X25F | 5' GGA CTG GAC CGG GTA TGG GCT CT 3' |
| 137 | 1X25R | 5' CCC CCG CCC GCA CCC AGG CCC TCC TCG ACT C 3' |
| 138 | 1X26F | 5' CCC CCG CCG CTG GGT GGG CTC GGC TCT ATC 3' |
| 139 | 1X26R | 5' TGG TAG CGA TGC TCA CGT CAC TT 3' |
| 140 | 1X27F | 5' CAG GCC AAA GCT GAG ATG ACT TG 3' |
| 141 | 1X27R | 5' AGA GGC GCA GGA GGG AGG TC 3' |
| 142 | 1X28F | 5' CCC TCT GCC CCC GCA TTG 3' |
| 143 | 1X28R | 5' AAG CGC AAA AGG GCT GCG TCG 3' |
| 144 | 1X29F | 5' GGC CCT CCC TGC CTT CTA GGC G 3' |
| 145 | 1X29R | 5' CCG TGC TGT GTG GAG GAG AG 3' |
| 146 | 1X30F | 5' CCT CTT CCT GCC CAG CCC TTC 3' |
| 147 | 1X30R | 5' CTT CCC GAG CAG CCT TTG GTG 3' |
| 148 | 1X31F | 5' CTG AGC TGC CGC CCG CTG AC 3' |
| 149 | 1X31R | 5' AGG ACC CCA GCC CA GCC CA 3' |
| 150 | 1X32F | 5' CTT GGC GCA GCT TGG ACT 3' |
| 151 | 1X32R | 5' ACA CCC AGC AAG GAC ACG CA 3' |
| 152 | 1X33F | 5' TGT GAC ACA TCC CCT GGT AC 3' |
| 153 | 1X33R | 5' GCA AGG GTG AGC TTC AGA GC 3' |
| 154 | 1X34F | 5' GCC CCG CGC CCG TCC CGC CGC CCC CGC CCG ACC CTA TGC CTC CTG TAC CTC 3' |
| 155 | 1X34R | 5' CCC CTC CTC TGG CAA TCC 3' |

TABLE 3-continued

Examples of useful pkd-1 specific primers*

| SEQ ID NO. | Primer Name | Primer Sequence |
|---|---|---|
| 3 | 1X35F | 5' TGG CTG CAA CTG CCT CCT GG 3' |
| 4 | 1X35R | 5' AAG CAG AGA CAG ACC TGT GAG AG 3' |
| 5 | 1X36F | 5' GCC CCC GCC GCT CTC ACA GGT CTG TCT CTG CTT C 3' |
| 6 | 1X36R | 5' GGC CTG TAG CCT ACC CCT GG 3' |
| 7 | 1X37F | 5' GGA CCC CTC TGA AGC CAC C 3' |
| 8 | 1X37R | 5' GGG AGG TGG GAG ACA AGA GAC 3' |
| 9 | 1X38F | 5' AAA GCC CTG CTG TCA CTG TGG 3' |
| 10 | 1X38R | 5' AAC TAA AGC CCA GAA GAC AGA CC 3' |
| 11 | 1X39F | 5' AAC TGT CTG CCC CAG AAC ATC 3' |
| 12 | 1X39R | 5' CTA AAG GCT GCT CTC TCA ACA AG 3' |
| 13 | 1X40F | 5' ACT CCT GTT GGG TTT TGA TGA G 3' |
| 14 | 1X40R | 5' GAG AAC TAC TCC CTT GTC CTT GG 3' |
| 15 | 1X41F | 5' ACG CCA AGG ACA AGG GAG TAG TTC 3' |
| 16 | 1X41R | 5' TGG GCT CCT GGC TGG TGA CTG C 3' |
| 17 | 1X42F | 5' GCG GCC CGC CGC CCC CGC CGC TAC TGA CCC GCA CCC TCT G 3' |
| 18 | 1X42R | 5' GCT GCG AGG GGT GAG ACG 3' |
| 19 | 1X43F | 5' GCG GCC CGC CGC CCC CGC CGC GTC CCT CCC GCC CTC CTG ACC 3' |
| 20 | 1X43R | 5' GCC CCC GCC GCT GCG GAC GAG AAA TCT GTC TGC TTG 3' |
| 21 | 1X44F | 5' CAG GGC TGC AAG CAG ACA GA 3' |
| 22 | 1X44R | 5' CTG AGC TAA GAC GCC CTC CC 3' |
| 23 | 1X45F | 5' CTG TAC GCC CTC ACT GGT GTC 3' |
| 24 | 1X45R | 5' GGC ACA GGG GCT CAG TCA GTC 3' |
| 25 | 1X46AF | 5' GGA CTG ACT GAG CCC CTG TGC 3' |
| 26 | 1X46AR | 5' AGT CGG TCA AAC TGG GTG AG 3' |
| 27 | 1X46BF | 5' CAA GGT GTG AGC CTG AGC CC 3' |
| 28 | 1X46BR | 5' CGG TGT CCA CTC CGA CTC CAC 3' |

*All primer sequences are denoted in the 5'-3' direction. The first number in the name denotes the PKD gene number (<u>1</u>X15AF). The Letter 'X' signifies the word exon (1<u>X</u>15AF). The third number after the 'X' denotes the exon number (1X<u>15</u>AF). The character after the exon number represents the identity of the exon fragment (1X15<u>A</u>F). The last letter indicates the direction of the primer as either forward or reverse (1X15A<u>F</u>).

TABLE 4

Examples of useful pkd-2 specific primers*

| SEQ ID NO. | Primer Name | Primer Sequence |
|---|---|---|
| 29 | 2X1AF | 5' CCG CCC CCG CCG CGC GCC GGA CGC CAG TGA CC 3' |

TABLE 4-continued

Examples of useful pkd-2 specific primers*

| SEQ ID NO. | Primer Name | Primer Sequence |
|---|---|---|
| 156 | 2X1AR | 5' CCT GCC GGG AGC ACG ACG AG 3' |
| 30 | 2X1BF | 5' GCC CCC GCC GCC GCG GCC TCC CCT TCT CCT 3' |
| 157 | 2X1BR | 5' CTG GGC TGG GGC ACG GCG GG 3' |
| 158 | 2X1CF | 5' GGG GGC TAC CAC GGC GCG GGC 3' |
| 31 | 2X1CR | 5' CGG CCC GCC GCC CCC GCC CGC GGC CGT TCT GGT TCG TGC ATC TG 3' |
| 32 | 2X2F | 5' GCC CCC GCC GAA ATG ATA TCT TTT CCT TTC TTC A 3' |
| 33 | 2X2R | 5' CCC CCG CCC GAA CTT TCC CAT TAG TGC AAG 3' |
| 159 | 2X3F | 5' TTG GGG CGT TCA TTT GGA TC 3' |
| 34 | 2X3R | 5' CGC CGC CCC CGC CCG TGT GAT AGA GAG TAC TTT CA 3' |
| 35 | 2X4F | 5' CCG CCG CCC CCG CCG CTT TTT CAA AGA TGT TTC CTT TGC 3' |
| 36 | 2X4R | 5' TAT CAC CGA GTG CCA ATG AG 3' |
| 37 | 2X5F | 5' CCG CCG CCC CCG CCG GCC TCA AGT GTT CCA CTG AT 3' |
| 160 | 2X5R | 5' ACC ACA CAG AAA TAG GAG GG 3' |
| 161 | 2X6F | 5' TTG TTA TTG TTT TAA TTG TTC TTA 3' |
| 38 | 2X6R | 5' CCC CCG CCC GTT GTA GAA TAG AAT AGG AAA TTT GG 3' |
| 39 | 2X7F | 5' GCC CCC GCC GTT GGT GAA GAA AAA TAT ACT AGT CA 3' |
| 40 | 2X7R | 5' CGC CGC CCC CGC CCG TGG AAC TCA TTT TTT TTA AAG A 3' |
| 41 | 2X8F | 5' GCG GGG GCG GCG GGC CGT TTT ATT ATA CAC AGT CAC ACC 3' |
| 162 | 2X8R | 5' CTA CTC TGA CTA AAT TTT TCT TCT T 3' |
| 163 | 2X9F | 5' TTT GGT TTT GTA TTG TGG TG 3' |
| 164 | 2X9R | 5' AAG GAT TTA CGA AGT TTA AAT TG 3' |
| 42 | 2X10F | 5' GCC CCC GCC GCT TCC TTT AAT TTT TGC CCT 3' |
| 43 | 2X10R | 5' CGC CGC CCC CGC CCG GAA ACA ATG CTC ATT TTA TGT CAG 3' |
| 44 | 2X11F | 5' CCG CCG CCC CCG CCG AAA CCA AGT CTT TTA TTT TTT CTC 3' |
| 165 | 2X11R | 5' AGA ACC TCA GGA AGC ATG ATT 3' |
| 45 | 2X12F | 5' CCG CCG CCC CCG CCG GAT GAA TGT TAT CTG TAT CCT CTC 3' |
| 166 | 2X12R | 5' TAG GTA CCA AAT CAA ATC CG 3' |
| 167 | 2X13F | 5' GTC TCA GTG TTC TGC TCC TC 3' |
| 46 | 2X13R | 5' CGC CGC CCC CGC CCG GCA AAT TCT GCC AAT TCC TTT A 3' |
| 47 | 2X14F | 5' GCC CCC GCC GTT TGT CCC TCT GTA CTG TGT |

TABLE 4-continued

Examples of useful pkd-2 specific primers*

| SEQ ID NO. | Primer Name | Primer Sequence |
|---|---|---|
| | | 3' |
| 168 | 2X14R | 5' AAA TAC AAC TGT CAG CAA CAT A 3' |
| 48 | 2X15F | 5' CCG CCC CCG CCG TGA CCC CCA ACA CCA GTT TC 3' |
| 49 | 2X15R | 5' CGG CCC GCC GCC CCC GCC CGG GAC AGC CAC TTC CTC ACT T 3' |

*All primer sequences are denoted in the 5'-3' direction. The first number in the name denotes the PKD gene number (<u>2</u>X15R). The Letter 'X' signifies the word exon (2<u>X</u>15R). The third number after the 'X' denotes the exon number (2X<u>15</u>R). The last letter indicates the direction of the primer as either forward or reverse (2X15<u>R</u>).

B. Primer Combinations Useful for PKD-specific Amplification

The specifically amplified product can be generated by using one or more PKD-specific primers. Preferably, both primers used to generate one amplified product are PKD-specific primers. However, one PKD-specific primer can be used in combination with another non PKD-specific primer which is not complementary to a unique site of a PKD gene. The non PKD-specific primer is preferably designed according to the same criteria described above herein for the PKD-specific primers and is preferably to be completely complementary to a sequence other then a unique sequence in a PKD gene. A non PKD-specific primer may also be used as a control primer included in the amplification reaction to generate a control product.

Optimal results may be obtained by using one forward and one reverse primer listed in Table 4 and Table 5, although other combinations may also be used. In a preferred embodiment, a primer pair is selected so that the length of an amplified product is 150–600 bps. In the most preferred embodiment, a primer pair is selected so that the amplified fragment length for DHPLC mutation detection analysis is 150–400 bp.

C. Primer Synthesis

Methods for synthesizing primers are available in the art. The oligonucleotide primers of this invention may be prepared using any conventional DNA synthesis method, such as, phosphotriester methods such as described by Narang et al. (1979, Meth. Enzymol., 68:90) or Itakura (U.S. Pat. No. 4,356,270), or and phosphodiester methods such as described by Brown et al. (1979, Meth. Enzymol., 68:109), or automated embodiments thereof, as described by Mullis et al. (U.S. Pat. No. 4,683,202). Also see particularly Sambrook et al.(1989), Molecular Cloning: A Laboratory Manual (2d ed.; Cold Spring Harbor Laboratory: Plainview, N.Y.), herein incorporated by reference.

V. Preparing Template for Amplification Reaction

Any sample comprising a nucleic acid comprising the entire or a portion of SEQ ID NO. 1 or 2 or their variants (e.g., polymorphism forms or mutant forms) may be used to as template for amplification reaction of the present invention. Useful templates, according to the invention, include, but are not limited to, genomic DNA preparation, total RNA preparation, crude cell lysate and tissue sample.

It's preferred to use genomic DNA as template for PKD-specific amplification of the subject invention. While it is envisioned that crude cell lysate or tissue sample may be used, one skilled in the art will recognize that any non-DNA material present in the sample may interfere with the polymerase reaction or subsequent analysis.

Genomic DNA can be isolated from tissue samples or cells. Preferably, the genomic DNA used as template for the invention is isolated under conditions which preclude degradation and contamination. Tissue samples or cells may be digested with a protease so that there is likely to be little or no DNAase activity. The digest is extracted with a DNA solvent. The extracted genomic DNA may be purified by, for example, dialysis or chromatography. Suitable genomic DNA isolation techniques are known in the art, for example, as described in *Current protocols in molecular biology*, Ausubel et al., John Weley & Sons, Inc., 1997.

Preferably, genomic DNA or cDNA is extracted from cell lysate of tissue samples taken from an individual and used as template for PKD amplification. Collecting a tissue sample also includes in vitro harvest of cultured human cells derived from an individual's tissue or any means of in vivo sampling directly from a subject, for example, by blood draw, spinal tap, tissue smear or tissue biopsy. Optionally, tissue samples are stored before analysis by well known storage means that will preserve a sample's nucleic acids in an analyzable condition, such as quick freezing, or a controlled freezing regime, in the presence of a cryoprotectant, for example, dimethyl sulfoxide (DMSO), glycerol, or propanediol-sucrose. Tissue samples can also be pooled before or after storage for purposes of amplifying them for analysis. In some embodiments, the sample contains DNA, tissue or cells from two or more different individuals.

Any human tissue containing nucleic acids can be sampled and collected for the purpose of practicing the methods of the present invention. A most preferred and convenient tissue for collecting is blood. No patient preparation is necessary prior to blood draw. No medications are known to interfere with sample collection or testing. Usual aseptic techniques and avoidance of contamination are necessary.

Preferably, DNAs are extracted from blood on the day it was drawn. Blood is preferred to stored at room temperature (72° F. or 25° C.) before use. However, whole blood may be stored for short periods at 4° C. but room temperature is recommended. Whole blood specimens may be stable for 48 hrs. After this time hemolysis may compromise DNA recovery and integrity. The optimal amount of blood for DNA extraction for the PCR assay is preferred to be more than 5 ml, e.g., more than 10.0 ml.

VI. PCR Amplification Using PKD-specific Primers

The subject invention provides a method of mutation analysis of a target nucleic acid comprising SEQ ID NO. 1 or 2 or their variants by amplifying the DNA from a sample comprising the target nucleic acid in a polymerase chain reaction and detecting in a specifically amplified product the presence or absence of a mutation in the target nucleic acid.

Amplification may be carried out by means well known in the art, for example, polymerase chain reaction (PCR), transcription based amplification (reverse transcription), strand displacement amplification (see *Current Protocol in Molecular Biology*). Preferably, the amplification is carried out by PCR, such as described by Mullis (U.S. Pat. No. 4,683,202), the contents of which are incorporated by reference herein.

PCR makes possible the amplification (replication) of minute samples of DNA or other nucleic acids of any base pair length (size) by taking advantage of highly selective enzymes called DNA polymerases, to extend small DNA strands called "primers" along a "template". The minute DNA sample serves as the template. PCR reproduces the complementary sequence of deoxynucleotide triphosphate (dNTP) bases present in the template or any chosen portion thereof. The PCR is commonly used in conjunction with diagnostic techniques where, for example, a DNA sample having a concentration below the limit of detection is amplified by the PCR process, and the larger amount so obtained is subsequently analyzed.

Apparatus for performing PCR amplifications, e.g. Air Thermo Cycler (Idaho Technologies) and reagents are commercially available from numerous sources, e.g. Perkin-Elmer Catalog "PCR Systems, Reagents and Consumables" (Perkin-Elmer Applied Biosystems, Foster City, Calif.).

PCR is typically run in a buffer at pH 5–8. The buffer contains a double stranded DNA sample to be amplified, a forward primer, a reverse primer, magnesium (e.g., as $MgCl_2$), and the four deoxynucleotide triphosphates (dATP, dTTP, dCTP, and dGTP) generally referred to as "dNTPs", the building blocks of DNA. The reaction mixture is heated to a temperature (e.g., >90° C.) sufficient to denature the DNA sample, thereby separating its two complimentary nucleic acid strands. Alternatively, the DNA may be denatured enzymatically at ambient temperature using a helicase enzyme. If denaturing is effected by heat and a thermostable DNA polymerase is used, the DNA polymerase is added before the reaction is started. Other denaturing conditions are well known to those skilled in the art and are described in U.S. Pat. No. 5,698,400. DNA polymerases are commercially available from a variety of sources, e.g. Perkin-Elmer Applied Biosystems, (Foster City, Calif.) and Stratagene (La Jolla, Calif.).

The primer sequence is designed to be complimentary to an identified portion of the denatured DNA strands to be replicated by PCR. Upon cooling the reaction to an appropriate annealing temperature, each of the primers anneals to its complimentary base sequence in each strand of the denatured DNA sample to be replicated. Heated to about 70° C. in the presence of the DNA polymerase, the 4 dNTPs and $Mg^{2+}$, replication extends the primers from their 3'-ends by adding complimentary dNTPs along the length of the strand. dNTPs are commercially available from a variety of sources, e.g. Pharmacia (Piscataway, N.J.). By repeating this process numerous times, a geometric increase in the number of desired DNA strands is achieved in the initial stages of the process or as long as a sufficient excess of reagents are present in the reaction medium. Thus, the amount of the original DNA sample is amplified.

The amount of polymerase must be sufficient to promote DNA synthesis throughout the predetermined number of amplification cycles. Guidelines as to the actual amount of polymerase are generally provided by the supplier of the PCR reagents and are otherwise readily determinable by a person of ordinary skill in the art. Preferably, a DNA polymerase with proof-reading activity is used.

The amount of each primer must be in substantial excess of the amount of target DNA to be amplified. The amount of primer needed for the reaction mixture can be estimated by one skilled in the art in terms of the ultimate number of amplified fragments desired at the conclusion of the reaction.

To prevent false positive results, one skilled in the art will recognize that the assays should include negative controls as is conventional in the art. For instance, suitable negative controls may contain no primer or no DNA (i.e. "water controls"). To prevent false negative results, positive controls are provided by the control primers (see below).

A. Optimization of PCR Conditions

Successful specific amplification, e.g., an amplification which produces maximal amount of specifically amplified products and minimal amount of non-specifically amplified products, according to the invention, depends in great measure on the specific annealing of the PKD-specific primers to the corresponding matched template. If the primer anneals non-specifically to many different sequences in the reaction mixture, the amplification process will not be specific. Although it is unlikely in most of the embodiments to avoid any non-specific annealing or non-specific amplification, it is desirable to optimize the PCR amplification reaction condition so to reduce the non-specific amplification while increase the specific amplification.

In addition, PCR induced mutations, wherein a non-complimentary base is added to a template, are often formed during sample amplification. Such PCR induced mutations make mutation detection results ambiguous, since it may not be clear if a detected mutation was present in the sample or was produced during the PCR process. Applicants have recognized the importance of optimizing PCR sample amplification in order to minimize the formation of PCR induced mutations and ensure an accurate and unambiguous analysis of putative mutation containing samples.

B. Controlling the Specificity of PKD-specific Annealing of PKD-specific Primers.

The degree of fidelity of replication of DNA fragments by PCR depends on many factors which have long been recognized in the art. Some of these factors are interrelated in the sense that a change in the PCR product profile caused by an increase or decrease in the quantity or concentration of one factor can be offset, or even reversed by a change in a different factor. For example, an increase in the enzyme concentration may reduce the fidelity of replication, while a decrease in the reaction temperature may increase the replication fidelity. An increase in magnesium ion concentration or dNTP concentration may result in an increased rate of reaction which may have the effect of reducing PCR fidelity. A detailed discussion of the factors contributing to PCR fidelity is presented by Eckert et al., (in *PCR: A Practical Approach,* 1991, McPherson, Quirke, and Taylor eds., IRL Press, Oxford, Vol. 1, pp. 225–244); and Andre, et. al., (1977, *GENOME RESEARCH,* Cold Spring Harbor Laboratory Press, pp. 843–852). These references and the references cited therein are incorporated in their entirety herein. Thus, availability of a product profile of the PCR process, makes possible the optimization of PCR conditions to improve results in a highly efficient manner.

In PCR amplification, the specificity of the annealing is most important in the first few cycles. The remaining cycles only serve to expend the pool of template which is amplified in the first few cycles. The specificity of primer annealing to template is controlled by the ionic strength (primarily the K$^+$ concentration) of the buffer, the Mg$^{2+}$ concentration (which is bound to dNTPs and therefore affected by the amount of dNTPs), and the annealing temperature of each cycle of the amplification. In preferred embodiments, the dNTP concentrations are 50 nM, preferably 100 nM, more preferably 200 nM.

Conditions for specific annealing of primers to particular template targets must be determined empirically, usually by varying the annealing temperature in several degree increments and comparing the specificity and sensitivity of the amplification process by agarose gel electrophoresis (See *Current Protocol in Molecular Biology,* supra).

Because a unique region to which a PKD-specific primer complement to may differ from a homologue sequence only by a few nucleotides, sometimes by only one nucleotide, the specificity of the amplification reaction needs to be tested for each PKD-specific primer used in the reaction.

The formula for calculating primer annealing temperature provided above is only a rough guide, successive trials at different annealing temperatures is the usual way to optimize this important parameter in the PKD-specific amplification reaction. Apparatus are available for simultaneous testing of different annealing temperatures of particular primer-template pairs, which enables the optimal annealing temperature to be determined rapidly and reliably (e.g., Robocycler Gradient Temperature Cycler, Cat #400864, Stratagene; Eppendorf mastercycler gradient, Cat #5331 000.045, Brinkmann Instruments, Inc. Westbury, N.Y.).

In some embodiments, the target sequences are amplified at an annealing and extending temperature that is between 1° C. and 10° C. higher than the Tm for the primer pair. Although amplification at this temperature is inefficient, any primer extension that occurs is target specific. Consequently, during the high temperature cycle(s), the sample is enriched for the particular target sequence and any number of cycles, i.e., 1–15 enhances product specificity. The annealing temperature may be then decreased to increase amplification efficiency and provide a detectable amount of PCR product. Or a nested amplification reaction may be performed using the amplified product from the first PCR reaction as template (see below).

Alternatively, one can simultaneously run a set of reactions at a constant temperature but vary the concentration of KCl or MgCl$_2$ or add variable amounts of a denaturant such as formamide (e.g., 0, 2, 4, 6%), DMSO (1–10%) to define the optimum conditions for generating a high yield of specific product with a minimum of nonspecific products.

In one embodiment, a pair of primers comprising at least one selected from the group consisting of SEQ ID NOs. 3–49 is used in the amplification reaction mixture. The orientation of the two primers is opposite to allow the generation of one or more specifically amplified product.

In some embodiments of the invention, when primers used for PKD-specific amplification are selected from SEQ ID NOs. 3–49, AmpliTaq Gold DNA polymerase with GeneAmp PCR buffer II and MgCl$_2$ solution and rTth DNA polymerase XL & XL buffer II pack from Perkin Elmer, and TaqPlus Precision PCR system from Stratagene were used. PFUTurbo™ is another high fidelity DNA polymerase having greater proof reading provided by Stratagene.

In other embodiments, an annealing temperature of above 65° C. (e.g., 68–72° C.) is used for PKD-specific amplification using primers selected from SEQ ID NOs. 3–49.

In general, it is preferred but not essential that the DNA polymerase is added to the amplification reaction mixture after both the primer and template are added. Alternatively, for example, the enzyme and primer are added last or the reaction buffer or template plus buffer are added last. It is generally desirable that at least one component that is essential for polymerization not be present until such time as the primer and template are both present, and the enzyme can bind to and extend the desired primer/template substrate. This method, termed "hot start," minimizes the formation of "primer-dimer" and improves specificity of the amplification.

The degree of specificity of DNA polymerases varies with the reaction conditions employed as well as with the type of enzyme used. No enzyme affords completely error free extension of a primer. Therefore, a non-complimentary base may be introduced from time to time. Such enzyme related errors produce double stranded DNA products which are not exact copies of the original DNA sample, but contain PCR induced mutations. Other PCR process features, such as reaction temperature, primer annealing temperature, enzyme concentration, dNTP concentration, Mg$^{2+}$ concentration, and combinations thereof, all have the potential to contribute to the degradation of the accuracy or fidelity of DNA replication by the PCR process, as described above herein.

C. Sensitivity of PKD-specific Amplification

The sensitivity of the PKD-specific amplification of the subject invention depends on the template and primers used in an amplification reaction, as well as ionic strength and annealing temperature of each cycle of the amplification.

When genomic DNA is used as template, as few as one or two copies of the template (about 3–5 pg) can be used for successful PCR amplification if the reaction condition has been optimized. However, it's known in the art that a higher template concentration may increase the specificity and efficiency of the amplification.

Shorter fragments are amplified more efficiently than longer fragments. Preferably, primers which generate an amplified product of less than 1 kb, more preferably less than 600 bp, or less than 450 bp in length are used to increase sensitivity of the amplification assay.

Preferably, the sensitivity of the amplification assay is less than 100 ng genomic DNA template. More preferably, the sensitivity of the assay is less than 10 ng genomic DNA template. More preferably, the sensitivity of the assay is less than 1 ng genomic DNA template. More preferably, the sensitivity of the assay is less than 0.1 ng genomic DNA template. Even more preferably, the sensitivity of the assay is less than 0.01 ng genomic DNA template.

D. Nested Amplification

In some embodiments of the invention, a nested amplification is performed using amplified products in a preceding amplification reaction as templates. Preferably, the nested amplification reaction is a nested PCR using PCR amplified products from a preceding PCR reaction as templates. In addition to optimizing the annealing temperature of the primers, "nested" amplification can be used to increase the specificity and sensitivity of the PKD-specific amplification assay.

For example, a method comprising a nested PCR involves two sequential PCR reactions. After multiple cycles of PCR (e.g., 10 to 40, or 10 to 30 or 10 to 20 cycles) with the first pair of primers comprising at least one PKD-specific primer (e.g., a PKD-specific primer and a control primer or two PKD-specific primers), a small amount aliquot of the first reaction (e.g., 1 µl of a 50 µl reaction) serves as the template for a second multiple cycles of PCR reaction (e.g., 10 to 40, or 10 to 30 or 10 to 20 cycles) with a new set of primers comprising at least one PKD-specific primer (e.g., a PKD-specific primer and a control primer or two PKD-specific primers) that anneal to sequences internal to, or nested between, the first pair.

Methods for designing nested primers and for performing nested PCR are known in the art (see *Current Protocol in Molecular Biology*, supra). The general criteria for selecting primers as described above also applies to the design of nested primers. Both nested primers need to anneal to sequences internal to (e.g., within) the first pair of primers and at least one of the nested primers, however, according to the subject invention, needs to be PKD-specific.

Using the nested PCR procedure, the template that is successfully amplified is selected twice for PKD-specificity. The use of nested PCR can also greatly enhance the yield of the species-specific product, therefore the sensitivity of the assay, when a single primer pair fails by itself.

A sample comprising genomic DNA or cDNA may be used to provide DNA template for the amplification reaction. Preferably, genomic DNA is used as template. When a sample comprising genomic DNA is used in the reaction mixture, a pair of primers comprising at least one selected from the group consisting of SEQ ID NOs. 3–49 generate at least two specifically amplified product, one from each PKD allele in the genomic DNA sample.

E. Amplification Controls

Control primers can be used to serve as positive control for the PKD-specific amplification. The control primers may be added to the same reaction mixture for PKD-specific amplification, or it may be added to a control reaction which is run in the same PCR apparatus under the same parameters. A control primer may comprise a sequence complementary to any identical sequence between a PKD gene and a PKD homologue. Preferably, the control primers generate a single amplified product whose size is distinguishable from that amplified by a pair of primers comprising at least one PKD-specific primers. The size of the amplified product by the control primers may be greater or smaller than the size of the amplified products generated by the pair of primers comprising at least one PKD-specific primers. Preferably, the control primers are chosen to generate a control product which has at least 100 bp, more preferably at least 500 bp, more preferably at least 1000 bp difference in size compared to the amplified product generated in the same amplification reaction by the pair of primers comprising at least one PKD-specific primers.

A control amplification is especially important when analyzing a PKD allele with deletions at the location where a PKD-specific primer anneals. The lack of a specific amplification in the presence of an amplified control product may indicate the presence of the deletion at a specific location of a PKD gene. In some embodiments, more than one pair of control primers is used in the reaction mixture.

See Example 2 for various controls that might be used for the genetic testing method of the invention.

Amplified products may be purified to get rid of free primers used in the amplification by methods known in the art (e.g., Current Protocols in Molecular Biology, supra). In a preferred embodiment, the PCR products are purified using the Quickstep™ 96 well PCR Purification Kit from Edge Biosystems.

VII. Detecting the Presence of PCR Amplified Products

The cycle of DNA denaturation, primer annealing and synthesis of the DNA segment defined by the 5' ends of the primers is repeated as many times as is necessary to amplify the template target until a sufficient amount of either a species-specific or a universal product is available for detection. At the conclusion of the amplification reaction, the presence of amplified products may be detected using techniques conventional in the art.

The primers may be labeled for facilitating the detection. The primers can be labeled with a directly detectable tag, for example a radioactive label such as $^{32}P$, $^{35}S$, $^{14}C$ or $^{125}I$, a fluorescent compound such as fluorescein or rhodamine derivatives, an enzyme such as a peroxidase or alkaline phosphatase, or avidin or biotin. The PKD-specific primers used to generate the PKD-specific product and the control primers used only to generate the control product may have the same or different labels.

In a preferred embodiment, the amplification products are conveniently analyzed by gel electrophoresis.

Electrophoresis is conducted under conditions which effect a desired degree of resolution of fragments. A degree of resolution that separates fragments that differ in size by as little as about 500 bp is usually sufficient. Preferably, the resolution is at about 100 bp. More preferably, the resolution is at about 10 bp. Size markers may also be run on the gel to permit estimation of the size of fragments. Preliminary analysis of the size of specifically amplified products may indicate insertions or deletions within a PKD gene, and the information obtained can be interpreted together with results obtained from subsequent DHPLC and sequence analysis.

The amplification product pattern may be visualized. Where an amplification primer has been labeled, this label may be revealed. A substrate carrying the separated labeled DNA fragments is contacted with a reagent which detects the presence of the label. For example, an amplified product generated from a radioactively labeled primer may be detected by radioautography. Where the amplification primers are not labeled, the substrate bearing the PCR product may be contacted with ethidium bromide and the DNA fragments visualized under ultraviolet light.

VIII. Separating PCR Amplified Products

Under the most stringent condition which only allows the annealing of completely complementary sequences but not sequences comprising one or more non-complementary nucleotides, a PKD-specific primer will only anneal to an authentic PKD gene template, but not a PKD homologue. Therefore, under the most stringent condition, a PKD-specific primer, in combination with a primer with opposite orientation, being PKD-specific or not, will only produce amplified product from an authentic PKD template, but not from a PKD homologue. However, during a typical PCR amplification reaction, a PKD-specific may anneal to a template comprising an authentic PKD gene and a PKD homologue, especially due to the temperature cycling required by a PCR reaction. Therefore, both specifically amplified products and non-specifically amplified products may be produced, although the amount of non-specifically amplified products may be reduced by the use of at least one PKD-specific primer.

A. Formation of Homoduplex and Heteroduplex

In one embodiment of the invention, a mixture of homoduplexes and heteroduplexes is formed prior to the DHPLC analysis. A standard nucleic acid homoduplex (e.g., amplified product from a normal PKD allele) may be added to the sample and the mixture is subjected to denaturation, e.g. by heating the mixture to about 90° C. or about 95° C. The denatured single stranded nucleic acids formed during the denaturation process are then annealed by slowly cooling the mixture to ambient temperature. A new mixture of homoduplexes and heteroduplexes is formed if the sample contains a mutation. If the sample does not contain a mutation, only a homoduplex of the standard nucleic acid will be formed. In the preferred embodiment, the standard nucleic acid is the "normal" nucleic acid.

In most cases, a PKD patient individual is heterozygous at the loci comprising a PKD gene. That is, the carrier has only one PKD allele and a mutant form and has the other allele as a normal form (e.g., wild type). Since most of the PKD mutations result in a dominant phenotype, one mutant allele is sufficient to predispose a risk for ADPKD development. Another heterozygous situation is when both alleles are mutated but each carries one or more different mutations. For a heterozygous PKD patient, a PCR amplification using a primer pair comprising at least one PKD-specific primer, including a nested PCR amplification, would result in at least two specifically amplified PKD products, one from each allele. The two specifically amplified PKD products may or may not be of the same length (e.g., different length if the mutation on one allele comprises a deletion or an insertion) and would differ in at least one nucleotide from each other.

The amplified products may be denatured and re-annealed with each other to form duplexes. When a specifically amplified product from a normal allele or a specifically amplified product from a mutant allele anneals to another specifically amplified product from the same allele, they will form homoduplex. However, if a specifically amplified product from a normal allele anneals to a specifically amplified product from a mutant allele, they form a heteroduplex.

In rare cases, a mutation is in homozygous form, that is, both alleles in an individual (e.g., a PKD patient) comprise the same mutations. If a sample is taken from a homozygous PKD patient, the PCR amplification will not generate specifically amplified products which can form heteroduplex upon denaturing and re-annealing. In some embodiments of the invention, a sample comprising a normal (e.g., a wide type) PKD gene is added to the PCR reaction mixture so that amplification using a primer pair comprising at least one PKD-specific primer will produce specifically amplified products from the normal PKD gene, therefore ensuring the formation of a heteroduplex during the denaturation and re-annealing process following PCR amplification.

Homoduplexes formed in the denaturation and re-annealing process may also include those formed by non-specifically amplified products. If in very rare cases, a sequence in a template allele (e.g., a PKD homologue sequence) which give rise to non-specifically amplified products also comprises one or more mutation, a heteroduplex may also form. The heteroduplex formed between non-specifically amplified products will also be subjected to further separating the identification process.

B. Separating and Identifying Heteroduplex

The presence of a heteroduplex formed by PKD-specifically amplified products indicates the presence of a mutation in a PKD gene. By separating for heteroduplexes, one can identify whether a mutant allele present in the sample, e.g., taken from an individual. This separating process gets rid of most of the non-specifically amplified products and specifically amplified products from normal alleles, therefore improves the efficiency and specificity of identifying a mutant allele and a PKD patient.

It is well known in the DNA art that a heteroduplex strand will denature selectively at the site of base pair mismatch, creating a "bubble", at a lower temperature than is necessary to denature the remainder of the heteroduplex strand, i.e., those portions of the heteroduplex strand which contain complimentary base pairs. This phenomenon, generally referred to as partial denaturation, occurs because the hydrogen bonds between mismatched bases are weaker than the hydrogen bonds between complimentary bases. Therefore, less energy is required to denature the heteroduplex at the mutation site, hence the lower temperature required to partially denature the heteroduplex at the site of base pair mismatch than in the remainder of the strand.

Since at least one base pair in a heteroduplex is not complimentary, it takes less energy to separate the bases at that site compared to its fully complimentary base pair analog in a homoduplex. This results in the lower melting temperature of a heteroduplex compared to a homoduplex. The local denaturation creates, what is generally called, a "bubble" at the site of base pair mismatch. The bubble distorts the structure of a DNA fragment compared to a fully complimentary homoduplex of the same base pair length. This structural distortion under partially denaturing conditions has serves as the basis for DHPLC to separate heteroduplexes and homoduplexes.

A separation process called "Denaturing HPLC" (DHPLC) has been used to detect mutations by separating a heteroduplex (resulting from the presence of a mutation) and a homoduplex having the same bp length. DHPLC has been applied to mutation detection (e.g., see Underhill, et al., 1997, Genome Research 7:996; Liu, et al., 1998, Nucleic Acid Res., 26;1396). This separation is based on the fact that a heteroduplex has a lower melting temperature (Tm) than a homoduplex. When DHPLC is carried out at a partially denaturing temperature, i.e., a temperature sufficient to denature a heteroduplex at the site of base pair mismatch, homoduplexes can be separated from heteroduplexes having the same base pair length (Hayward-Lester, et al., 1995, Genome Research, 5:494; Underhill, et al., 1996, Proc. Natl. Acad. Sci. USA 93:193; Doris, et al., 1997, DHPLC Workshop, Stanford University). These references and the references contained therein are incorporated herein in their entireties. Thus, the use of DHPLC was applied to mutation detection (Underhill, et al., 1997, Genome Research 7:996; Liu, et al., 1998, Nucleic Acid Res., 26:1396). DHPLC can separate heteroduplexes that differ by as little as one base pair under certain conditions. The references cited above and the references contained therein are incorporated in their entireties herein.

The change in the structure of DNA from an orderly helix to a disordered, unstacked structure without base pairs is called the helix-random chain transition, or melting. Statistical-mechanical analysis of equilibria representing this change as a function of temperature for double-stranded molecules of natural sequence has been presented by Wartell and Montroll (1972, Adv. Chem. Phys. 22:129). The theory assumes that each base pair can exist in only two possible states-either stacked, helical, and hydrogen bonded, or disordered. It permits calculation of the probability that each individual base pair is either helical or melted at any temperature, given only the base sequence and a very small number of empirically calibrated parameters. The statistical-mechanical theories take into account the differing intrinsic stabilities of each base pair or cluster of neighboring base pairs, the influence of adjacent helical structure on the probability that a neighboring base pair is helical or melted (the coopertivity), and the restrictions on the conformational liberty of a disordered region if it is bounded at both ends by helical regions.

Iteration of the probability calculation at a closely spaced series of temperature steps and interpolation permit determination of the midpoint temperature at which each base pair is at 50/50 equilibrium between the helical and melted states. The MELT program provides the midpoint temperature and some other functions. A plot of midpoint temperature as a function of position along the molecule is called a melting map. It clearly shows that the melting of nearby base pairs is closely coupled over substantial lengths of the molecule despite their individual differences in stability. The existence of fairly long regions, 30–300 bp, termed domains, in which all bases melt at very nearly the same temperature, is typical. The melting map directly delineates the lowest melting domains in the molecules.

At a partially denaturing temperature, a heteroduplex having a base pair mismatch within a sample sequence will denature at the site of the mismatch, while the rest of the sample sequence will remain intact. The partially denatured heteroduplex can be separated and detected using DHPLC.

When HPLC is used under partially denaturing conditions (e.g., DHPLC) to separate a mixture of homoduplexes and heteroduplexes, the heteroduplexes usually elute ahead of the homoduplexes.

In particular embodiment of the invention, a heteroduplex is separated and identified from a homoduplex by DHPLC, and the presence of heteroduplex indicates the presence of at least one mutation in the PKD gene, e.g., a substitution of one or more nucleotides (or insertion or deletion of one or more nucleotides) present in the mutant allele.

In another particular embodiment, DHPLC gradient is determined by Wavemaker™ 4.0 software from Transgenomic, Inc. (San Jose, Calif.).

Separating applications require that the mutation can be detected regardless of where the mutation might be located on the fragment. In this situation, the mutation might be located in the middle of the fragment or in a higher melting domain, both cases where it is more difficult to detect. It is preferred than the range of melting variation of the fragment is no greater than 10° C. and most preferred is the range of variation is no greater than 5° C.

In some mutation analyses, only two peaks or a partially resolved peak(s) are observed in DHPLC analysis. The two homoduplex peaks may appear as one peak or a partially resolved peak and the two heteroduplex peaks may appear as one peak or a partially resolved peak. In some cases, only a broadening of the initial peak is observed under partially denaturing conditions.

If a sample contained homozygous DNA fragments of the same length, then hybridization and analysis by DHPLC would only produce a single peak at any temperature since no heteroduplexes could be formed. In the operation of the present method, the determination of a mutation can be made by hybridizing the homozygous sample with the known wild type fragment and performing a DHPLC analysis at a partially denaturing temperature. If the sample contained only normal allele then a single peak would be seen in the DHPLC analysis since no heteroduplexes could be formed. If the sample contained heterozygous mutant alleles, then analysis by DHPLC would show the separation of homoduplexes and heteroduplexes.

The temperature at which 50% of a constant melting domain is denatured may also be determined experimentally by plotting the UV (UV) absorbance of a DNA sample against temperature. The absorbance increases with temperature and the resulting plot is called a melting profile (Breslauer et al., 1986, Proc. Natl. Acad. Sci. USA 83:3746; Breslauer, 1987, *Calculating Thermodynamic Data for Transitions of any Molecularity*, p. 221, Marky et al. eds., J. Wiley and Sons). The midpoint of the absorbance axis on the melting profile represents the melting temperature (Tm), i.e. the temperature at which 50% of the DNA strands in the duplex are denatured. In one embodiment of the present invention, this observed Tm is used as a starting temperature for performing DHPLC for mutation detection. The temperature may be then adjusted according to the patterns observed using different controls (see below). In one embodiment, a consistent Tm is used to analyze the same amplicons (i.e., produced by the same pair of primers) from different samples.

In another embodiment of the present invention, software such as MELT (Lerman, et al., 1987, Meth. Enzymol. 155:482) or WinMelt™, version 2.0, is used to obtain a calculated Tm which is used as a starting temperature for performing DHPLC for mutation detection. These software programs show that despite individual differences in base pair stability, the melting temperature of nearby base pairs is closely coupled, i.e., there is a cooperative effect. Thus, there are long regions of 30 to 300 base pairs, called "domains", in which the melting temperature is fairly constant. In a similar manner, the software MELTSCAN (Brossette, et al., 1994, Nucleic Acid Res. 22:4321) calculates melting domains in a DNA fragment and their corresponding melting temperatures. The concept of a constant temperature melting domain is important since it makes possible the detection of a mutation in any portion of the domain at a single hetero-mutant site selective temperature.

Another particular method for separating and identifying heteroduplex is Matched Ion Nucleic acid Chromatography (MIPC). MIPC was introduced to effectively separate mixtures of double stranded nucleic acids, in general and DNA, in particular, wherein the separations are based on base pair length (U.S. Pat. Nos. 5,585,236 and 6,287,822; Huber et al., 1993, Chromatographia 37:653; Huber et al., 1993, Anal. Biochem. 212:351). These references and the references contained therein are incorporated herein in their entireties. MIPC separations are complete in less than 10 minutes, and frequently in less than 5 minutes. MIPC systems (WAVE™ DNA Fragment Analysis System, Transgenomic, Inc. San Jose, Calif.) are equipped with computer controlled ovens which enclose the columns and column inlet areas.

Although DHPLC and MICP are the described methods for separating and identifying heteroduplex, it is understood that other methods known in the art may also be used for identifying heteroduplex. For example, heteroduplex analysis on high resolution gel matrices are also able to detect even single nucleotide polymorphisms. (Hauser et al., 1998, Plant. J. 16:117–25). The PCR/OLA procedure can be used for analyzing amplification products to detect SNPs in the 3' end of the human PKD gene (Glick and Pasternak, 1994, *Molecular Biotechnology: Principles and Applications of Recombinant DNA*, ASM Press, Washington, D.C., pp. 197–200). Conformation-sensitive gel electrophoresis of amplification products may also be employed as a means of analysis by the skilled artisan in practicing the methods of the present invention. (Markoff et al., 1998, Eur. J. Genet. 6:145–50). This can also be achieved by techniques such as PCR-restriction fragment-SSCP, which can detect single base substitutions, deletions or insertions (Tawata et al., 1996, Genet. Anal. 12(3–4):125–27; Lee et al., 1992, Anal. Biochem. 205:289–93). Electrophoresis for analyzing amplification products is done rapidly and with high sensitivity by using any of various methods of conventional slab or capillary electrophoresis, with which the practitioner can optionally choose to employ any facilitating means of nucleic acid fragment detection, including, but not limited to, radionuclides, UV-absorbance or laser-induced fluorescence (Keparnik et al., 1998, Electrophoresis 19:249–55; Inoue et al. 1998, J. Chromatogr. A. 802:179–84; Dovichi, 1997, 18:2393–99; Arakawa et al., 1997, J. Pharm. Biomed. Anal. 15:1537–44; Baba, 1996, J. Chromatgr B. Biomed. Appl. 687:271–302; Chan et al., 1997, J. Chromatogr B.

Biomed. Sci. Appl. 695:13–15). Any of diverse fluorescent dyes can optionally be used to label primers of the present invention or amplification products for ease of analysis, including but not limited to, SYBR Green I, Y1O-PRO-1, thiazole orange, Hex (i.e., 6-carboxy-2',4',7',4,7-hexachlorofluoroscein), pico green, edans, fluorescein, FAM (i.e., 6-carboxyfluorescein), or TET (i.e., 4,7,2',7'-tetrachloro-6-carboxyfluoroscein) (e.g., Skeidsvoll and Ueland, 1995, Anal. Biochem. 231:359–65; Iwahana et al., 1996, Biotechniques 21:510–14, 516–19).

In using the invention in its preferred embodiment to effect a separation of homoduplexes and heteroduplexes for the purpose of mutation detection, a DNA sample is hybridized with a normal DNA fragment by denaturing and annealing the mixture as described herein above. The DNA sample can be hybridized with normal DNA directly. The DNA sample can also be amplified by PCR and then hybridized with the normal DNA. Alternatively, a normal fragment may be added to the sample prior to PCR amplification. The amplified mixture can then be hybridized following amplification. In each of these three hybridization scenarios, a mixture of homoduplexes and heteroduplexes is produced if a mutation is present in the sample. The sample, so prepared, is analyzed by DHPLC under partially denaturing conditions, preferably at 56 to 58° C., for the presence of a mutation using the method of the invention.

When the method of the invention is used for separating a large number of samples for the presence of a mutation, the throughput of samples may be increased significantly by speeding up the analysis for each sample using a steeper gradient for the fragment bracketing range.

In all embodiments and aspects of the invention, the nucleic acid fragments are detected as they are separated and eluted from the DHPLC column. Any detector capable of detecting nucleic acids can be used in the DHPLC mutation detection method. The preferred detector is an online UV detector. If the DNA fragments are tagged with fluorescent or radioactive tags, then a fluorescence detector or radioactivity detector can be employed, respectively. Following detection, the separated fragments are displayed on a video display separate or printed by a printer. The fragments so displayed appear either as peaks or as bands in a lane.

C. Quality Controls Helpful for Evaluating DHPLC for PKD-2 and PKD-1 Unique Region The chemical principles which permit DHPLC to distinguish between heteroduplex-homoduplex mixtures and homoduplexes alone also make the methodology quite sensitive to (1) buffer composition, (2) oven temperature at the time of analysis, (3) column condition, and (4) system condition at the time a sample is injected. Fluctuation in elution patterns is normal, and varies depending on the size and sequence of the amplicon, and the specific DHPLC conditions under which it is analyzed. On skilled in the art would have the knowledge in interpreting the elution patterns produced, for example, by following the protocol provided by the manufacture of the DHPLC equipment. However, limits on the extent of fluctuation are appropriate to help ensure that conditions are within a range that would be expected to effectively separate for DNA variants. The following quality control requirements are useful examples established for each analytical condition to ensure consistent assay performance.

1. No DNA Control

This control demonstrates that reagents and materials are free of non-specific signal that could interfere with patient analysis. In some embodiment, the control must show minimal signal (<10% of normal control peak height) in a no-DNA sample treated identically to a sample comprising a DNA, e.g., extracted from a tissue. Because all of the analytical system's hardware is re-used for each sample analysis, and because the DHPLC analysis is the separating component, up to 10% peak height of the normal control is permitted. Actual contamination with a different sequence might cause a false positive DHPLC pattern difference which would trigger reflexing to sequencing which would not be expected to detect a 10% contaminant. In the event that a sequence difference is detected, the fragment would be repeated from the point of PCR to confirm the result. Similarly contamination of an actual positive with 10% of a normal sequence would not be expected to significantly alter the pattern since 50% of the DNA present is already normal. Rare cases where a very subtle pattern change might be obscured by 10% extra normal DNA in the injection are accounted for in the sensitivity estimates of 78–96%. However, persistent no DNA signal each time the amplicon is analyzed indicates the need to alter analytical conditions to minimize or eliminate a systematic and persistent no DNA signal.

2. Normal Control

In one embodiment, the normal control pattern must be consistent with historic patterns. Consistency with established patterns indicates acceptable amplification, retention times, peak height, and peak shape. Therefore, PCR and DHPLC conditions (machine and buffers, etc.) are performed as specified in the Examples. Homologues, or other non-specific amplification signals are absent as indicated by comparison with the established normal control pattern.

3. Positive Control

The positive controls are "DHPLC analytical condition controls" used to demonstrate that the established DHPLC analytical conditions (which detect the positive control heteroduplex) are in effect at the time of analysis. A positive control pattern distinct from normal control and consistent with historic patterns indicates acceptable retention time, peak height(s), peak shape and pattern. Heteroduplex detection indicates that the specific DHPLC analysis conditions optimal for the individual fragment were in effect during patient analysis. It is important to note that these controls are not necessarily PKD positive signals. Specific PKD positive samples for each of the 83 PKD fragments are not available. In their absence, another heteroduplex (positive and normal control) is used as the positive indicator demonstrating appropriate analytical conditions at the time of analysis.

4. Additional Positive Controls

Additional positive controls provide pattern(s) consistent with historic patterns for this specific mutation and may be used to separate out very common polymorphisms. Generally, a specific DNA variant will generate a unique signature heteroduplex pattern that is highly reproducible from sample to sample. A pattern consistent with the established pattern indicates acceptable retention time, peak height(s), peak shape and pattern. The specific heteroduplex pattern demonstrates that specific DHPLC analysis conditions optimal for this DNA variant were in effect during patient analysis and, therefore, patient patterns matching this can be considered to possess the common polymorphism. This optional separating method for common polymorphisms is highly specific to the unique amplicon and variant and is dependent upon appropriate validation studies unique to the variant.

D. Analyzing DHPLC Results

Since DBPLC is a separating process, any specimen (e.g., DNA, or cell lysate or tissue sample) with a signal that differs from the normal control should be considered a potential positive and treated by one of several options available depending on the circumstances. For some embodiments, a signal that is too week to interpret (less than 25% of the normal control peak height) could be caused by PCR failure, Wave injection failure, or some other sporadic instrumentation problem unique to the sample. Options include repeat from the point of PCR, repeat the Wave injection (with all controls), or report the wave result as inconclusive and proceed to sequencing. A signal that differs from the normal control in pattern should be considered positive, scored as "P", and sequenced. A signal that differs very slightly from the normal control pattern should be scored as "B" and sequenced. A signal that is much stronger than the normal control signal should be scored as "P" and sequenced. Note that no patient specimens will be resulted based on these results alone. The specific options utilized will vary with the amplicon and its DHPLC performance history, and the specific circumstances for the specimen.

In some embodiments, the only results released from the DHPLC results will be those scored as "normal" by Wave analysis. In order to be scored as normal, the specimen's DHPLC pattern must be consistent with the normal control by the following QC criteria: (a) peak number, (b) peak height, (c) peak pattern, (d) retention time, (e) baseline shape. In other words, the pattern for the individual specimen must look like the normal control, within a reasonable expected range of variation. Consult with the validation data reference patterns if necessary. The sensitivity of DHPLC separating was assessed by counting patterns that differ substantially from the normal control. When a pattern genuinely appears to differ from the normal control, there should be no doubt—it is scored as positive and sent on for sequencing. Only those that meet the requirements for that specific amplicon and have a pattern consistent with the normal control should be scored and released as normal.

Specific numerical criteria used for judging "consistent with" include, but are not limited to, (a) number of peaks where a peak represents a local maximum in the signal intensity, (b) peak heights, or maximum signal intensities, which are usually between 0.5 and 2.0 times the height of the normal control, (c) retention time of peaks, which must be +/−60 seconds compared to the corresponding normal controls. Peak pattern is judged by relative correspondence of each slope change within a peak, and relative intensities and retention times of individual peaks within a complex pattern. Baseline patterns are usually smooth and consistent in all samples. A relatively low baseline change may represent a heteroduplex that elutes and perhaps melts at considerably different retention times from the homoduplex peak(s). The retention time and peak height criteria for each amplicon are specified in the attached tables in the Examples.

In one embodiment, the peak pattern assessment is a combination of (1) the sample signal satisfying the same run control criteria as the normal control, and (2) the sample signal pattern being consistent with the normal control based on the relative comparison for that run. Normal control patterns are expected to vary slightly from run to run, and still be acceptable, so individual samples scored as normal are a combination of satisfying (1) the same run control criteria as the normal control, (2) the relative control criteria inherent in the comparison of the normal control to each patient sample, described above. It seems clear that subtle changes in the pattern of the patient sample might be consistent with the absolute run criteria for the normal control, yet be clearly distinct using relative comparison of normal and patient within a run. The relative comparison within a run always supercedes historic patterns, assuming the normal control has passed control criteria and the run is accepted.

IX. Verification of Heteroduplex

Optionally, the identified heteroduplex may be verified by means of digesting the amplification products with one or more restriction enzymes. The restriction enzymes useful for this purpose are selected by comparing the sequences of authentic PKD genes and PKD homologues, or by comparing PKD polymorphisms Useful restriction enzymes according to the invention generate distinguishable fragment profiles for an authentic PKD gene and a PKD homologue. Examples of such restriction enzymes include, but are not limited to, Pst I, Stu I, Xma I, Mlu I, Pvu II, BssHII, Fsp I, Msc I, and Bln I. Useful restriction enzymes may also generate distinguishable fragment profile for a normal PKD gene and a mutant PKD gene. It is understood that more restriction enzymes may be identified by simply comparing the sequence of a PKD gene and a PKD homologue gene or a normal PKD allele and a mutant PKD allele. A restriction enzyme with its recognition site or cleavage site in one sequence altered so as to abolish or create a cleavage site but not in the other sequence may be considered a useful restriction enzyme for the subject invention. Restriction of nucleic acids is followed by separation of the resulting fragments and analysis of fragment length or differential fragment migration in denaturing high-performance liquid chromatography (DHPLC) or gel electrophoresis, as above, including restriction-capillary electrophoresis.

X. Sequencing of Heteroduplexes Identified by DHPLC

Heteroduplex indicating the presence of one or more mutation, identified by DHPLC, may be cloned, amplified, and/or sequenced. Any known sequencing method known in the art can be used to sequence the heteroduplex. In some embodiments, the heteroduplex identified was used as template for PCR amplification and amplified products are sequenced by Sequetech Corporation (Mountain View, Calif.). In a preferred embodiment, sequencing is carried out by using one of the primers with SEQ ID NOs. 3–49.

In some embodiments, the identified heteroduplex is amplified and cloned into a plasmid (e.g., Zero Blunt TOPO PCR cloning kit, Invitrogen, Carlsbad, Calif., Cat #4560-01) before sequencing. The plasmid containing the PCR fragment is then propagated by well known methods in the art before subject to sequencing.

XI. Clinical Use of the Method

The genetic testing method described in this application is targeted toward identifying DNA alterations in the coding region of the PKD-1 or PKD-2 gene, including the splice junction acceptor/donor sequences, which have been reported to cause ADPKD. The method can be performed to assists physicians to:

A. Diagnose PKD-caused ADPKD in symptomatic individuals.

B. Follow up on ultrasound results indicating the presence of one or two cysts in an individual at or near the age of onset.

C. Diagnose between different variants of ADPKD (type 1 and 2), which is not feasible to determine from family history, ultrasound and other clinical data.

D. Determine and provide genetic counseling for other at-risk family members once an ADPKD proband has been identified in a family.

E. Determine the suitability of a living related donor in transplantation cases.

XII. Kits

The invention also provides kits for performing the mutation analysis method and the PKD patient identification method of the invention. Embodiments of the subject kits, in accordance with the methods of the invention, include at least one isolated first nucleic acid and at least one isolated second nucleic acid, where the first nucleic acid is selected from the group of SEQ ID NOs. 3–49 and their complementary sequences, and the second nucleic acid has an opposite orientation from the first nucleic acid, and where the first and second nucleic acids amplify a fragment of a template nucleic acid comprising a sequence of SEQ ID NO. 1 or 2, and packaging materials therefore. The kit of the invention may further comprises at least one component selected from the group consisting of: a DNA polymerase, a template nucleic acid, a restriction enzyme, a control oligonucleotide primer, ddNTPs, a PCR reaction buffer and the combination thereof. Kits of the invention, in addition to the reagents, preferably include written instructions for performing the subject methods. Kits are preferably packaged in a unit container and may contain the reagents in pre-measured amounts designed to operate with each other so as to produce the desired result.

EXAMPLES

The invention is illustrated by the following non-limiting examples wherein the following materials and methods are employed.

Example 1

Reagents, Special Supplies and Equipment

A. Chemicals

The following is a listed of chemicals used for PKD-1 amplification and DHPLC (WAVE) analysis.

1% Agarose, 1×TBE, 54 Well Gel with Ethidium Bromide (Embitec, Catalog Number GE 4580)

2% Agarose, 1×TBE, 54 Well Gel with Ethidium Bromide (Embitec, Catalog Number GE 4582)

96 Well Gel Filtration Block (Edge Biosystems, Catalog Number 91751)

Quickstep™ 96 Well PCR Purification Kit (Edge Biosystems, Catalog Number 99605)

AmpliTaq Gold with GeneAmp PCR Buffer II & $MgCl_2$ Solution (Perkin Elmer, Catalog Number N808-0241)

rTth DNA Polymerase, XL & XL Buffer II Pack (Perkin Elmer, Catalog Number N808-00193)

TapPlus Precision PCR System (Stratagene, Catalog Number 600211)

Dimethyl Sulphoxide (DMSO) (Sigma, Catalog Number D-2650)

Ready-Load 100 bp DNA Ladder or Equivalent (Gibco BRL, Catlaog Number 10380-012)

Ready-Load 1 kb DNA Ladder or Equivalent (Gibco BRL, 1800-828-6686, Catlaog Number 10381-010)

Big Dye Terminator Ready Reaction Kit (Perkin Elmer, Catalog Number 4303150)

Gel Filtration Cartridge (Edge Biosystems, Catalog Number 42453)

Long Ranger Singel™ packs (FMC BioProducts, Catalog Number 50691 or 50693).

Oligonucleotides (Operon Technologies, Inc.)

WAVE Mutation Standard (209 bp), Catalog Number 560077 (180 ul)

Acetonitrile-HPLC Grade (VWR, Catalog Number BJ015-1)

HPLC Grade Water (VWR, Catalog Number BJ365-4)

Triethylammoniun Acetate (TEAA) (Transgenomic, Catalog Number SP5890)

B. Reagents and Solutions

10 $\mu$M oligonucleotide primers: 10 $\mu$M working aliquots of PCR primers dissolved in TE buffer should be stored at 4° C. in Pre-PCR refrigerator; sequencing primer working aliquots should be stored at 4° C. in Post-PCR refrigerator.

Solution X-127: Upgrade Blue Dextran in 50 mM EDTA (pH=8.0)

Combine 0.5 ml 50 mM EDTA pH=8.0 (Solution X-35), 500 mg Blue Dextran AND 9.5 ml AUTOCLAVED, STERILE FILTERED $DiH_2O$ in a sterile 15 ml conical centrifuge tube. Thoroughly mix the solution by vortexing.

Solution X-126: Upgrade Gel Loading Buffer: Combine 200 $\mu$l deionized Formamide and 40 $\mu$l Upgrade Blue Dextran in 50 mM EDTA (Solution X-127) in a 1.5 ml sterile microcentrifuge tube. Vortex thoroughly.

WAVE Solution A: Solution A (0.025% ACN)

| Preparation of 2L: | 100 ml Ion Pairing Agent (TEAA)<br>500 $\mu$l Acetonitrile (ACN)<br>Top to 2L with HPLC grade water |
|---|---|

WAVE Solution B: Solution B (25% ACN)

| Preparation of 2L: | 100 ml Ion Pairing Agent (TEAA)<br>500 ml Acetonitrile (ACN)<br>Top to 2L with HPLC grade water |
|---|---|

WAVE Syringe Wash Solution: Syringe Wash (8% ACN)

| Preparation of 2L: | 160 ml Acetonitrile (ACN)<br>Top to 2L with HPLC grade water |
|---|---|

WAVE Solution D: Solution D (75% ACN)

| Preparation of 2L: | 500 ml HPLC grade water<br>Top to 2L with Acetonitrile (ACN) |
|---|---|

C. Equipment and Special Supplies

TABLE 5

| | |
|---|---|
| Perkin Elmer<br>761 Main Avenue<br>Norwalk, CT 06859 | ABI Prism ™ 377 DNA Sequencer |
| VWR Scientific Products<br>P.O. Box 232<br>Boston, MA 02101 | 1. Beckman Allegra ™ 21 Centrifuge<br>2. Eppendorf Microcentrifuge 5415C<br>3. Multichannel pipet<br>4. Sterile reservoirs<br>5. DURX 670 wipers<br>6. VWR Model 1300U Oven |
| Transgenomic, Inc.<br>12325 Emmet Street<br>Omaha, NE 68164 | WAVE Nucleic Acid Fragment<br>Analysis System |

Example 2

Procedure

Stage I: Preparation of DNA and/or RNA from Patient Specimens

DNA is extracted from whole blood or lymphocytes using the Puregene® DNA extraction kit. DNA extracted using these reagents should be successfully PCR amplified under the conditions specific to the assay. This is tested by performing the assay as specified in the protocol and comparing the results obtained with the positive DNA control that has been previously validated.

Extracted DNA is quantitated and the 260/280 ratio is 1.4 or greater. Samples with lower ratios indicate that the quality of DNA is poor and may not meet PCR standards. If end results of the assay are not interpretable the sample should be re-extracted.

Stage II: Amplification of DNA by PCR

PCR reaction mixtures and cycling parameters (e.g., for exon 1 of PKD-1 gene) were set up as illustrated in Table 5. PCR conditions were set up similarly, but optimized for specific and efficient amplification of other exons.

TABLE 6

PCR Reaction Master Mix Component Concentrations and Thermal Cycling Conditions For First round PCR Products 1–8 (L1–L8)
LOWER MASTER MIX:

| Component: | Reaction Concentration | Volume/reaction |
|---|---|---|
| Water | — | 13.0 ul |
| 10X Buffer | 1X | 2.0 ul |
| Mg(Oac)$_2$ | 0.9 mM | None |
| dNTP mix | 200 uM | 1.0 ul |
| Primer 1 | 0.25 uM | 1.25 ul |
| Primer 2 | 0.25 uM | 1.25 ul |
| DMSO | 7.5% | 1.5 ul |
| TOTAL VOLUME | | 20 ul |

One wax bead was added to each well and incubated in a thermal cycler @ 80° C. for 5 minutes to melt the wax and incubated at 25° C. for an additional 5 minutes before placed on ice for further handling.

UPPER MASTER MIX:

| Component: | Reaction Concentration | Volume/reaction |
|---|---|---|
| Water | — | 23.15 ul |
| 10X Buffer | 1X | 3.0 ul |
| TaqPlus Precision Polymerase mixture | 5U/rxn | 1.0 ul |
| DMSO | 7.5% | 2.25 ul |
| TOTAL VOLUME | | 29.4 ul |
| Genomic DNA @ 500 ng/ul | | 0.6 ul |

Cycling Parameters

| Melting the Wax | | Amplification | |
|---|---|---|---|
| 80° C. 5 min | 1 cycle | 94° C. 3 min | 1 cycle |
| 25° C. forever | | 96° C. 30 sec | |
| | | 68° C. 20 sec | 35 cycles |
| | | 72° C. 3 min + 4 sec/cycle | |
| | | 72° C. 10 min | 1 cycle |

*Add Upper Master Mix and DNA before proceeding to next cycling step.

TABLE 7

Example of nested PCR reaction setup

| REAGENT | STOCK CONCEN-TRATION | VOLUME PER REACTION | REACTION CONCEN-TRATION |
|---|---|---|---|
| Water | — | 31.0 μl | — |
| Buffer II | 10X | 5.0 μl | 1X |
| MgCl$_2$ | 25 mM | 2.0 μl | 1.0 mM |
| DNTP mix | 10 mM each | 1.0 μl | 200 μM each |
| CAD-18-PF1 (primer) | 10 μM | 3.0 μl | 0.6 μM |
| CAD-18-PR1 (primer) | 10 μM | 3.0 μl | 0.6 μM |
| DMSO | 100% | 2.5 μl | 5% |
| Amplitaq Gold | 5 U/μl | 0.5 μl | 2.5 U |
| TOTAL | | 48.0 μl | |

TABLE 8

Summary of Amplification Conditions For Exons

| CYCLE NUMBER | TEMPERATURE | TIME | DESCRIPTION |
|---|---|---|---|
| 1 cycle | 94° C. | 10 min | AmpliTaq Gold activation |
| | 92° C. | 1 min | Denaturing |
| 35 cycles | 55° C. | 1 min | Annealing |
| | 72° C. | 1 min | Extension |
| 1 cycle | 72° C. | 10 min | Final extension |
| (hold) | 4° C. | forever | |

PCR amplified fragments may be compared in size, signal intensity and migration pattern with positive control DNA control that has been previously validated. The size of the PCR amplified fragments is determined by comparison to the Molecular weight marker (DNA MASS™ Ladder-Gibco BRL) on the gel. The low range DNA Mass Ladder gives 6 bands of double stranded (100–2000 bp) DNA on staining the gel with ethidium bromide.

Stage III: DHPLC Analysis of PCR Products

Heteroduplexes formed by PCR amplified products are analyzed using WAVE nucleic acid fragment analysis system from Transgenomic, Inc. (Omaha, Neb. 68164).

Stage IV: Cycle Sequencing

Tables 9 and 10 provide examples of sequencing conditions used in one embodiment of the invention.

TABLE 9

Sequencing Reaction Master Mix Component

| REAGENT | STOCK CONCENTRATION | VOLUME PER REACTION | REACTION CONCENTRATION |
|---|---|---|---|
| Water | — | 14.0 µl | — |
| Big Dye Terminator Ready Reaction Mix | 2.5X | 4.0 µl | 0.5X |
| Primer | 10 µM | 1.0 µl | 0.5 µM |
| FINAL VOLUME | | 19.0 µl | |

TABLE 10

Cycle Sequencing Conditions

| CYCLE NUMBER | TEMPERATURE | TIME | DESCRIPTION |
|---|---|---|---|
| 30 cycles | 94° C. | 10 sec | Denaturing |
| | 55° C. | 5 sec | Annealing |
| | 60° C. | 4 min | Extension |
| (hold) | 4° C. | forever | |

Example 3

Summary of Results

Figure 4:
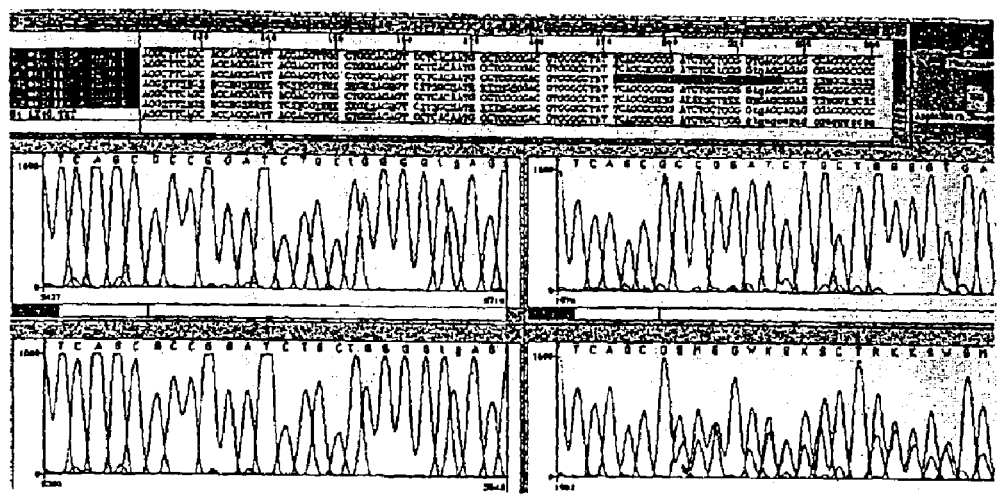
FIG. 4 is a graph showing PKD1 exon 40 sequences of the normal control and a sequence with a 19 bp insertion (duplication) at nucleotide 11606, codon 3799 according to one embodiment.
Figure 5:
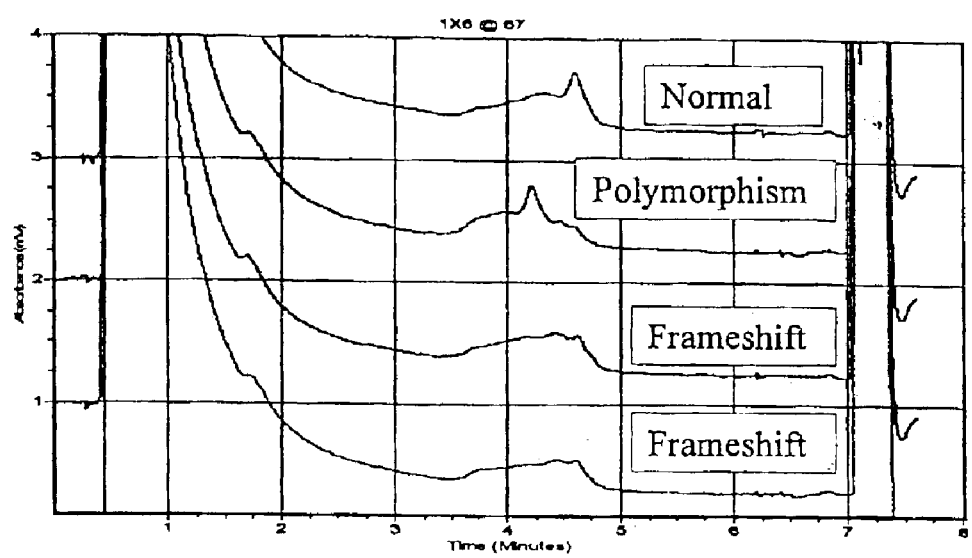
FIG. 5 is a graph showing PKD1 exon 6 DHPLC patterns of an intron 5 probable polymorphism (IVS5-9 G->A) and a frameshift at nucleotide 1502 (insert G) in two related patients according to one embodiment.
Figure 6:
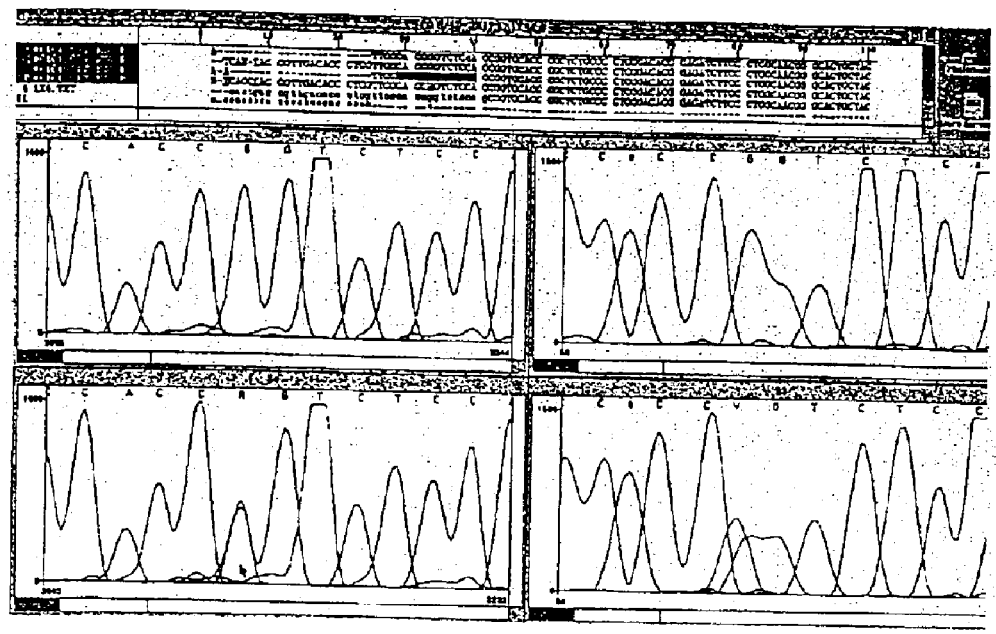
FIG. 6 is a graph showing PKD1 exon 6 sequences of the normal control and a sequence with intron 5 probable polymorphism (IVS5-9 G->A) according to one embodiment.
Figure 7:
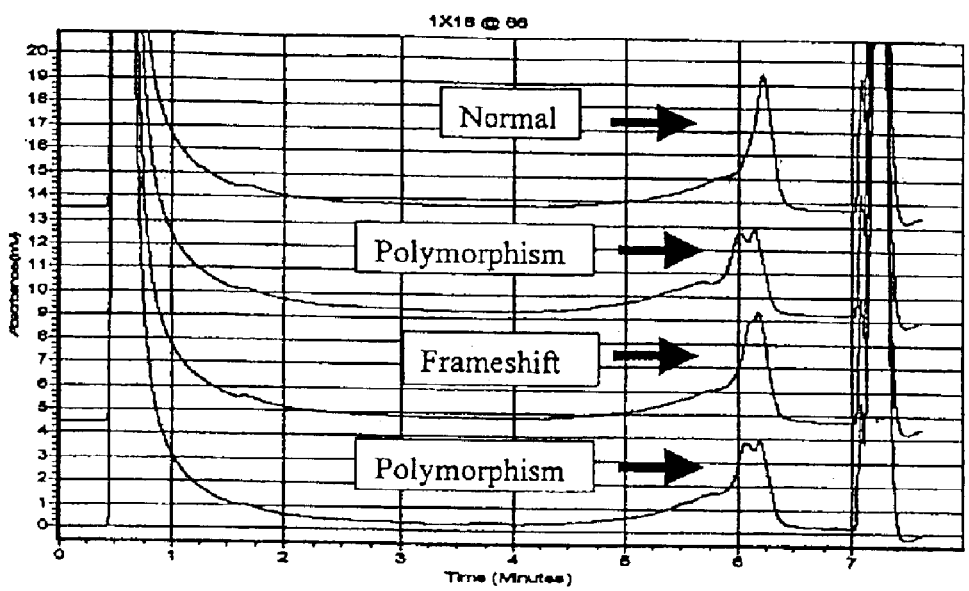
FIG. 7 is a graph showing PKD 1 exon 18 DHPLC patterns of a frameshift at nucleotide 7518, codon 2436 (insert C), and a common polymorphism C7652T according to one embodiment.
Figure 8:
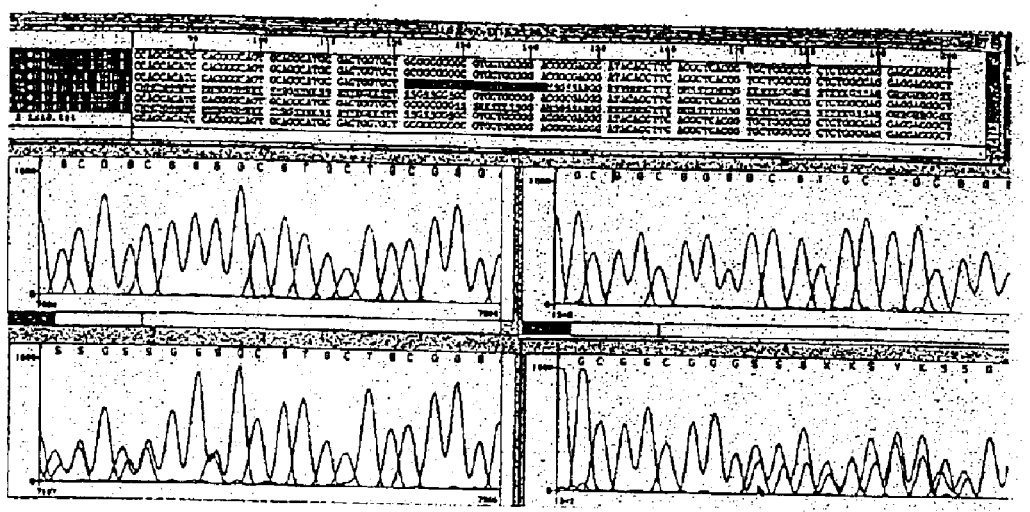
FIG. 8 is a graph showing PKD1 exon 18 sequences of the normal control and a sequence with frameshift at nucleotide 7518, codon 2436 (insert C) according to one embodiment.
Figure 9:
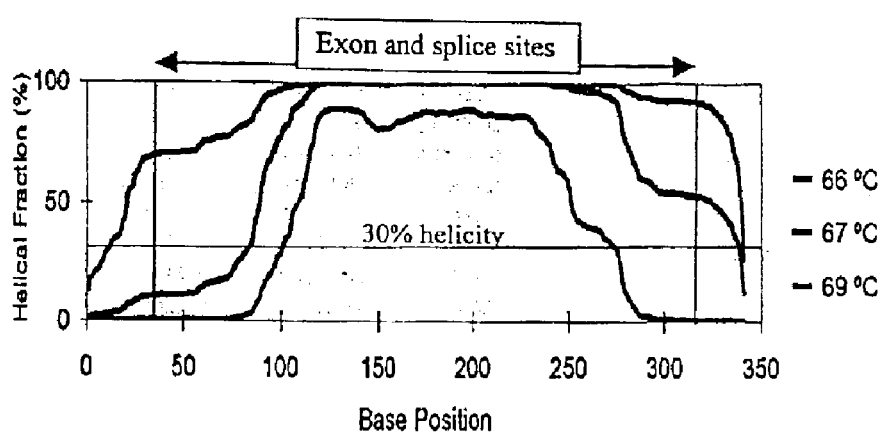
FIG. 9 is a graph showing an example of a software-predicted melt profile and the need for multiple temperatures to establish partial melting near the ends of an exon according to one embodiment.
Figure 10:
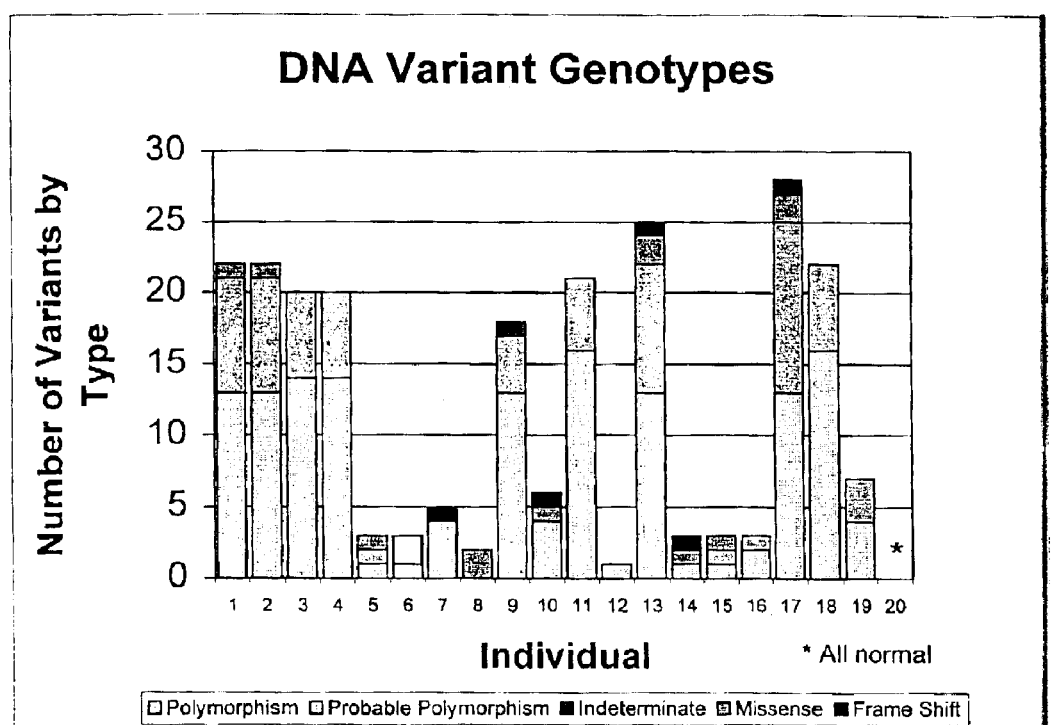
FIG. 10A is a chart showing patient DNA variant genotypes determined in one embodiment of the invention.
FIG. 10B is a table showing patient DNA variant genotypes determined in one embodiment of the invention.
Figure 13:
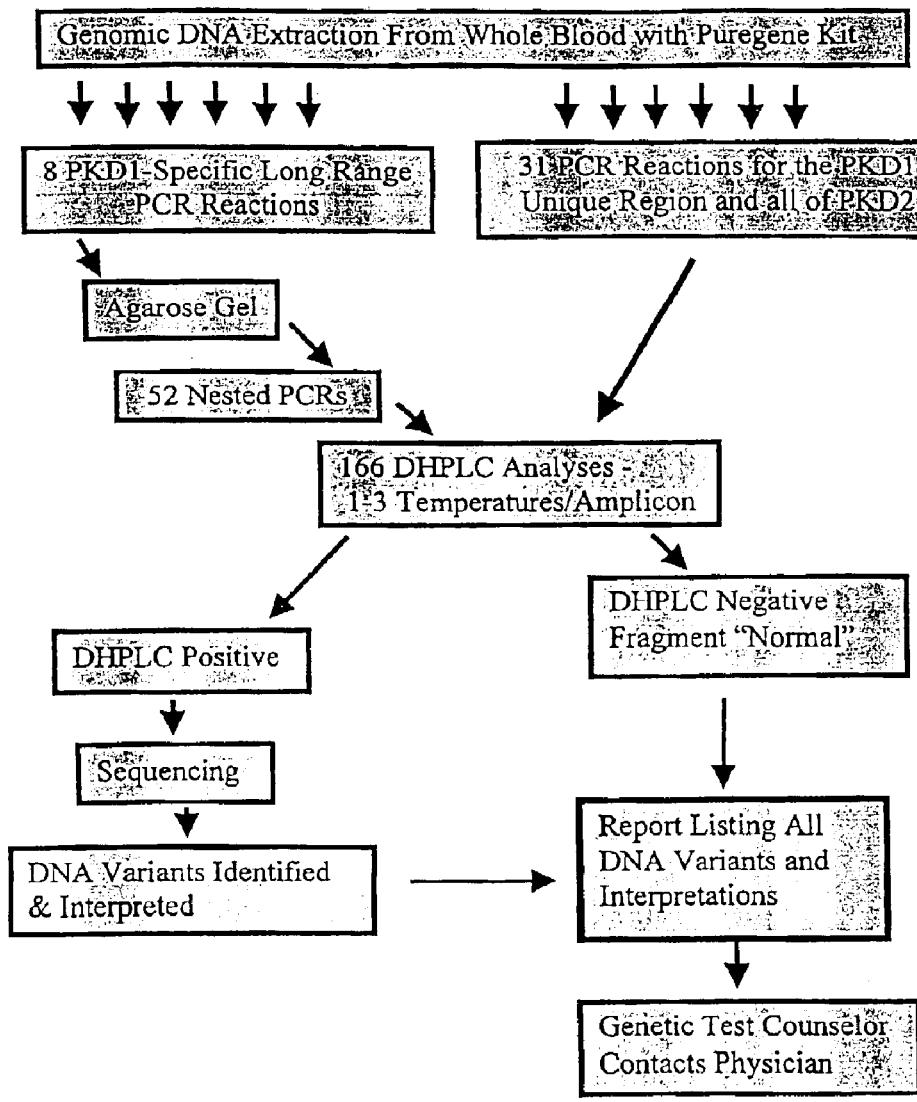
FIG. 13 is a schematic diagram showing patient specimen processing steps in one embodiment of the invention.

In one experiment, detection of mutations in exons 1–34 of the PKD-1 gene was achieved by using eight sets of oligonucleotide primers in eight separate first round PCR reaction to amplify DNA fragments of the following sizes: a) LR1 was 2.2 kb and contains exon 1. b) LR2 was 4.6 kb and contains exons 2–7. c) LR3 was 4.2 kb and contains exons 8–12. d) LR4 was 4.4 kb and contains exons 13–15. e) LR5 was 3.4 kb and contains exons 15 (3'-end) through 21. f) LR6 was 0.3 kb and consists of exon 22. g) LR7 was 4.2 kb and contains exons 23–28. h) LR8 was 5.8 kb and contained exons 29–34 of the duplicated region of the gene. The amplified product from the first round of amplification were then serially diluted to 1:10$^4$ or 1:10$^5$ to remove genomic contamination and subsequently used as template in a second round of nested PCR. The nested PCR products were heteroduplexed and screened for sequence alterations by DHPLC. Each fragment was analyzed against a normal and positive control using a temperature and acetonitrile gradient specific to the amplicon. Any samples testing positive by DHPLC analysis were subsequently purified and sequenced. Cycle sequenced products were then separated on an ABI 377 automated sequencer and the results were analyzed using an assortment of sequencing software. Tables 11–12 and FIGS. 1 to 13 illustrate the results and procedures of some embodiments of the invention.

TABLE 11

Numbers of products analyzed for each PKD gene

| Analysis: | PKD-1 | PKD-2 | Total |
|---|---|---|---|
| First Round PCRs | 8 | — | 8 |
| Amplicons | 66 | 17 | 83 |
| DHPLC analyses | 133 | 33 | 166 |
| Base Pairs evaluated | 13,830 | 3204 | 17,034 |

TABLE 12

Variant detection rates

| Source of Variant | Naturally occuring - Independent Sequence confirmed | Naturally occuring - SSCP Separated | Mutagenesis Sequence confirmed | Gene Total |
|---|---|---|---|---|
| PKD-1 | 14/18 | 15/17 | 45/47 | 74/82 |
| | 78% | 88% | 96% | 90% |
| PKD-2 | 20/21 | 0/0 | 22/23 | 42/44 |
| | 95% | | 96% | 95% |
| Type total | 34/39 | 15/17 | 67/70 | 116/126 |
| | 87% | 88% | 96% | 92% |

OTHER EMBODIMENTS

The foregoing examples demonstrate experiments performed and contemplated by the present inventors in making and carrying out the invention. It is believed that these examples include a disclosure of techniques which serve to both apprise the art of the practice of the invention and to demonstrate its usefulness. It will be appreciated by those of skill in the art that the techniques and embodiments disclosed herein are preferred embodiments only and that in general numerous equivalent methods and techniques may be employed to achieve the same result. All applications, patents and literature referred to in the specification are hereby incorporated by reference, in their entirety, including figures and tables.

SEQUENCE LISTING

<160> NUMBER OF SEQ ID NOS: 168

<210> SEQ ID NO 1
<211> LENGTH: 14136
<212> TYPE: DNA
<213> ORGANISM: Homo sapiens

<400> SEQUENCE: 1

```
gcactgcagc gccagcgtcc gagcgggcgg ccgagctccc ggagcggcct ggccccgagc      60
cccgagcggg cgtcgctcag cagcaggtcg cggccgcgca gccccatcca gccccgcgcc     120
cgccatgccg tccgcgggcc ccgcctgagc tgcggtctcc gcgcgcgggc gggcctgggg     180
```

-continued

```
acggcggggc catgcgcgcg ctgccctaac gatgccgccc gccgcgcccg cccgcctggc    240
gctggccctg ggcctgggcc tgtggctcgg ggcgctggcg ggggggcccg ggcgcggctg    300
cgggccctgc gagcccccct gcctctgcgg cccagcgccc ggcgccgcct gccgcgtcaa    360
ctgctcgggc cgcgggctgc ggacgctcgg tcccgcgctg cgcatccccg cggacgccac    420
agcgctagac gtctcccaca acctgctccg ggcgctggac gttgggctcc tggcgaacct    480
ctcggcgctg gcagagctgg atataagcaa caacaagatt tctacgttag aagaaggaat    540
atttgctaat ttatttaatt taagtgaaat aaacctgagt gggaacccgt ttgagtgtga    600
ctgtggcctg gcgtggctgc cgcgatgggc ggaggagcag caggtgcggg tggtgcagcc    660
cgaggcagcc acgtgtgctg ggcctggctc cctggctggc cagcctctgc ttggcatccc    720
cttgctggac agtggctgtg gtgaggagta tgtcgcctgc ctccctgaca acagctcagg    780
caccgtggca gcagtgtcct tttcagctgc ccacgaaggc ctgcttcagc cagaggcctg    840
cagcgccttc tgcttctcca ccggccaggg cctcgcagcc ctctcggagc agggctggtg    900
cctgtgtggg gcggcccagc cctccagtgc ctcctttgcc tgcctgtccc tctgctccgg    960
cccccccgcca cctcctgccc ccacctgtag ggccccacc ctcctccagc acgtcttccc   1020
tgcctcccca ggggccaccc tggtggggcc ccacggacct ctggcctctg ccagctagc   1080
agccttccac atcgctgccc cgctcccgt cactgccaca cgctgggact tcggagacgg   1140
ctccgccgag gtggatgccg ctgggccggc tgcctcgcat cgctatgtgc tgcctgggcg   1200
ctatcacgtg acgccgtgc tggccctggg gccggctca gccctgctgg ggacagacgt   1260
gcaggtggaa gcggcacctg ccgccctgga gctcgtgtgc ccgtcctcgg tgcagagtga   1320
cgagagcctt gacctcagca tccagaaccg cggtggttca ggcctggagg ccgcctacag   1380
catcgtggcc ctgggcgagg agccggcccg agcggtgcac ccgctctgcc cctcggacac   1440
ggagatcttc cctggcaacg ggcactgcta ccgcctggtg gtggagaagg cggcctggct   1500
gcaggcgcag gagcagtgtc aggcctgggc cggggccgcc ctggcaatgg tggacagtcc   1560
cgccgtgcag cgcttcctgg tctcccgggt caccaggagc ctagacgtgt ggatcggctt   1620
ctcgactgtg caggggggtgg aggtgggccc agcgccgcag ggcgaggcct tcagcctgga   1680
gagctgccag aactggctgc ccggggagcc acacccagcc acagccgagc actgcgtccg   1740
gctcgggccc accgggtggt gtaacaccga cctgtgctca gcgccgcaca gctacgtctg   1800
cgagctgcag cccggaggcc cagtgcagga tgccgagaac ctcctcgtgg gagcgcccag   1860
tggggacctg cagggacccc tgacgcctct ggcacagcag gacggcctct cagccccgca   1920
cgagcccgtg gaggtcatgg tattcccggg cctgcgtctg agccgtgaag ccttcctcac   1980
cacggccgaa tttgggaccc aggagctccg gcggcccgcc cagctgcggc tgcaggtgta   2040
ccggctcctc agcacagcag ggaccccgga gaacggcagc gagcctgaga gcaggtcccc   2100
ggacaacagg acccagctgg ccccccgcgt catgccaggg ggacgctggt gcctggagc   2160
caacatctgc ttgccgctgg acgcctcttg ccaccccag gcctgcgcca atggctgcac   2220
gtcagggcca gggctacccg ggccccccta tgcgctatgg agagagttcc tcttctccgt   2280
tgccgcgggg ccccccgcgc agtactcggt caccctccac ggccaggatg tcctcatgct   2340
ccctggtgac ctcgttggct tgcagcacga cgctggccct ggcgcctcc tgcactgctc   2400
gccggctccc ggccaccctg gtccccaggc ccgtacctc tccgccaacg cctcgtcatg   2460
gctgccccac ttgccagccc agctggaggg cacttgggcc tgccctgcct gtgcctgcg   2520
gctgcttgca gccacggaac agctcaccgt gctgctgggc ttgaggccca accctggact   2580
```

-continued

```
gcggatgcct gggcgctatg aggtccgggc agaggtgggc aatggcgtgt ccaggcacaa   2640
cctctcctgc agctttgacg tggtctcccc agtggctggg ctgcgggtca tctaccctgc   2700
cccccgcgac ggccgcctct acgtgcccac caacggctca gccttggtgc tccaggtgga   2760
ctctggtgcc aacgccacgg ccacggctcg ctggcctggg ggcagtgtca gcgcccgctt   2820
tgagaatgtc tgccctgccc tggtggccac cttcgtgccc ggctgcccct gggagaccaa   2880
cgatacctg ttctcagtgg tagcactgcc gtggctcagt gaggggagc acgtggtgga    2940
cgtggtggtg gaaaacagcg ccagccgggc caacctcagc ctgcgggtga cggcggagga   3000
gcccatctgt ggcctccgcg ccacgcccag ccccgaggcc cgtgtactgc agggagtcct   3060
agtgaggtac agccccgtgg tggaggccgg ctcggacatg gtcttccggt ggaccatcaa   3120
cgacaagcag tccctgacct ccagaacgt ggtcttcaat gtcatttatc agagcgcggc    3180
ggtcttcaag ctctcactga cggcctccaa ccacgtgagc aacgtcaccg tgaactacaa   3240
cgtaaccgtg gagcggatga acaggatgca gggtctgcag gtctccacag tgccggccgt   3300
gctgtccccc aatgccacgc tagcactgac ggcgggcgtg ctggtggact cggccgtgga   3360
ggtggccttc ctgtggaact ttggggatgg ggagcaggcc ctccaccagt tccagcctcc   3420
gtacaacgag tccttcccgg ttccagaccc ctcggtggcc caggtgctgg tggagcacaa   3480
tgtcatgcac acctacgctg ccccaggtga gtacctcctg accgtgctgg catctaatgc   3540
cttcgagaac ctgacgcagc aggtgcctgt gagcgtgcgc gcctccctgc cctccgtggc   3600
tgtgggtgtg agtgacggcg tcctggtggc cggccggccc gtcaccttct acccgcaccc   3660
gctgccctcg cctggggtg ttctttacac gtgggacttc ggggacggct ccctgtcct    3720
gacccagagc cagccggctg ccaaccacac ctatgcctcg agggcacct accacgtgcg    3780
cctggaggtc aacaacacgg tgagcggtgc ggcggcccag gcggatgtgc gcgtctttga   3840
ggagctccgc ggactcagcg tggacatgag cctggccgtg gagcagggcg cccccgtggt   3900
ggtcagcgcc gcggtgcaga cgggcgacaa catcacgtgg accttcgaca tggggacgg    3960
caccgtgctg tcgggcccgg aggcaacagt ggagcatgtg tacctgcggg cacagaactg   4020
cacagtgacc gtgggtgcgg ccagccccgc cggccacctg gcccggagcc tgcacgtgct   4080
ggtcttcgtc ctggaggtgc tgcgcgttga accgccgcc tgcatcccca cgcagcctga    4140
cgcgcggctc acggcctacg tcaccgggaa cccggcccac tacctcttcg actggacctt   4200
cggggatggc tcctccaaca cgaccgtgcg ggggtgcccg acggtgacac acaacttcac   4260
gcggagcggc acgttccccc tggcgctggt gctgtccagc cgcgtgaaca gggcgcatta   4320
cttcaccagc atctgcgtgg agccagaggt gggcaacgtc accctgcagc cagagaggca   4380
gtttgtgcag ctcggggacg aggcctggct ggtggcatgt gcctggcccc cgttcccta    4440
ccgctacacc tgggactttg gcaccgagga agccgccccc acccgtgcca ggggccctga   4500
ggtgacgttc atctaccgag acccaggctc ctatcttgtg acagtcaccg cgtccaacaa   4560
catctctgct gccaatgact cagccctggt ggaggtgcag gagcccgtgc tggtcaccag   4620
catcaaggtc aatggctccc ttgggctgga gctgcagcag ccgtacctgt tctctgctgt   4680
gggccgtggg cgccccgcca gctacctgtg ggatctgggg gacggtgggt ggctcgaggg   4740
tccggaggtc acccacgctt acaacagcac aggtgacttc accgttaggg tggccggctg   4800
gaatgaggtg agccgcagcg aggcctggct caatgtgacg gtgaagcggc gcgtgcgggg   4860
gctcgtcgtc aatgcaagcc gcacggtggt gcccctgaat gggagcgtga gcttcagcac   4920
```

-continued

| | |
|---|---|
| gtcgctggag gccggcagtg atgtgcgcta ttcctgggtg ctctgtgacc gctgcacgcc | 4980 |
| catccctggg ggtcctacca tctcttacac cttccgctcc gtgggcacct tcaatatcat | 5040 |
| cgtcacggct gagaacgagg tgggctccgc ccaggacagc atcttcgtct atgtcctgca | 5100 |
| gctcatagag gggctgcagg tggtgggcgg tggccgctac ttccccacca accacacggt | 5160 |
| acagctgcag gccgtggtta gggatggcac caacgtctcc tacagctgga ctgcctggag | 5220 |
| ggacaggggc ccggccctgg ccggcagcgg caaaggcttc tcgctcaccg tgctcgaggc | 5280 |
| cggcacctac catgtgcagc tgcgggccac caacatgctg ggcagcgcct gggccgactg | 5340 |
| caccatggac ttcgtggagc ctgtggggtg gctgatggtg accgcctccc cgaacccagc | 5400 |
| tgccgtcaac acaagcgtca ccctcagtgc cgagctggct ggtggcagtg tgtcgtata | 5460 |
| cacttggtcc ttggaggagg ggctgagctg ggagacctcc gagccattta ccacccatag | 5520 |
| cttccccaca cccggcctgc acttggtcac catgacggca gggaacccgc tgggctcagc | 5580 |
| caacgccacc gtgaagtgga atgtgcaggt gcctgtgagt ggcctcagca tcagggccag | 5640 |
| cgagcccgga ggcagcttcg tggcggccgg gtcctctgtg ccttttggg ggcagctggc | 5700 |
| cacgggcacc aatgtgagct ggtgctgggc tgtgcccggc ggcagcagca agcgtggccc | 5760 |
| tcatgtcacc atggtcttcc cggatgctgg caccttctcc atccggctca atgcctccaa | 5820 |
| cgcagtcagc tgggtctcag ccacgtacaa cctcacggcg gaggagccca tcgtgggcct | 5880 |
| ggtgctgtgg gccagcagca aggtggtggc gcccgggcag ctggtccatt ttcagatcct | 5940 |
| gctggctgcc ggctcagctg tcaccttccg cctgcaggtc ggcggggcca cccgaggt | 6000 |
| gctccccggg ccccgtttct cccacagctt ccccgcgtc ggagaccacg tggtgagcgt | 6060 |
| gcggggcaaa aaccacgtga gctgggccca ggcgcaggtg cgcatcgtgg tgctggaggc | 6120 |
| cgtgagtggg ctgcagatgc ccaactgctg cgagcctggc atcgccacgg gcactgagag | 6180 |
| gaacttcaca gcccgcgtgc agcgcggctc tcgggtcgcc tacgcctggt acttctcgct | 6240 |
| gcagaaggtc cagggcgact cgctggtcat cctgtcgggc cgcgacgtca cctacacgcc | 6300 |
| cgtggccgcg gggctgttgg agatccaggt gcgcgccttc aacgccctgg gcagtgagaa | 6360 |
| ccgcacgctg gtgctggagg ttcaggacgc cgtccagtat gtggccctgc agagcggccc | 6420 |
| ctgcttcacc aaccgctcgg cgcagtttga ggccgccacc agcccagcc cccgcgtgt | 6480 |
| ggcctaccac tgggactttg gggatgggtc gccagggcag gacacagatg agcccagggc | 6540 |
| cgagcactcc tacctgaggc ctggggacta ccgcgtgcag gtgaacgcct ccaacctggt | 6600 |
| gagcttcttc gtggcgcagg ccacggtgac cgtccaggtg ctggcctgcc gggagccgga | 6660 |
| ggtggacgtg gtcctgcccc tgcaggtgct gatgcggcga tcacagcgca actacttgga | 6720 |
| ggcccacgtt gacctgcgcg actgcgtcac ctaccagact gagtaccgct gggaggtgta | 6780 |
| tcgcaccgcc agctgccagc ggccgggcg cccagcgcgt gtggccctgc ccggcgtgga | 6840 |
| cgtgagccgg cctcggctgg tgctgccgcg gctggcgctg cctgtggggc actactgctt | 6900 |
| tgtgtttgtc gtgtcatttg gggacacgcc actgacacag agcatccagg ccaatgtgac | 6960 |
| ggtggccccc gagcgcctgg tgcccatcat tgagggtggc tcataccgcg tgtggtcaga | 7020 |
| cacacgggac ctggtgctgg atgggagcga gtcctacgac cccaacctgg aggacggcga | 7080 |
| ccagacgccc ctcagtttcc actgggcctg tgtggcttcg acacagaggg aggctggcgg | 7140 |
| gtgtgcgctg aactttgggc cccgcggag cagcacggtc accattccac gggagcggct | 7200 |
| ggcggctggc gtggagtaca ccttcagcct gaccgtgtgg aaggccggcc gcaaggagga | 7260 |
| ggccaccaac cagacggtgc tgatccggag tggccgggtg cccattgtgt ccttggagtg | 7320 |

```
tgtgtcctgc aaggcacagg ccgtgtacga agtgagccgc agctcctacg tgtacttgga    7380
gggccgctgc ctcaattgca gcagcggctc caagcgaggg cggtgggctg cacgtacgtt    7440
cagcaacaag acgctggtgc tggatgagac caccacatcc acgggcagtg caggcatgcg    7500
actggtgctg cggcggggcg tgctgcggga cggcgaggga tacaccttca cgctcacggt    7560
gctgggccgc tctggcgagg aggagggctg cgcctccatc cgcctgtccc caaccgccc    7620
gccgctgggg ggctcttgcc gcctcttccc actgggcgct gtgcacgccc tcaccaccaa    7680
ggtgcacttc gaatgcacgg gctggcatga cgcggaggat gctggcgccc cgctggtgta    7740
cgccctgctg ctgcggcgct gtcgccaggg ccactgcgag gagttctgtg tctacaaggg    7800
cagcctctcc agctacggag ccgtgctgcc cccgggtttc aggccacact tcgaggtggg    7860
cctggccgtg gtggtgcagg accagctggg agccgctgtg gtcgccctca acaggtcttt    7920
ggccatcacc ctcccagagc ccaacggcag cgcaacgggg ctcacagtct ggctgcacgg    7980
gctcaccgct agtgtgctcc cagggctgct gcggcaggcc gatccccagc acgtcatcga    8040
gtactcgttg gccctggtca ccgtgctgaa cgagtacgag cgggccctgg acgtggcggc    8100
agagcccaag cacgagcggc agcaccgagc ccagatacgc aagaacatca cggagactct    8160
ggtgtccctg agggtccaca ctgtggatga catccagcag atcgctgctg cgctggccca    8220
gtgcatgggg cccagcaggg agctcgtatg ccgctcgtgc ctgaagcaga cgctgcacaa    8280
gctggaggcc atgatgctca tcctgcaggc agagaccacc gcgggcaccg tgacgcccac    8340
cgccatcgga gacagcatcc tcaacatcac aggagacctc atccacctgg ccagctcgga    8400
cgtgcgggca ccacagccct cagagctggg agccgagtca ccatctcgga tggtggcgtc    8460
ccaggcctac aacctgacct ctgccctcat gcgcatcctc atgcgctccc gcgtgctcaa    8520
cgaggagccc ctgacgctgg cgggcgagga gatcgtggcc cagggcaagc gctcggaccc    8580
gcggagcctg ctgtgctatg gcggcgcccc agggcctggc tgccacttct ccatccccga    8640
ggctttcagc ggggccctgg ccaacctcag tgacgtggtg cagctcatct ttctggtgga    8700
ctccaatccc tttcccttg gctatatcag caactacacc gtctccacca aggtggcctc    8760
gatggcattc cagacacagg ccggcgccca gatccccatc gagcggctgg cctcagagcg    8820
cgccatcacc gtgaaggtgc ccaacaactc ggactgggct gcccgggggcc accgcagctc    8880
cgccaactcc gccaactccg ttgtggtcca gccccaggcc tccgtcggtg ctgtggtcac    8940
cctggacagc agcaaccctg cggccgggct gcatctgcag ctcaactata cgctgctgga    9000
cggccactac ctgtctgagg aacctgagcc ctacctggca gtctacctac actcggagcc    9060
ccggcccaat gagcacaaact gctcggctag caggaggatc cgcccagagt cactccaggg    9120
tgctgaccac cggccctaca ccttcttcat tccccgggg agcagagacc cagcgggag    9180
ttaccatctg aacctctcca gccacttccg ctggtcggcg ctgcaggtgt ccgtgggcct    9240
gtacacgtcc ctgtgccagt acttcagcga ggaggacatg gtgtggcgga cagaggggct    9300
gctgccctg gaggagacct cgccccgcca ggccgtctgc ctcacccgcc acctcaccgc    9360
cttcggcgcc agcctcttcg tgcccccaag ccatgtccgc tttgtgtttc ctgagccgac    9420
agcggatgta aactacatcg tcatgctgac atgtgctgtg tgcctggtga cctacatggt    9480
catgccgcc atcctgcaca agctggacca gttggatgcc agccggggcc gcgccatccc    9540
tttctgtggg cagcgggcc gcttcaagta cgagatcctc gtcaagacag gctggggccg    9600
gggctcaggt accacggccc acgtgggcat catgctgtat gggggtggac gccggagcgg    9660
```

```
ccaccggcac ctggacggcg acagagcctt ccaccgcaac agcctggaca tcttccggat    9720
cgccaccccg cacagcctgg gtagcgtgtg aagatccga gtgtggcacg acaacaaagg     9780
gctcagccct gcctggttcc tgcagcacgt catcgtcagg gacctgcaga cggcacgcag    9840
cgccttcttc ctggtcaatg actggctttc ggtggagacg gaggccaacg ggggcctggt    9900
ggagaaggag gtgctggccg cgagcgacgc agcccttttg cgcttccggc gcctgctggt    9960
ggctgagctg cagcgtggct tctttgacaa gcacatctgg ctctccatat gggaccggcc    10020
gcctcgtagc cgtttcactc gcatccagag ggccacctgc tgcgttctcc tcatctgcct    10080
cttcctgggc gccaacgccg tgtggtacgg gctgttggc gactctgcct acagcacggg     10140
gcatgtgtcc aggctgagcc cgctgagcgt cgacacagtc gctgttggcc tggtgtccag    10200
cgtggttgtc tatcccgtct acctggccat ccttttctc ttccggatgt cccggagcaa     10260
ggtggctggg agcccgagcc ccacacctgc cgggcagcag gtgctggaca tcgacagctg    10320
cctggactcg tccgtgctgg acagctcctt cctcacgttc tcaggcctcc acgctgaggc    10380
ctttgttgga cagatgaaga gtgacttgtt tctggatgat tctaagagtc tggtgtgctg    10440
gccctccggc gagggaacgc tcagttggcc ggacctgctc agtgaccgt ccattgtggg     10500
tagcaatctg cggcagctgg cacggggcca ggcgggccat gggctgggcc cagaggagga    10560
cggcttctcc ctggccagcc cctactcgcc tgccaaatcc ttctcagcat cagatgaaga    10620
cctgatccag caggtccttg ccgaggggt cagcagccca gcccctaccc aagcacccca     10680
catgaaacg gacctgctca gcagcctgtc cagcactcct ggggagaaga cagagacgct     10740
ggcgctgcag aggctggggg agctggggcc acccagccca ggcctgaact gggaacagcc    10800
ccaggcagcg aggctgtcca ggacaggact ggtggaggt ctgcggaagc gcctgctgcc     10860
ggcctggtgt gcctccctgg cccacgggct cagcctgctc ctggtggctg tggctgtggc    10920
tgtctcaggg tgggtgggtg cgagcttccc cccgggcgtg agtgttgcgt ggctcctgtc    10980
cagcagcgcc agcttcctgg cctcattcct cggctgggag ccactgaagg tcttgctgga    11040
agccctgtac ttctcactgg tggccaagcg gctgcacccg gatgaagatg acaccctggt    11100
agagagcccg gctgtgacgc ctgtgagcgc acgtgtgccc cgcgtacggc caccccacgg    11160
ctttgcactc ttcctggcca aggaagaagc ccgcaaggtc aagaggctac atggcatgct    11220
gcggagcctc ctggtgtaca tgcttttttct gctggtgacc ctgctggcca gctatgggga    11280
tgcctcatgc catgggcacg cctaccgtct gcaaagcgcc atcaagcagg agctgcacag    11340
ccgggccttc ctggccatca cgcggtctga ggagctctgg ccatggatgg cccacgtgct    11400
gctgccctac gtccacggga accagtccag cccagagctg gggccccac ggctgcggca     11460
ggtgcggctg caggaagcac tctacccaga cccctccggc cccagggtcc acgcgtgctc     11520
ggccgcagga ggcttcagca ccagcgatta cgacgttggc tgggagagtc ctcacaatgg    11580
ctcggggacg tgggcctatt cagcgccgga tctgctgggg gcatggtcct ggggctcctg    11640
tgccgtgtat gacagcgggg gctacgtgca ggagctgggc ctgagcctgg aggagagccg    11700
cgaccggctg cgcttcctgc agctgcacaa ctggctggac aacaggagcc gcgctgtgtt    11760
cctggagctc acgcgctaca gcccggccgt ggggctgcac gccgccgtca cgctgcgcct    11820
cgagttcccg gcggccggcc gcgccctggc cgccctcagc gtccgccct ttgcgctgcg     11880
ccgcctcagc gcgggcctct cgctgcctct gctcacctcg gtgtgcctgc tgctgttcgc    11940
cgtgcacttc gccgtggccg aggcccgtac ttggcacagg gaaggcgct ggcgcgtgct     12000
gcggctcgga gcctgggcgc ggtggctgct ggtggcgctg acggcggcca cggcactggt    12060
```

```
acgcctcgcc cagctgggtg ccgctgaccg ccagtggacc cgtttcgtgc gcggccgccc    12120
gcgccgcttc actagcttcg accaggtggc gcagctgagc tccgcagccc gtggcctggc    12180
ggcctcgctg ctcttcctgc ttttggtcaa ggctgcccag cagctacgct tcgtgcgcca    12240
gtggtccgtc tttggcaaga cattatgccg agctctgcca gagctcctgg gggtcacctt    12300
gggcctggtg gtgctcgggg tagcctacgc ccagctggcc atcctgctcg tgtcttcctg    12360
tgtggactcc ctctggagcg tgcccaggc cctgttggtg ctgtgccctg ggactgggct    12420
ctctaccctg tgtcctgccg agtcctgca cctgtcaccc ctgctgtgtg tggggctctg    12480
ggcactgcgg ctgtggggcg ccctacggct gggggctgtt attctccgct ggcgctacca    12540
cgccttgcgt ggagagctgt accggccggc ctgggagccc caggactacg agatggtgga    12600
gttgttcctg cgcaggctgc gcctctggat gggcctcagc aaggtcaagg agttccgcca    12660
caaagtccgc tttgaaggga tggagccgct gccctctcgc tcctccaggg gctccaaggt    12720
atccccggat gtgcccccac ccagcgctgg ctccgatgcc tcgcacccct ccacctcctc    12780
cagccagctg gatgggctga gcgtgagcct gggccggctg gggacaaggt gtgagcctga    12840
gccctcccgc ctccaagccg tgttcgaggc cctgctcacc cagtttgacc gactcaacca    12900
ggccacagag gacgtctacc agctggagca gcagctgcac agcctgcaag gccgcaggag    12960
cagccgggcg cccgccggat cttcccgtgg cccatccccg ggcctgcggc cagcactgcc    13020
cagccgcctt gcccgggcca gtcgggggtgt ggacctggcc actggccca gcaggacacc    13080
ccttcgggcc aagaacaagg tccaccccag cagcacttag tcctccttcc tggcgggggt    13140
gggccgtgga gtcggagtgg acaccgctca gtattacttt ctgccgctgt caaggccgag    13200
ggccaggcag aatggctgca cgtaggttcc ccagagagca ggcagggca tctgtctgtc    13260
tgtgggcttc agcactttaa agaggctgtg tggccaacca ggacccaggg tcccctcccc    13320
agctcccttg ggaaggacac agcagtattg gacggtttct agcctctgag atgctaattt    13380
atttccccga gtcctcaggt acagcgggct gtgcccggcc ccaccccctg gcagatgtc     13440
ccccactgct aaggctgctg gcttcaggga gggttagcct gcaccgccgc caccctgccc    13500
ctaagttatt acctctccag ttcctaccgt actccctgca ccgtctcact gtgtgtctcg    13560
tgtcagtaat ttatatggtg ttaaaatgtg tatattttg tatgtcacta ttttcactag     13620
ggctgagggg cctgcgccca gagctggcct cccccaacac ctgctgcgct tggtaggtgt    13680
ggtggcgtta tggcagcccg gctgctgctt ggatgcgagc ttggccttgg gccggtgctg    13740
ggggcacagc tgtctgccag gcactctcat caccccagag gccttgtcat cctcccttgc    13800
cccaggccag gtagcaagag agcagcgccc aggcctgctg gcatcaggtc tgggcaagta    13860
gcaggactag gcatgtcaga ggaccccagg gtggttagag gaaaagactc ctcctggggg    13920
ctggctccca gggtggagga aggtgactgt gtgtgtgtgt gtgtgcgcgc gcgacgcgcg    13980
agtgtgctgt atggcccagg cagcctcaag gccctcggag ctggctgtgc ctgcttctgt    14040
gtaccacttc tgtgggcatg gccgcttcta gagcctcgac acccccccaa ccccgcacc    14100
aagcagacaa agtcaataaa agagctgtct gactgc                              14136
```

<210> SEQ ID NO 2
<211> LENGTH: 6749
<212> TYPE: DNA
<213> ORGANISM: Homo sapiens
<220> FEATURE:
<221> NAME/KEY: misc_feature
<222> LOCATION: (1)..(6749)

<223> OTHER INFORMATION: "n" at position 719, 1277, 1278, 1279, 1280, 1288, 1289, 1638, 1967, 2248, 2251, 2254, 2283, 2585, 2586, 2625, 2932, 2949, 2972, 2978, 3406, is any of A, T, G, and C.
<223> OTHER INFORMATION: "n" at position 3419, 3604, 3675, 3849, 4132, 4337, 4367, 4368, 4369, 4396, 4404, 5700, 5701, 5702, 6611, 6628, 6637, 6700, 6733 is any of A, T, G, and C.

<400> SEQUENCE: 2

| | | | | | |
|---|---|---|---|---|---|
| ggctcctgag | gcgcacagcg | ccgagcgcgg | cgccgcgcac | ccgcgcgccg | gacgccagtg | 60 |
| accgcgatgg | tgaactccag | tcgcgtgcag | cctcagcagc | ccggggacgc | caagcggccg | 120 |
| cccgcgcccc | gcgcgccgga | cccgggccgg | ctgatggctg | gctgcgcggc | cgtgggcgcc | 180 |
| agcctcgccg | ccccgggccg | cctctgcgag | cagcggggcc | tggagatcga | gatgcagcgc | 240 |
| atccggcagg | cggccgcgcg | ggaccccccg | gccggagccg | cggcctcccc | ttctcctccg | 300 |
| ctctcgtcgt | gctcccggca | ggcgtggagc | cgcgataacc | ccggcttcga | ggccgaggag | 360 |
| gaggaggagg | aggtggaagg | ggaagaaggc | ggaatggtgg | tggagatgga | cgtagagtgg | 420 |
| cgcccgggca | gccggaggtc | ggccgcctcc | tcggccgtga | gctccgtggg | cgcgcggagc | 480 |
| cgggggcttg | ggggctacca | cggcgcgggc | cacccgagcg | ggaggcggcg | ccggcgagag | 540 |
| gaccagggcc | cgccgtgccc | cagcccagtc | ggcggcgggg | accgctgca | tcgccacctc | 600 |
| cccctggaag | ggcagccgcc | ccgagtggcc | tgggcggaga | ggctggttcg | cgggctgcga | 660 |
| ggtgtaagag | cgcgcgaccc | gcagcggcag | atgcacgaac | cagaacggcc | ggcgccggng | 720 |
| gcttcttaaa | taaatgata | tcttttcttt | tcttcattat | tattttaaag | gtctctgggg | 780 |
| aacaagactc | atggaggaaa | gcagcactaa | ccgagagaaa | taccttaaaa | gtgttttacg | 840 |
| ggaactggtc | acatacctcc | tttttctcat | agtcttgtgc | atctgtaagt | agaatatttc | 900 |
| cttgcactaa | tgggaaagtt | ttgaaacgat | gtgaatttgt | ccaaaatgtt | tatccacagg | 960 |
| aacaatccct | ttgtgaaggc | tgctggtatg | tggatgtgtg | ccggttccct | tggggcgttc | 1020 |
| atttggatct | ttctgtgttc | cagtgaccta | cggcatgatg | agctccaatg | tgtactacta | 1080 |
| cacccggatg | atgtcacagc | tcttcctaga | caccccgtg | tccaaaacgg | agaaaactaa | 1140 |
| ctttaaaact | ctgtcttcca | tggaagactt | ctggaaggta | tttggaaata | actttgaaag | 1200 |
| tacctctcta | tcacaagcca | atgcttggtt | atgcaacgat | gcaggcaggg | caaagcagcg | 1260 |
| gcatgagctt | gaacttnnnn | agatgttnnc | tttcttttag | ttcacagaag | gctccttatt | 1320 |
| ggatgggctg | tactggaaga | tgcagcccag | caaccagact | gaagctgaca | accgaagttt | 1380 |
| catcttctat | gagaacctgc | tgttaggggt | tccacgaata | cggcaactcc | gagtcagaaa | 1440 |
| tggatcctgc | tctatccccc | aggacttgag | agatgaaatt | aaagagtgct | atgatgtcta | 1500 |
| ctctgtcagt | agtgaagata | gggctcccctt | tgggccccga | aatggaaccg | cgtaagtgtc | 1560 |
| tgtgactcat | tggcactcgg | tgatattcat | ccttgtaatt | gcctcaagtg | ttccactgat | 1620 |
| tgtaactgtt | tgtttttngg | ttttgttttt | aatcagttgg | atctacacaa | gtgaaaaaga | 1680 |
| cttgaatggt | agtagccact | ggggaatcat | tgcaacttat | agtggagctg | ctattatct | 1740 |
| ggatttgtca | agaacaagag | aggaaacagc | tgcacaagtt | gctagcctca | agaaaaatgt | 1800 |
| ctggctggac | cgaggaacca | gggcaacttt | tattgacttc | tcagtgtaca | acgccaacat | 1860 |
| taacctgttc | tgtgtggtca | ggtgtgtgac | tgaggacatg | catccctcct | atttctgtgt | 1920 |
| ggttgtacat | acatcctatt | ctagggttac | ccagaaaaac | cttttntgc | aggttgttat | 1980 |
| tgttttaatt | gttcttatt | acatgcaggt | tattggttga | attccagca | acaggtggtg | 2040 |
| tgattccatc | ttggcaattt | cagcctttaa | agctgatccg | atatgtcaca | acttttgatt | 2100 |

-continued

```
tcttcctggc agcctgtgag attatctttt gtttctttat cttttactat gtggtggaag    2160
agatattgga aattcgcatt cacaaactac actatttcag gagtttctgg aattgtctgg    2220
atgttgtgat cgttgtggta ggtccganca ncancaccaa atttcctatt ctattctaca    2280
agnatgttaa caattaatac attggtgaag aaaaatatac tagtcatatt aaggtaagtt    2340
tcatatttct aaaacactgt aataaaatat aaatattttg cttttcagct gtcagtggta    2400
gctataggaa ttaacatata cagaacatca aatgtggagg tgctactaca gtttctggaa    2460
gatcaaaata cttccccaa ctttgagcat ctggcatatt ggcagataca gttcaacaat    2520
atagctgctg tcacagtatt ttttgtctgg attaaggtaa tttataaatt tcatgttcta    2580
cattnnaaat aatattttct ttaaaaaaaa tgagttccac aaaancatgc gaaacaatgt    2640
tttattatac acagtcacac catttggttt atccattcat ctattgatgt cttctctctc    2700
ttacagctct tcaaattcat caattttaac aggaccatga gccagctctc gacaaccatg    2760
tctcgatgtg ccaagacct gtttggcttt gctattatgt tcttcattat tttcctagcg    2820
tatgctcagt tggcatacct tgtctttggc actcaggtcg atgacttcag tactttccaa    2880
gagtgtatgt aagtatatat gaaattaaga agaaaaattt agtcagagta gncactgttg    2940
cgtggacant ctttggtttt gtattgtggt gntttgtntt attttatag cttcactcaa    3000 ttccgtatca ttttgggcga tatcaacttt gcagagattg aggaagctaa tcgagttttg    3060
ggaccaattt atttcactac atttgtgttc tttatgttct tcattctttt ggtatgtaca    3120
tttatattta tagtggaggt tcaatttaaa cttcgtaaat ccttgtcttc tcttttttga    3180
ttgataattc caaattatgt ttcttccttt aattttttgcc ctcctttcat ttacaaacag    3240 aatatgttttt tggctatcat caatgatact tactctgaag tgaaatctga cttggcacag    3300
cagaaagctg aaatggaact ctcagatctt atcagaaagg taggaaaaac cttaattctc    3360
aaaaattctt ctgtttctga cataaaatga gcattgtttc acccanattt tagaatacnc    3420
taaaccaagt ctttttattt ttctctctct gatagggcta ccataaagct ttggtcaaac    3480
taaaactgaa aaaaatacc gtggatgaca tttcagagag tctgcggcaa ggaggaggca    3540
agttaaactt tgacgaactt cgacaagatc tcaaagggtg agaatcatgc ttcctgaggt    3600
tctnaaaaat tcctgcttct aaagataaat tcctggtgat aagagtatt ctagcccaag    3660 ggctcatggg aacanaggat gaatgttatc tgtatcctct ctctaatttc aggaagggcc    3720
atactgatgc agagattgag gcaatattca caaagtacga ccaagatgga gaccaagaac    3780
tgaccgaaca tgaacatcag cagatgagag acgacttgga gaaagagagg gtgggtctgg    3840
tttaggagna accggatttg atttggtacc tacaacacca cacttctgtg gggtctcagt    3900
gttctgctcc tcactcagtg accccttgtt cttcaggagg acctggatt ggatcacagt    3960 tcttaccac gtcccatgag cagccgaagt ttccctcgaa gcctggatga ctctgaggag    4020
gatgacgatg aagatagcgg acatagctcc agaaggaggg gaagcatttc tagtggcgtt    4080
tcttacgaag agtttcaagt gtaagtataa aggaattggc agaatttgcg tngacaattt    4140
gtccctctgt actgtgtttt ccttgcagcc tggtgagacg agtggaccgg atggagcatt    4200
ccatcggcag catagtgtcc aagattgacg ccgtgatcgt gaagctagag attatggagc    4260
gagccaaact gaagaggagg gaggtgctgg gaaggctgtt ggatgggtg gccgaggtca    4320 gtagtcatga gctgaanaca ccgctgctga gcatggtgtt attaatnnna atatatgttg    4380
ctgacagttg tatttnaagt attnactgac ccccaacacc agtttctttt tccctttta    4440 ggatgaaagg ctgggtcgtg acagtgaaat ccataggaa cagatggaac ggctagtacg    4500
```

```
tgaagagttg gaacgctggg aatccgatga tgcagcttcc cagatcagtc atggtttagg    4560
cacgccagtg ggactaaatg gtcaacctcg ccccagaagc tcccgcccat cttcctccca    4620
atctacagaa ggcatggaag gtgcaggtgg aaatgggagt tctaatgtcc acgtatgata    4680
tgtgtgtttc agtatgtgtg tttctaataa gtgaggaagt ggctgtcctg aattgctgta    4740
acaagcacac tatttatatg ccctgaccac cataggatgc tagtctttgt gaccgattgc    4800
taatcttctg cactttaatt tattttatat aaactttacc catggttcaa agatttcttt    4860
ttcttttcct catataagaa atctaggtgt aaatattgag tacagaaaaa aaatcttcat    4920
gatgtgtatt gagcggtacg cccagttgcc accatgactg agtcttctca gttgacaatg    4980
aagtagcctt taaagctag aaaactgtca aagggcttct gagtttcatt tccagtcaca    5040
aaaatcagta ttgttatttt tttccaagag tgtgaaggaa atggggcaa ttcctttcca    5100 ctctggcata gttcatgagc ttaatacata gctttctttt aagaaaggag cctttttttt    5160
caactagctt cctggggtaa acttttctaa aagataaat gggaaggaac tccaaactat    5220
gatagaatct gtgtgaatgg ttaagatgaa tgttaaatac tatgcttttt tgtaagttga    5280
tcgtatctga tgtctgtggg actaactgta tcacttaatt tttaccttat tttggctcta    5340
atttgaataa gctgagtaaa accaccaaag atcagttata ggataaaatg gcatctctaa    5400
ccataacaca ggagaattgg aaggagccct aagttgtcac tcagtttaat ttcttttaat    5460
ggttagttta gcctaaagat ttatctgcat attcttttc ccatgtggct ctactcattt    5520
gcaactgaat ttaatgttat aactcatcta gtgagaccaa cttactaaat ttttagtatg    5580
cactgaaagt ttttatccaa caattatgtt cattttaagc aaaatttaa gaaagttttg    5640 aaattcataa agcatttggt tttaaactat tttaagaata tagtactcgg tcaggtatgn    5700
nncacgcctg taatcccagc actttgggag gccgaaacag gcgaatcact tgagcccagg    5760
agttcaagac caacatgggc aatgtggcga aactccatct ctacaaaaaa tgcaaaaata    5820
aaaaatatag tactcaagta ttcttgatcc tgtgtttcaa aactagaatt tgtaatgcaa    5880
atggagctca gtctaataaa aaagaggttt tggtattaaa agttcataca ttagacagta    5940
tcagccaaaa tttgagttag caacactgtt ttctttacga gagggtctca cccaaattta    6000
tggggagaaa tctatttctc aaaaaaaaaa aatcttcttt tacagaaatg ttgagtaagg    6060
tgacattttg agcgctaata agcaaaagag catgcagtgc tgttgaataa ccctcacttg    6120
gagaaccaag agaatcctgt cgtttaatgc tatattttaa tttcacaagt tgttcattta    6180
actggtagaa tgtcagtcca atctccaatg agaacatgag caaatagacc tttccaggtt    6240
gaaagtgaaa catactgggt ttctgtaagt ttttcctcat ggcttcatct ctatctttac    6300
tttctcttga atatgctaca caaagttctt tattactaca tactaaagtt tgcattccag    6360
ggatattgac tgtacatatt tatgtatatg taccatgttg ttacatgtaa acaaacttca    6420
atttgaagtg cagctattat gtggtatcca tgtgtatcga ccatgtgcca tatatcaatt    6480
atggtcacta gaaagtctct ttatgatact ttttattgta ctgttttca tttcacttgc    6540 aaaattttgc agaattcctc ctttctaccc ataaattaca tataattttt cttctttagt    6600
catggagaac nccccccccat catctcancc ctattanctt tcccatgtgt actggtatta    6660
ttaaaaagac atttacatac gcaagttttt cactgacaan caagaatgtt attaatgtgt    6720
aatactgagc acntttactt cttaataaa                                      6749
```

<210> SEQ ID NO 3

-continued

```
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 3
tggctgcaac tgcctcctgg                                                    20

<210> SEQ ID NO 4
<211> LENGTH: 23
<212> TYPE: DNA
<213> ORGANISM: Artificial Sequence
<220> FEATURE:
<221> NAME/KEY: misc_feature
<222> LOCATION: (1)..(23)
<223> OTHER INFORMATION: Synthetic primer

<400> SEQUENCE: 4
aagcagagac agacctgtga gag                                                23

<210> SEQ ID NO 5
<211> LENGTH: 34
<212> TYPE: DNA
<213> ORGANISM: Artificial Sequence
<220> FEATURE:
<221> NAME/KEY: misc_feature
<222> LOCATION: (1)..(34)
<223> OTHER INFORMATION: Synthetic primer

<400> SEQUENCE: 5
gcccccgccg ctctcacagg tctgtctctg cttc                                    34

<210> SEQ ID NO 6
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 6
ggcctgtagc ctacccctgg                                                    20

<210> SEQ ID NO 7
<211> LENGTH: 19
<212> TYPE: DNA
<213> ORGANISM: Artificial Sequence
<220> FEATURE:
<221> NAME/KEY: misc_feature
<222> LOCATION: (1)..(19)
<223> OTHER INFORMATION: Synthetic primer

<400> SEQUENCE: 7
ggacccctct gaagccacc                                                     19

<210> SEQ ID NO 8
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 8
```

```
gggaggtggg agacaagaga c                                    21

<210> SEQ ID NO 9
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 9
aaagccctgc tgtcactgtg g                                    21

<210> SEQ ID NO 10
<211> LENGTH: 23
<212> TYPE: DNA
<213> ORGANISM: Artificial Sequence
<220> FEATURE:
<221> NAME/KEY: misc_feature
<222> LOCATION: (1)..(23)
<223> OTHER INFORMATION: Synthetic primer

<400> SEQUENCE: 10
aactaaagcc cagaagacag acc                                  23

<210> SEQ ID NO 11
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 11
aactgtctgc cccagaacat c                                    21

<210> SEQ ID NO 12
<211> LENGTH: 23
<212> TYPE: DNA
<213> ORGANISM: Artificial Sequence
<220> FEATURE:
<221> NAME/KEY: misc_feature
<222> LOCATION: (1)..(23)
<223> OTHER INFORMATION: Synthetic primer

<400> SEQUENCE: 12
ctaaaggctg ctctctcaac aag                                  23

<210> SEQ ID NO 13
<211> LENGTH: 22
<212> TYPE: DNA
<213> ORGANISM: Artificial Sequence
<220> FEATURE:
<221> NAME/KEY: misc_feature
<222> LOCATION: (1)..(22)
<223> OTHER INFORMATION: Synthetic primer

<400> SEQUENCE: 13
actcctgttg ggttttgatg ag                                   22

<210> SEQ ID NO 14
<211> LENGTH: 23
<212> TYPE: DNA
<213> ORGANISM: Artificial Sequence
<220> FEATURE:
```

```
<221> NAME/KEY: misc_feature
<222> LOCATION: (1)..(23)
<223> OTHER INFORMATION: Synthetic primer

<400> SEQUENCE: 14
gagaactact cccttgtcct tgg                                              23

<210> SEQ ID NO 15
<211> LENGTH: 24
<212> TYPE: DNA
<213> ORGANISM: Artificial Sequence
<220> FEATURE:
<221> NAME/KEY: misc_feature
<222> LOCATION: (1)..(24)
<223> OTHER INFORMATION: Synthetic primer

<400> SEQUENCE: 15
acgccaagga caagggagta gttc                                             24

<210> SEQ ID NO 16
<211> LENGTH: 22
<212> TYPE: DNA
<213> ORGANISM: Artificial Sequence
<220> FEATURE:
<221> NAME/KEY: misc_feature
<222> LOCATION: (1)..(22)
<223> OTHER INFORMATION: Synthetic primer

<400> SEQUENCE: 16
tgggctcctg gctggtgact gc                                               22

<210> SEQ ID NO 17
<211> LENGTH: 40
<212> TYPE: DNA
<213> ORGANISM: Artificial Sequence
<220> FEATURE:
<221> NAME/KEY: misc_feature
<222> LOCATION: (1)..(40)
<223> OTHER INFORMATION: Synthetic primer

<400> SEQUENCE: 17
gcggcccgcc gccccgccg ctactgaccc gcaccctctg                             40

<210> SEQ ID NO 18
<211> LENGTH: 18
<212> TYPE: DNA
<213> ORGANISM: Artificial Sequence
<220> FEATURE:
<221> NAME/KEY: misc_feature
<222> LOCATION: (1)..(18)
<223> OTHER INFORMATION: Synthetic primer

<400> SEQUENCE: 18
gctgcgaggg gtgagacg                                                    18

<210> SEQ ID NO 19
<211> LENGTH: 42
<212> TYPE: DNA
<213> ORGANISM: Artificial Sequence
<220> FEATURE:
<221> NAME/KEY: misc_feature
<222> LOCATION: (1)..(42)
<223> OTHER INFORMATION: Synthetic primer

<400> SEQUENCE: 19
gcggcccgcc gccccgccg cgtccctccc gccctcctga cc                          42
```

```
<210> SEQ ID NO 20
<211> LENGTH: 36
<212> TYPE: DNA
<213> ORGANISM: Artificial Sequence
<220> FEATURE:
<221> NAME/KEY: misc_feature
<222> LOCATION: (1)..(36)
<223> OTHER INFORMATION: Synthetic primer

<400> SEQUENCE: 20
gcccccgccg ctgcggacga gaaatctgtc tgcttg                         36

<210> SEQ ID NO 21
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 21
cagggctgca agcagacaga                                           20

<210> SEQ ID NO 22
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 22
ctgagctaag acgccctccc                                           20

<210> SEQ ID NO 23
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 23
ctgtacgccc tcactggtgt c                                         21

<210> SEQ ID NO 24
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 24
ggcacagggg ctcagtcagt c                                         21

<210> SEQ ID NO 25
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer
```

```
<400> SEQUENCE: 25
ggactgactg agcccctgtg c                                              21

<210> SEQ ID NO 26
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 26
agtcggtcaa actgggtgag                                                20

<210> SEQ ID NO 27
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 27
caaggtgtga gcctgagccc                                                20

<210> SEQ ID NO 28
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 28
cggtgtccac tccgactcca c                                              21

<210> SEQ ID NO 29
<211> LENGTH: 32
<212> TYPE: DNA
<213> ORGANISM: Artificial Sequence
<220> FEATURE:
<221> NAME/KEY: misc_feature
<222> LOCATION: (1)..(32)
<223> OTHER INFORMATION: Synthetic primer

<400> SEQUENCE: 29
ccgcccccgc cgcgcgccgg acgccagtga cc                                  32

<210> SEQ ID NO 30
<211> LENGTH: 30
<212> TYPE: DNA
<213> ORGANISM: Artificial Sequence
<220> FEATURE:
<221> NAME/KEY: misc_feature
<222> LOCATION: (1)..(32)
<223> OTHER INFORMATION: Synthetic primer

<400> SEQUENCE: 30
gcccccgccg ccgcggcctc cccttctcct                                     30

<210> SEQ ID NO 31
<211> LENGTH: 44
<212> TYPE: DNA
<213> ORGANISM: Artificial Sequence
```

-continued

```
<220> FEATURE:
<221> NAME/KEY: misc_feature
<222> LOCATION: (1)..(44)
<223> OTHER INFORMATION: Synthetic primer

<400> SEQUENCE: 31
cggcccgccg ccccgcccg cggccgttct ggttcgtgca tctg            44

<210> SEQ ID NO 32
<211> LENGTH: 34
<212> TYPE: DNA
<213> ORGANISM: Artificial Sequence
<220> FEATURE:
<221> NAME/KEY: misc_feature
<222> LOCATION: (1)..(34)
<223> OTHER INFORMATION: Synthetic primer

<400> SEQUENCE: 32
gcccccgccg aaatgatatc ttttcttttc ttca                      34

<210> SEQ ID NO 33
<211> LENGTH: 30
<212> TYPE: DNA
<213> ORGANISM: Artificial Sequence
<220> FEATURE:
<221> NAME/KEY: misc_feature
<222> LOCATION: (1)..(30)
<223> OTHER INFORMATION: Synthetic primer

<400> SEQUENCE: 33
cccccgcccg aactttccca ttagtgcaag                           30

<210> SEQ ID NO 34
<211> LENGTH: 36
<212> TYPE: DNA
<213> ORGANISM: Artificial Sequence
<220> FEATURE:
<221> NAME/KEY: misc_feature
<222> LOCATION: (1)..(36)
<223> OTHER INFORMATION: Synthetic primer

<400> SEQUENCE: 34
cgccgccccc gcccgtgtga tagagaggta ctttca                    36

<210> SEQ ID NO 35
<211> LENGTH: 39
<212> TYPE: DNA
<213> ORGANISM: Artificial Sequence
<220> FEATURE:
<221> NAME/KEY: misc_feature
<222> LOCATION: (1)..(39)
<223> OTHER INFORMATION: Synthetic primer

<400> SEQUENCE: 35
ccgccgcccc cgccgctttt tcaaagatgt ttcctttgc                 39

<210> SEQ ID NO 36
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 36
tatcaccgag tgccaatgag                                      20
```

<210> SEQ ID NO 37
<211> LENGTH: 35
<212> TYPE: DNA
<213> ORGANISM: Artificial Sequence
<220> FEATURE:
<221> NAME/KEY: misc_feature
<222> LOCATION: (1)..(35)
<223> OTHER INFORMATION: Synthetic primer

<400> SEQUENCE: 37
ccgccgcccc cgccggcctc aagtgttcca ctgat        35

<210> SEQ ID NO 38
<211> LENGTH: 35
<212> TYPE: DNA
<213> ORGANISM: Artificial Sequence
<220> FEATURE:
<221> NAME/KEY: misc_feature
<222> LOCATION: (1)..(35)
<223> OTHER INFORMATION: Synthetic primer

<400> SEQUENCE: 38
cccccgcccg ttgtagaata gaataggaaa tttgg        35

<210> SEQ ID NO 39
<211> LENGTH: 35
<212> TYPE: DNA
<213> ORGANISM: Artificial Sequence
<220> FEATURE:
<221> NAME/KEY: misc_feature
<222> LOCATION: (1)..(35)
<223> OTHER INFORMATION: Synthetic primer

<400> SEQUENCE: 39
gcccccgccg ttggtgaaga aaatatact agtca        35

<210> SEQ ID NO 40
<211> LENGTH: 37
<212> TYPE: DNA
<213> ORGANISM: Artificial Sequence
<220> FEATURE:
<221> NAME/KEY: misc_feature
<222> LOCATION: (1)..(37)
<223> OTHER INFORMATION: Synthetic primer

<400> SEQUENCE: 40
cgccgccccc gcccgtggaa ctcatttttt ttaaaga        37

<210> SEQ ID NO 41
<211> LENGTH: 39
<212> TYPE: DNA
<213> ORGANISM: Artificial Sequence
<220> FEATURE:
<221> NAME/KEY: misc_feature
<222> LOCATION: (1)..(39)
<223> OTHER INFORMATION: Synthetic primer

<400> SEQUENCE: 41 gcggggggcgg cgggccgttt tattatacac agtcacacc        39

<210> SEQ ID NO 42
<211> LENGTH: 32
<212> TYPE: DNA
<213> ORGANISM: Artificial Sequence
<220> FEATURE:
<221> NAME/KEY: misc_feature
<222> LOCATION: (1)..(32)
<223> OTHER INFORMATION: Synthetic primer -continued

```
<400> SEQUENCE: 42
gcccccgccg cttcctttaa tttttgccct cc                        32

<210> SEQ ID NO 43
<211> LENGTH: 39
<212> TYPE: DNA
<213> ORGANISM: Artificial Sequence
<220> FEATURE:
<221> NAME/KEY: misc_feature
<222> LOCATION: (1)..(39)
<223> OTHER INFORMATION: Synthetic primer

<400> SEQUENCE: 43
cgccgccccc gcccggaaac aatgctcatt ttatgtcag                 39

<210> SEQ ID NO 44
<211> LENGTH: 39
<212> TYPE: DNA
<213> ORGANISM: Artificial Sequence
<220> FEATURE:
<221> NAME/KEY: misc_feature
<222> LOCATION: (1)..(39)
<223> OTHER INFORMATION: Synthetic primer

<400> SEQUENCE: 44
ccgccgcccc cgccgaaacc aagtctttta tttttctc                  39

<210> SEQ ID NO 45
<211> LENGTH: 39
<212> TYPE: DNA
<213> ORGANISM: Artificial Sequence
<220> FEATURE:
<221> NAME/KEY: misc_feature
<222> LOCATION: (1)..(39)
<223> OTHER INFORMATION: Synthetic primer

<400> SEQUENCE: 45
ccgccgcccc cgccggatga atgttatctg tatcctctc                 39

<210> SEQ ID NO 46
<211> LENGTH: 37
<212> TYPE: DNA
<213> ORGANISM: Artificial Sequence
<220> FEATURE:
<221> NAME/KEY: misc_feature
<222> LOCATION: (1)..(37)
<223> OTHER INFORMATION: Synthetic primer

<400> SEQUENCE: 46
cgccgccccc gcccggcaaa ttctgccaat tccttta                   37

<210> SEQ ID NO 47
<211> LENGTH: 32
<212> TYPE: DNA
<213> ORGANISM: Artificial Sequence
<220> FEATURE:
<221> NAME/KEY: misc_feature
<222> LOCATION: (1)..(32)
<223> OTHER INFORMATION: Synthetic primer

<400> SEQUENCE: 47
gcccccgccg tttgtccctc tgtactgtgt tt                        32

<210> SEQ ID NO 48
<211> LENGTH: 32
<212> TYPE: DNA
```

-continued

<213> ORGANISM: Artificial Sequence
<220> FEATURE:
<221> NAME/KEY: misc_feature
<222> LOCATION: (1)..(32)
<223> OTHER INFORMATION: Synthetic primer

<400> SEQUENCE: 48
ccgcccccgc cgtgaccccc aacaccagtt tc                                    32

<210> SEQ ID NO 49
<211> LENGTH: 40
<212> TYPE: DNA
<213> ORGANISM: Artificial Sequence
<220> FEATURE:
<221> NAME/KEY: misc_feature
<222> LOCATION: (1)..(40)
<223> OTHER INFORMATION: Synthetic primer

<400> SEQUENCE: 49
cggcccgccg cccccgcccg ggacagccac ttcctcactt                            40

<210> SEQ ID NO 50
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 50
cgtcgctcag cagcaggtcg                                                  20

<210> SEQ ID NO 51
<211> LENGTH: 19
<212> TYPE: DNA
<213> ORGANISM: Artificial Sequence
<220> FEATURE:
<221> NAME/KEY: misc_feature
<222> LOCATION: (1)..(19)
<223> OTHER INFORMATION: Synthetic primer

<400> SEQUENCE: 51
cgtcctgctt cccgtcccg                                                   19

<210> SEQ ID NO 52
<211> LENGTH: 42
<212> TYPE: DNA
<213> ORGANISM: Artificial Sequence
<220> FEATURE:
<221> NAME/KEY: misc_feature
<222> LOCATION: (1)..(42)
<223> OTHER INFORMATION: Synthetic primer

<400> SEQUENCE: 52
gcggcccgcc gccccgccg ttggggatgc tggcaatgtg tg                          42

<210> SEQ ID NO 53
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 53
gggattcggc aaagctgatg                                                  20

<210> SEQ ID NO 54
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 54
ttccatcagc tttgccgaat                                               20

<210> SEQ ID NO 55
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 55
atctggtctc aagcctggaa g                                             21

<210> SEQ ID NO 56
<211> LENGTH: 49
<212> TYPE: DNA
<213> ORGANISM: Artificial Sequence
<220> FEATURE:
<221> NAME/KEY: misc_feature
<222> LOCATION: (1)..(49)
<223> OTHER INFORMATION: Synthetic primer

<400> SEQUENCE: 56
gccccgcgcc cgtcccgccg ccccccgccga gaccctccc accagacct              49

<210> SEQ ID NO 57
<211> LENGTH: 31
<212> TYPE: DNA
<213> ORGANISM: Artificial Sequence
<220> FEATURE:
<221> NAME/KEY: misc_feature
<222> LOCATION: (1)..(31)
<223> OTHER INFORMATION: Synthetic primer

<400> SEQUENCE: 57
cgcccccgcc cgtgagccct gcccagtgtc t                                  31

<210> SEQ ID NO 58
<211> LENGTH: 41
<212> TYPE: DNA
<213> ORGANISM: Artificial Sequence
<220> FEATURE:
<221> NAME/KEY: misc_feature
<222> LOCATION: (1)..(41)
<223> OTHER INFORMATION: Synthetic primer

<400> SEQUENCE: 58
gcggcccgcc gcccccgccg gagccaggag gagcagaacc c                       41

<210> SEQ ID NO 59
<211> LENGTH: 22
<212> TYPE: DNA
<213> ORGANISM: Artificial Sequence
<220> FEATURE:
<221> NAME/KEY: misc_feature
<222> LOCATION: (1)..(22)

<223> OTHER INFORMATION: Synthetic primer

<400> SEQUENCE: 59
cagagggaca ggcaggcaaa gg                                         22

<210> SEQ ID NO 60
<211> LENGTH: 28
<212> TYPE: DNA
<213> ORGANISM: Artificial Sequence
<220> FEATURE:
<221> NAME/KEY: misc_feature
<222> LOCATION: (1)..(28)
<223> OTHER INFORMATION: Synthetic primer

<400> SEQUENCE: 60
gcccccgccg cccagccctc cagtgcct                                   28

<210> SEQ ID NO 61
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 61
atcgctatgt gctgcctggg                                            20

<210> SEQ ID NO 62
<211> LENGTH: 18
<212> TYPE: DNA
<213> ORGANISM: Artificial Sequence
<220> FEATURE:
<221> NAME/KEY: misc_feature
<222> LOCATION: (1)..(18)
<223> OTHER INFORMATION: Synthetic primer

<400> SEQUENCE: 62
ccgaggtgga tgccgctg                                              18

<210> SEQ ID NO 63
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 63 gaagggagt gggcagcaga c                                           21

<210> SEQ ID NO 64
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 64
cactgaccgt tgacaccctc g                                          21

<210> SEQ ID NO 65
<211> LENGTH: 21

```
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 65
tgccccagtg cttcagagat c                                    21

<210> SEQ ID NO 66
<211> LENGTH: 19
<212> TYPE: DNA
<213> ORGANISM: Artificial Sequence
<220> FEATURE:
<221> NAME/KEY: misc_feature
<222> LOCATION: (1)..(19)
<223> OTHER INFORMATION: Synthetic primer

<400> SEQUENCE: 66
ggagtgccct gagccccct                                       19

<210> SEQ ID NO 67
<211> LENGTH: 19
<212> TYPE: DNA
<213> ORGANISM: Artificial Sequence
<220> FEATURE:
<221> NAME/KEY: misc_feature
<222> LOCATION: (1)..(19)
<223> OTHER INFORMATION: Synthetic primer

<400> SEQUENCE: 67
cccctaacca cagccagcg                                       19

<210> SEQ ID NO 68
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 68
tctgttcgtc ctggtgtcct g                                    21

<210> SEQ ID NO 69
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 69
gcaggagggc aggttgtaga a                                    21

<210> SEQ ID NO 70
<211> LENGTH: 40
<212> TYPE: DNA
<213> ORGANISM: Artificial Sequence
<220> FEATURE:
<221> NAME/KEY: misc_feature
<222> LOCATION: (1)..(40)
<223> OTHER INFORMATION: Synthetic primer

<400> SEQUENCE: 70
```
gcggcccgcc gccccgccg ggtaggggga gtctgggctt                    40

<210> SEQ ID NO 71
<211> LENGTH: 17
<212> TYPE: DNA
<213> ORGANISM: Artificial Sequence
<220> FEATURE:
<221> NAME/KEY: misc_feature
<222> LOCATION: (1)..(17)
<223> OTHER INFORMATION: Synthetic primer

<400> SEQUENCE: 71
gaggccaccc cgagtcc                                            17

<210> SEQ ID NO 72
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 72
gttgggcatc tctgacggtg                                         20

<210> SEQ ID NO 73
<211> LENGTH: 35
<212> TYPE: DNA
<213> ORGANISM: Artificial Sequence
<220> FEATURE:
<221> NAME/KEY: misc_feature
<222> LOCATION: (1)..(35)
<223> OTHER INFORMATION: Synthetic primer

<400> SEQUENCE: 73
cgccgccccc gcccgggaag gtggcctgag gagat                        35

<210> SEQ ID NO 74
<211> LENGTH: 37
<212> TYPE: DNA
<213> ORGANISM: Artificial Sequence
<220> FEATURE:
<221> NAME/KEY: misc_feature
<222> LOCATION: (1)..(37)
<223> OTHER INFORMATION: Synthetic primer

<400> SEQUENCE: 74
gcggcccgcc gccccgccg ggggtccacg ggccatg                       37

<210> SEQ ID NO 75
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 75
aagcccagca gcacggtgag                                         20

<210> SEQ ID NO 76
<211> LENGTH: 34
<212> TYPE: DNA
<213> ORGANISM: Artificial Sequence
<220> FEATURE:
<221> NAME/KEY: misc_feature

```
<222> LOCATION: (1)..(34)
<223> OTHER INFORMATION: Synthetic primer

<400> SEQUENCE: 76
ccgccgcccc cgccgctgcc ctgcctgtgc cctg                          34

<210> SEQ ID NO 77
<211> LENGTH: 51
<212> TYPE: DNA
<213> ORGANISM: Artificial Sequence
<220> FEATURE:
<221> NAME/KEY: misc_feature
<222> LOCATION: (1)..(51)
<223> OTHER INFORMATION: Synthetic primer

<400> SEQUENCE: 77
gccccgcgcc cgtcccgccg ccccgcccg ttccaccacc acgtccacca c        51

<210> SEQ ID NO 78
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 78
gtggtggacg tggtggtgga a                                        21

<210> SEQ ID NO 79
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 79
ggctgctgcc ctcactggga a                                        21

<210> SEQ ID NO 80
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 80
taagggcaga gtcctccaca g                                        21

<210> SEQ ID NO 81
<211> LENGTH: 22
<212> TYPE: DNA
<213> ORGANISM: Artificial Sequence
<220> FEATURE:
<221> NAME/KEY: misc_feature
<222> LOCATION: (1)..(22)
<223> OTHER INFORMATION: Synthetic primer

<400> SEQUENCE: 81
ccacccccgc ccacctactg ag                                       22

<210> SEQ ID NO 82
```

```
<211> LENGTH: 40
<212> TYPE: DNA
<213> ORGANISM: Artificial Sequence
<220> FEATURE:
<221> NAME/KEY: misc_feature
<222> LOCATION: (1)..(40)
<223> OTHER INFORMATION: Synthetic primer

<400> SEQUENCE: 82
gcggcccgcc gccccgccg tggagggagg gacgccaatc                              40

<210> SEQ ID NO 83
<211> LENGTH: 19
<212> TYPE: DNA
<213> ORGANISM: Artificial Sequence
<220> FEATURE:
<221> NAME/KEY: misc_feature
<222> LOCATION: (1)..(19)
<223> OTHER INFORMATION: Synthetic primer

<400> SEQUENCE: 83
gaggctgggg ctgggacaa                                                    19

<210> SEQ ID NO 84
<211> LENGTH: 18
<212> TYPE: DNA
<213> ORGANISM: Artificial Sequence
<220> FEATURE:
<221> NAME/KEY: misc_feature
<222> LOCATION: (1)..(18)
<223> OTHER INFORMATION: Synthetic primer

<400> SEQUENCE: 84
cccggttcac tcactgcg                                                     18

<210> SEQ ID NO 85
<211> LENGTH: 30
<212> TYPE: DNA
<213> ORGANISM: Artificial Sequence
<220> FEATURE:
<221> NAME/KEY: misc_feature
<222> LOCATION: (1)..(30)
<223> OTHER INFORMATION: Synthetic primer

<400> SEQUENCE: 85
cccccgcccg ccgtgctcag agcctgaaag                                        30

<210> SEQ ID NO 86
<211> LENGTH: 38
<212> TYPE: DNA
<213> ORGANISM: Artificial Sequence
<220> FEATURE:
<221> NAME/KEY: misc_feature
<222> LOCATION: (1)..(38)
<223> OTHER INFORMATION: Synthetic primer

<400> SEQUENCE: 86 ggcgggggc ttctgccgag cgggtgggga gcaggtgg                                38

<210> SEQ ID NO 87
<211> LENGTH: 36
<212> TYPE: DNA
<213> ORGANISM: Artificial Sequence
<220> FEATURE:
<221> NAME/KEY: misc_feature
<222> LOCATION: (1)..(36)
<223> OTHER INFORMATION: Synthetic primer

<400> SEQUENCE: 87
```

```
cgccgccccc gcccggctct gggtcaggac agggga                          36

<210> SEQ ID NO 88
<211> LENGTH: 18
<212> TYPE: DNA
<213> ORGANISM: Artificial Sequence
<220> FEATURE:
<221> NAME/KEY: misc_feature
<222> LOCATION: (1)..(18)
<223> OTHER INFORMATION: Synthetic primer

<400> SEQUENCE: 88
cgcctggggg tgttctttt                                             18

<210> SEQ ID NO 89
<211> LENGTH: 18
<212> TYPE: DNA
<213> ORGANISM: Artificial Sequence
<220> FEATURE:
<221> NAME/KEY: misc_feature
<222> LOCATION: (1)..(18)
<223> OTHER INFORMATION: Synthetic primer

<400> SEQUENCE: 89
acgtgatgtt gtcgcccg                                              18

<210> SEQ ID NO 90
<211> LENGTH: 32
<212> TYPE: DNA
<213> ORGANISM: Artificial Sequence
<220> FEATURE:
<221> NAME/KEY: misc_feature
<222> LOCATION: (1)..(32)
<223> OTHER INFORMATION: Synthetic primer

<400> SEQUENCE: 90
gcccccgccg gggcgccccc gtggtggtca gc                              32

<210> SEQ ID NO 91
<211> LENGTH: 18
<212> TYPE: DNA
<213> ORGANISM: Artificial Sequence
<220> FEATURE:
<221> NAME/KEY: misc_feature
<222> LOCATION: (1)..(18)
<223> OTHER INFORMATION: Synthetic primer

<400> SEQUENCE: 91
caggctgcgt ggggatgc                                              18

<210> SEQ ID NO 92
<211> LENGTH: 18
<212> TYPE: DNA
<213> ORGANISM: Artificial Sequence
<220> FEATURE:
<221> NAME/KEY: misc_feature
<222> LOCATION: (1)..(18)
<223> OTHER INFORMATION: Synthetic primer

<400> SEQUENCE: 92
ctggaggtgc tgcgcgtt                                              18

<210> SEQ ID NO 93
<211> LENGTH: 30
<212> TYPE: DNA
<213> ORGANISM: Artificial Sequence
<220> FEATURE:
```

-continued

```
<221> NAME/KEY: misc_feature
<222> LOCATION: (1)..(30)
<223> OTHER INFORMATION: Synthetic primer

<400> SEQUENCE: 93
cgcccccgcc cgctggctcc acgcagatgc                                    30

<210> SEQ ID NO 94
<211> LENGTH: 18
<212> TYPE: DNA
<213> ORGANISM: Artificial Sequence
<220> FEATURE:
<221> NAME/KEY: misc_feature
<222> LOCATION: (1)..(18)
<223> OTHER INFORMATION: Synthetic primer

<400> SEQUENCE: 94
cgtgaacagg gcgcatta                                                 18

<210> SEQ ID NO 95
<211> LENGTH: 31
<212> TYPE: DNA
<213> ORGANISM: Artificial Sequence
<220> FEATURE:
<221> NAME/KEY: misc_feature
<222> LOCATION: (1)..(31)
<223> OTHER INFORMATION: Synthetic primer

<400> SEQUENCE: 95
cccccgcccg gcagcagaga tgttgttgga c                                  31

<210> SEQ ID NO 96
<211> LENGTH: 36
<212> TYPE: DNA
<213> ORGANISM: Artificial Sequence
<220> FEATURE:
<221> NAME/KEY: misc_feature
<222> LOCATION: (1)..(36)
<223> OTHER INFORMATION: Synthetic primer

<400> SEQUENCE: 96
ccgccgcccc cgccgccagg ctcctatctt gtgaca                             36

<210> SEQ ID NO 97
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 97
tgaagtcacc tgtgctgttg t                                             21

<210> SEQ ID NO 98
<211> LENGTH: 19
<212> TYPE: DNA
<213> ORGANISM: Artificial Sequence
<220> FEATURE:
<221> NAME/KEY: misc_feature
<222> LOCATION: (1)..(19)
<223> OTHER INFORMATION: Synthetic primer

<400> SEQUENCE: 98
ctacctgtgg gatctgggg                                                19
```

<210> SEQ ID NO 99
<211> LENGTH: 18
<212> TYPE: DNA
<213> ORGANISM: Artificial Sequence
<220> FEATURE:
<221> NAME/KEY: misc_feature
<222> LOCATION: (1)..(18)
<223> OTHER INFORMATION: Synthetic primer

<400> SEQUENCE: 99
tgctgaagct cacgctcc                                             18

<210> SEQ ID NO 100
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 100
gggctcgtcg tcaatgcaag                                           20

<210> SEQ ID NO 101
<211> LENGTH: 40
<212> TYPE: DNA
<213> ORGANISM: Artificial Sequence
<220> FEATURE:
<221> NAME/KEY: misc_feature
<222> LOCATION: (1)..(40)
<223> OTHER INFORMATION: Synthetic primer

<400> SEQUENCE: 101
cgccgccccc gcccgccgcc caccacctgc agcccctcta                     40

<210> SEQ ID NO 102
<211> LENGTH: 40
<212> TYPE: DNA
<213> ORGANISM: Artificial Sequence
<220> FEATURE:
<221> NAME/KEY: misc_feature
<222> LOCATION: (1)..(40)
<223> OTHER INFORMATION: Synthetic primer

<400> SEQUENCE: 102
gcggcccgcc gcccccgccg ccgcccagga cagcatcttc                     40

<210> SEQ ID NO 103
<211> LENGTH: 18
<212> TYPE: DNA
<213> ORGANISM: Artificial Sequence
<220> FEATURE:
<221> NAME/KEY: misc_feature
<222> LOCATION: (1)..(18)
<223> OTHER INFORMATION: Synthetic primer

<400> SEQUENCE: 103
cgctgcccag catgttgg                                             18

<210> SEQ ID NO 104
<211> LENGTH: 24
<212> TYPE: DNA
<213> ORGANISM: Artificial Sequence
<220> FEATURE:
<221> NAME/KEY: misc_feature
<222> LOCATION: (1)..(24)
<223> OTHER INFORMATION: Synthetic primer

<400> SEQUENCE: 104
ggccggcagc ggcaaaggct tctc                                      24

<210> SEQ ID NO 105
<211> LENGTH: 19
<212> TYPE: DNA
<213> ORGANISM: Artificial Sequence
<220> FEATURE:
<221> NAME/KEY: misc_feature
<222> LOCATION: (1)..(19)
<223> OTHER INFORMATION: Synthetic primer

<400> SEQUENCE: 105
gcccagcacc agctcacat                                            19

<210> SEQ ID NO 106
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 106
cgagccattt accacccata g                                         21

<210> SEQ ID NO 107
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 107
ggcagccagc aggatctgaa                                           20

<210> SEQ ID NO 108
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 108
ctgtgggcca gcagcaaggt g                                         21

<210> SEQ ID NO 109
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 109
cctgaacctc cagcaccagc g                                         21

<210> SEQ ID NO 110
<211> LENGTH: 21
<212> TYPE: DNA
<213> ORGANISM: Artificial Sequence

```
<220> FEATURE:
<221> NAME/KEY: misc_feature
<222> LOCATION: (1)..(21)
<223> OTHER INFORMATION: Synthetic primer

<400> SEQUENCE: 110
aggtccaggg cgactcgctg g                                              21

<210> SEQ ID NO 111
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 111
cagggccaca cgcgctgggc g                                              21

<210> SEQ ID NO 112
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 112
ttggaggccc acgttgacct g                                              21

<210> SEQ ID NO 113
<211> LENGTH: 31
<212> TYPE: DNA
<213> ORGANISM: Artificial Sequence
<220> FEATURE:
<221> NAME/KEY: misc_feature
<222> LOCATION: (1)..(31)
<223> OTHER INFORMATION: Synthetic primer

<400> SEQUENCE: 113
cccccgcccg catgggtgtg gacgggtgag g                                   31

<210> SEQ ID NO 114
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 114
taaaactgga tggggctctc                                                20

<210> SEQ ID NO 115
<211> LENGTH: 18
<212> TYPE: DNA
<213> ORGANISM: Artificial Sequence
<220> FEATURE:
<221> NAME/KEY: misc_feature
<222> LOCATION: (1)..(18)
<223> OTHER INFORMATION: Synthetic primer

<400> SEQUENCE: 115
ggcctccacc agcactaa                                                  18
```

```
<210> SEQ ID NO 116
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 116
gggtccccca gtccttccag                                              20

<210> SEQ ID NO 117
<211> LENGTH: 17
<212> TYPE: DNA
<213> ORGANISM: Artificial Sequence
<220> FEATURE:
<221> NAME/KEY: misc_feature
<222> LOCATION: (1)..(17)
<223> OTHER INFORMATION: Synthetic primer

<400> SEQUENCE: 117
tccccagccc gcccaca                                                 17

<210> SEQ ID NO 118
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 118
gcccccccac cacccccttct                                             20

<210> SEQ ID NO 119
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 119
tcccgctgct cccccacgc a                                             21

<210> SEQ ID NO 120
<211> LENGTH: 18
<212> TYPE: DNA
<213> ORGANISM: Artificial Sequence
<220> FEATURE:
<221> NAME/KEY: misc_feature
<222> LOCATION: (1)..(18)
<223> OTHER INFORMATION: Synthetic primer

<400> SEQUENCE: 120
gatgccgtgg ggaccgtc                                                18

<210> SEQ ID NO 121
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer
```

```
<400> SEQUENCE: 121
gtgagcaggt ggcagtctcg                                              20

<210> SEQ ID NO 122
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 122
ccaccccctc tgctcgtagg t                                            21

<210> SEQ ID NO 123
<211> LENGTH: 19
<212> TYPE: DNA
<213> ORGANISM: Artificial Sequence
<220> FEATURE:
<221> NAME/KEY: misc_feature
<222> LOCATION: (1)..(19)
<223> OTHER INFORMATION: Synthetic primer

<400> SEQUENCE: 123
ggtcccaagc acgcatgca                                               19

<210> SEQ ID NO 124
<211> LENGTH: 22
<212> TYPE: DNA
<213> ORGANISM: Artificial Sequence
<220> FEATURE:
<221> NAME/KEY: misc_feature
<222> LOCATION: (1)..(22)
<223> OTHER INFORMATION: Synthetic primer

<400> SEQUENCE: 124
tgccggcctc ctgcgctgct ga                                           22

<210> SEQ ID NO 125
<211> LENGTH: 29
<212> TYPE: DNA
<213> ORGANISM: Artificial Sequence
<220> FEATURE:
<221> NAME/KEY: misc_feature
<222> LOCATION: (1)..(29)
<223> OTHER INFORMATION: Synthetic primer

<400> SEQUENCE: 125
gcgggcaggg tgagcaggtg gggccatcc                                    29

<210> SEQ ID NO 126
<211> LENGTH: 26
<212> TYPE: DNA
<213> ORGANISM: Artificial Sequence
<220> FEATURE:
<221> NAME/KEY: misc_feature
<222> LOCATION: (1)..(26)
<223> OTHER INFORMATION: Synthetic primer

<400> SEQUENCE: 126
gaggctgtgg gggtccagtc aagtgg                                       26

<210> SEQ ID NO 127
<211> LENGTH: 25
<212> TYPE: DNA
```

```
<213> ORGANISM: Artificial Sequence
<220> FEATURE:
<221> NAME/KEY: misc_feature
<222> LOCATION: (1)..(25)
<223> OTHER INFORMATION: Synthetic primer

<400> SEQUENCE: 127
agggaggcag aggaaagggc cgaac                                              25

<210> SEQ ID NO 128
<211> LENGTH: 29
<212> TYPE: DNA
<213> ORGANISM: Artificial Sequence
<220> FEATURE:
<221> NAME/KEY: misc_feature
<222> LOCATION: (1)..(29)
<223> OTHER INFORMATION: Synthetic primer

<400> SEQUENCE: 128
cgtcccgcct gcactgacct cacgcatgt                                          29

<210> SEQ ID NO 129
<211> LENGTH: 41
<212> TYPE: DNA
<213> ORGANISM: Artificial Sequence
<220> FEATURE:
<221> NAME/KEY: misc_feature
<222> LOCATION: (1)..(41)
<223> OTHER INFORMATION: Synthetic primer

<400> SEQUENCE: 129
cggcccgccg cccccgcccg gccaaaggga aagggattgg a                            41

<210> SEQ ID NO 130
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 130
ccgcggagcc tgctgtgcta t                                                  21

<210> SEQ ID NO 131
<211> LENGTH: 39
<212> TYPE: DNA
<213> ORGANISM: Artificial Sequence
<220> FEATURE:
<221> NAME/KEY: misc_feature
<222> LOCATION: (1)..(39)
<223> OTHER INFORMATION: Synthetic primer

<400> SEQUENCE: 131
ccgccgcccc cgcccgcttg gtggagacgg tgtagttgc                               39

<210> SEQ ID NO 132
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 132
tccaatccct ttccctttgg c                                                  21
```

<210> SEQ ID NO 133
<211> LENGTH: 22
<212> TYPE: DNA
<213> ORGANISM: Artificial Sequence
<220> FEATURE:
<221> NAME/KEY: misc_feature
<222> LOCATION: (1)..(22)
<223> OTHER INFORMATION: Synthetic primer

<400> SEQUENCE: 133
cagcagccca tgaaacagaa ag         22

<210> SEQ ID NO 134
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 134
tatgctttca ggcccgtggc a          21

<210> SEQ ID NO 135
<211> LENGTH: 23
<212> TYPE: DNA
<213> ORGANISM: Artificial Sequence
<220> FEATURE:
<221> NAME/KEY: misc_feature
<222> LOCATION: (1)..(23)
<223> OTHER INFORMATION: Synthetic primer

<400> SEQUENCE: 135
agagcccata cccggtccag tcc        23

<210> SEQ ID NO 136
<211> LENGTH: 23
<212> TYPE: DNA
<213> ORGANISM: Artificial Sequence
<220> FEATURE:
<221> NAME/KEY: misc_feature
<222> LOCATION: (1)..(23)
<223> OTHER INFORMATION: Synthetic primer

<400> SEQUENCE: 136
ggactggacc gggtatgggc tct        23

<210> SEQ ID NO 137
<211> LENGTH: 31
<212> TYPE: DNA
<213> ORGANISM: Artificial Sequence
<220> FEATURE:
<221> NAME/KEY: misc_feature
<222> LOCATION: (1)..(31)
<223> OTHER INFORMATION: Synthetic primer

<400> SEQUENCE: 137
cccccgcccg cacccaggcc ctcctcgact c    31

<210> SEQ ID NO 138
<211> LENGTH: 30
<212> TYPE: DNA
<213> ORGANISM: Artificial Sequence
<220> FEATURE:
<221> NAME/KEY: misc_feature
<222> LOCATION: (1)..(30)

-continued

<223> OTHER INFORMATION: Synthetic primer

<400> SEQUENCE: 138
cccccgccgc tgggtgggct cggctctatc          30

<210> SEQ ID NO 139
<211> LENGTH: 23
<212> TYPE: DNA
<213> ORGANISM: Artificial Sequence
<220> FEATURE:
<221> NAME/KEY: misc_feature
<222> LOCATION: (1)..(23)
<223> OTHER INFORMATION: Synthetic primer

<400> SEQUENCE: 139
tggtagcgat gctcacgtca ctt          23

<210> SEQ ID NO 140
<211> LENGTH: 23
<212> TYPE: DNA
<213> ORGANISM: Artificial Sequence
<220> FEATURE:
<221> NAME/KEY: misc_feature
<222> LOCATION: (1)..(23)
<223> OTHER INFORMATION: Synthetic primer

<400> SEQUENCE: 140
caggccaaag ctgagatgac ttg          23

<210> SEQ ID NO 141
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 141
agaggcgcag gagggaggtc          20

<210> SEQ ID NO 142
<211> LENGTH: 18
<212> TYPE: DNA
<213> ORGANISM: Artificial Sequence
<220> FEATURE:
<221> NAME/KEY: misc_feature
<222> LOCATION: (1)..(18)
<223> OTHER INFORMATION: Synthetic primer

<400> SEQUENCE: 142
ccctctgccc ccgcattg          18

<210> SEQ ID NO 143
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 143
aagcgcaaaa gggctgcgtc g          21

<210> SEQ ID NO 144
<211> LENGTH: 22

```
<212> TYPE: DNA
<213> ORGANISM: Artificial Sequence
<220> FEATURE:
<221> NAME/KEY: misc_feature
<222> LOCATION: (1)..(22)
<223> OTHER INFORMATION: Synthetic primer

<400> SEQUENCE: 144
ggccctccct gccttctagg cg                                              22

<210> SEQ ID NO 145
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 145
ccgtgctgtg tggaggagag                                                 20

<210> SEQ ID NO 146
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 146
cctcttcctg cccagccctt c                                               21

<210> SEQ ID NO 147
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 147
cttcccgagc agcctttggt g                                               21

<210> SEQ ID NO 148
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 148
ctgagctgcc gcccgctgac                                                 20

<210> SEQ ID NO 149
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 149
```

-continued aggaccccca gcccagccca                    20

<210> SEQ ID NO 150
<211> LENGTH: 18
<212> TYPE: DNA
<213> ORGANISM: Artificial Sequence
<220> FEATURE:
<221> NAME/KEY: misc_feature
<222> LOCATION: (1)..(18)
<223> OTHER INFORMATION: Synthetic primer

<400> SEQUENCE: 150
cttggcgcag cttggact                      18

<210> SEQ ID NO 151
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 151
acacccagca aggacacgca                    20

<210> SEQ ID NO 152
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 152
tgtgacacat cccctggtac                    20

<210> SEQ ID NO 153
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 153
gcaagggtga gcttcagagc                    20

<210> SEQ ID NO 154
<211> LENGTH: 51
<212> TYPE: DNA
<213> ORGANISM: Artificial Sequence
<220> FEATURE:
<221> NAME/KEY: misc_feature
<222> LOCATION: (1)..(51)
<223> OTHER INFORMATION: Synthetic primer

<400> SEQUENCE: 154
gccccgcgcc cgtcccgccg cccccgcccg accctatgcc tcctgtacct c         51

<210> SEQ ID NO 155
<211> LENGTH: 18
<212> TYPE: DNA
<213> ORGANISM: Artificial Sequence
<220> FEATURE:
<221> NAME/KEY: misc_feature

```
<222> LOCATION: (1)..(18)
<223> OTHER INFORMATION: Synthetic primer

<400> SEQUENCE: 155
cccctcctct ggcaatcc                                                        18

<210> SEQ ID NO 156
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 156
cctgccggga gcacgacgag                                                      20

<210> SEQ ID NO 157
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 157
ctgggctggg gcacggcggg                                                      20

<210> SEQ ID NO 158
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 158
gggggctacc acggcgcggg c                                                    21

<210> SEQ ID NO 159
<211> LENGTH: 20
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 159
ttggggcgtt catttggatc                                                      20

<210> SEQ ID NO 160
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 160
accacacaga aataggaggg                                                      20

<210> SEQ ID NO 161
```

```
<211> LENGTH: 24
<212> TYPE: DNA
<213> ORGANISM: Artificial Sequence
<220> FEATURE:
<221> NAME/KEY: misc_feature
<222> LOCATION: (1)..(24)
<223> OTHER INFORMATION: Synthetic primer

<400> SEQUENCE: 161
ttgttattgt tttaattgtt ctta                                          24

<210> SEQ ID NO 162
<211> LENGTH: 25
<212> TYPE: DNA
<213> ORGANISM: Artificial Sequence
<220> FEATURE:
<221> NAME/KEY: misc_feature
<222> LOCATION: (1)..(25)
<223> OTHER INFORMATION: Synthetic primer

<400> SEQUENCE: 162
ctactctgac taaattttc ttctt                                          25

<210> SEQ ID NO 163
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 163
tttggttttg tattgtggtg                                               20

<210> SEQ ID NO 164
<211> LENGTH: 23
<212> TYPE: DNA
<213> ORGANISM: Artificial Sequence
<220> FEATURE:
<221> NAME/KEY: misc_feature
<222> LOCATION: (1)..(23)
<223> OTHER INFORMATION: Synthetic primer

<400> SEQUENCE: 164
aaggatttac gaagtttaaa ttg                                           23

<210> SEQ ID NO 165
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 165
agaacctcag gaagcatgat t                                             21

<210> SEQ ID NO 166
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 166
```

-continued

```
taggtaccaa atcaaatccg                                          20

<210> SEQ ID NO 167
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 167
gtctcagtgt tctgctcctc                                          20

<210> SEQ ID NO 168
<211> LENGTH: 22
<212> TYPE: DNA
<213> ORGANISM: Artificial Sequence Sequence
<220> FEATURE:
<221> NAME/KEY: misc_feature
<222> LOCATION: (1)..(22)
<223> OTHER INFORMATION: Synthetic primer

<400> SEQUENCE: 168
aaatacaact gtcagcaaca ta                                       22
```

What is claimed is:

1. A method of mutation analysis of a target nucleic acid, said method comprising: incubating a sample comprising said target nucleic acid in a reaction mixture, in the presence of at least one first nucleic acid and at least one second nucleic acid, wherein said first nucleic acid comprises a primer sequence which anneals to a unique site of a sequence of SEQ ID NO. 1 or 2, said second nucleic acid has an opposite orientation from said first nucleic acid, said first or second nucleic acid comprises a sequence selected from the group consisting of SEQ ID NOs. 3–49; and wherein said incubation produces amplified products;

denaturing said amplified products and re-generating duplexes in said reaction mixture; and detecting the presence or absence of a heteroduplex from said duplexes, wherein the presence of a heteroduplex indicates the presence of a potential mutation in said target nucleic acid, and wherein the absence of a heteroduplex indicates the absence of a mutation in said target nucleic acid.

2. The method of claim 1, the method further comprising determining the sequence of a heteroduplex region; and comparing the sequence of the heteroduplex region to SEQ ID NO. 1 or 2; wherein a sequence difference in the heteroduplex region compared to SEQ ID NO. 1 or 2 resulting in a predicted functional change in the protein encoded by said target nucleic acid is indicative of a mutation in said target nucleic acid.

3. The method of claim 1, said method further comprising performing a nested amplification reaction using said amplified products generated by said first and second nucleic acids as templates and generating duplexes in amplified products from said nested amplification.

4. The method of claim 3, wherein said nested amplification reaction is performed using at least one primer selected from the group consisting of SEQ ID NOs. 3–49 and their complementary sequences.

5. The method of claim 1, wherein identifying the presence or absence of a heteroduplex from said duplexes is performed by DHPLC.

6. The method of claim 1, wherein the sequence of the heteroduplex region is determined by DNA sequencing.

7. The method of claim 1, wherein said second nucleic acid comprises a primer sequence which anneals to a unique site within a sequence of SEQ ID NO. 1 or 2.

8. The method of claim 1, wherein said sample comprising said target template is selected from the group consisting of: genomic DNA, cDNA, total RNA, mRNA, and a cell sample.

9. The method of claim 1, wherein said incubating comprises an amplification reaction selected from the group consisting of: a polymerase chain reaction, a ligase chain reaction (LCR) and a nucleic acid-specific based amplification.

10. The method of claim 1, further comprising confirming the amplified product is a PKD-specific product with one or more restriction enzymes.

11. The method of claim 10, wherein said restriction enzyme cleaves a PKD-specific product to generate a digestion pattern distinguishable from a PKD homologue product.

12. The method of claim 10, wherein said restriction enzyme is selected the group consisting of: Pst I, Stu I, Xma I, Mlu I, Pvu II, BssHII, Fsp I, Msc I, and Bln I.

13. A diagnosis method for identifying a patient affected with PKD, said method comprising:

(a) obtaining a sample from an individual;

(b) incubating said sample in a reaction mixture, in the presence of at least one first nucleic acid and at least one second nucleic acid, wherein said first nucleic acid comprises a primer sequence which anneals to a unique site within a sequence of SEQ ID NO. 1 or 2, and said second nucleic acid has an opposite orientation from said first nucleic acid, said first and second nucleic acid comprises a sequence selected from the group consisting of SEQ ID NOs. 3–49, and wherein said incubation produces amplified products;

(c) denaturing said amplified products and re-generating duplexes in said reaction mixture;

(d) detecting the presence or absence of a heteroduplex from said duplexes, and (e) determining the sequence of the heteroduplex region wherein the presence of a mutation in the heteroduplex region as compared to SEQ ID No. 1 or 2 is indicative that said individual is affected with PKD.

14. The method of claim 13, wherein said detection of a heteroduplex is performed by DHPLC.

15. The method of claim 13, wherein said sequence is determined by DNA sequencing.

16. The method of claim 13, wherein said second nucleic acid comprises a primer sequence which anneals to a unique site within a sequence of SEQ ID NO. 1 or 2.

17. The method of claim 13, said method further comprising performing a nested amplification reaction using said amplified products generated by said first and second nucleic acids as templates and generating duplexes from said nested amplification.

18. The method of claim 17, wherein said nested amplification reaction is performed using at least one primer selected from the group consisting of SEQ ID NOs. 3–49 and their complementary sequences.

19. The method of claim 13, wherein said sample is selected from the group consisting of: a genomic DNA, cDNA, total RNA, mRNA, and a cell.

20. The method of claim 13, wherein said amplification reaction is selected from the group consisting of: a polymerase chain reaction, a ligase chain reaction (LCR) and a nucleic acid-specific based amplification.

21. The method of claim 13, further comprising verifying a said specifically amplified product with one or more restriction enzymes.

22. The method of claim 21, wherein said restriction enzyme cleaves a PKD-specific product to generate a digestion pattern distinguishable from a PKD homologue product.

23. The method of claim 22 wherein said restriction enzyme is selected from the group consisting of: Pst I, Stu I, Xma I, Mlu I, Pvu II, BssHII, Fsp I, Msc I, and Bln I.

* * * * *